United States Patent
Nakano et al.

(10) Patent No.: US 9,960,364 B2
(45) Date of Patent: May 1, 2018

(54) LADDER COMPOUND, AND ORGANIC ELECTROLUMINESCENT ELEMENT USING SAME

(71) Applicant: Idemitsu Kosan Co., Ltd., Chiyoda-ku, Tokyo (JP)

(72) Inventors: Yuki Nakano, Sodegaura (JP); Ryohei Hashimoto, Sodegaura (JP); Kei Yoshida, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 287 days.

(21) Appl. No.: 14/435,126

(22) PCT Filed: Oct. 10, 2013

(86) PCT No.: PCT/JP2013/006061
§ 371 (c)(1),
(2) Date: Apr. 10, 2015

(87) PCT Pub. No.: WO2014/057684
PCT Pub. Date: Apr. 17, 2014

(65) Prior Publication Data
US 2015/0270496 A1    Sep. 24, 2015

(30) Foreign Application Priority Data
Oct. 11, 2012 (JP) ................. 2012-225916

(51) Int. Cl.
*H01L 51/00* (2006.01)
*C07D 487/14* (2006.01)
*C07D 491/14* (2006.01)
*C07D 491/22* (2006.01)
*C07D 495/14* (2006.01)
*C07D 495/22* (2006.01)
*C07D 519/00* (2006.01)
*H05B 33/20* (2006.01)
*C07D 491/147* (2006.01)
*H01L 51/50* (2006.01)
*H01L 51/52* (2006.01)

(52) U.S. Cl.
CPC ........ *H01L 51/0072* (2013.01); *C07D 487/14* (2013.01); *C07D 491/14* (2013.01); *C07D 491/147* (2013.01); *C07D 491/22* (2013.01); *C07D 495/14* (2013.01); *C07D 495/22* (2013.01); *C07D 519/00* (2013.01); *H01L 51/0071* (2013.01); *H01L 51/0073* (2013.01); *H01L 51/0074* (2013.01); *H01L 51/0085* (2013.01); *H05B 33/20* (2013.01); *C09K 2211/1007* (2013.01); *C09K 2211/1029* (2013.01); *C09K 2211/1033* (2013.01); *C09K 2211/1048* (2013.01); *C09K 2211/1059* (2013.01); *C09K 2211/1088* (2013.01); *C09K 2211/1092* (2013.01); *H01L 51/0059* (2013.01); *H01L 51/5016* (2013.01); *H01L 51/5056* (2013.01); *H01L 51/5088* (2013.01); *H01L 51/5092* (2013.01); *H01L 51/5206* (2013.01); *H01L 51/5221* (2013.01); *H01L 2251/301* (2013.01); *H01L 2251/308* (2013.01)

(58) Field of Classification Search
CPC .................................................. H01L 51/0072
USPC ........................................................ 428/690
See application file for complete search history.

(56) References Cited

U.S. PATENT DOCUMENTS

| | | |
|---|---|---|
| 8,993,783 B2 | 3/2015 | Lee et al. |
| 2004/0192871 A1 | 9/2004 | Wang et al. |
| 2008/0284322 A1 | 11/2008 | Hosokawa et al. |
| 2011/0248251 A1 | 10/2011 | Yamamoto et al. |
| 2012/0168734 A1 | 7/2012 | Park et al. |
| 2012/0223295 A1 | 9/2012 | Inoue et al. |

(Continued)

FOREIGN PATENT DOCUMENTS

| | | |
|---|---|---|
| JP | 2007-039406 A | 2/2007 |
| JP | 2011-198900 A | 10/2011 |
| KR | 10-2010-0094414 A | 8/2010 |

(Continued)

OTHER PUBLICATIONS

Hans-J. Teuber et al., "Heterohelicene aus Cyclohexandion-(1.4)-bis-phenylhydrazon[1])", *Chem. Ber.*, 1970, vol. 103, Issue 10, pp. 3319-3342.

(Continued)

*Primary Examiner* — Doris L Lee
(74) *Attorney, Agent, or Firm* — Foley & Lardner LLP

(57) ABSTRACT

A compound represented by the following formula (1). In the formula (1), when $Ar_1$ and $Ar_2$ are the same substituents, as for all of the following pairs: $Y_1$ and $Y_{12}$, $Y_2$ and $Y_{11}$, $Y_3$ and $Y_{10}$, $Y_4$ and $Y_9$, $Y_5$ and $Y_8$, and $Y_6$ and $Y_7$, $Y_1$ to $Y_{12}$ of each pair are not the same as each other.

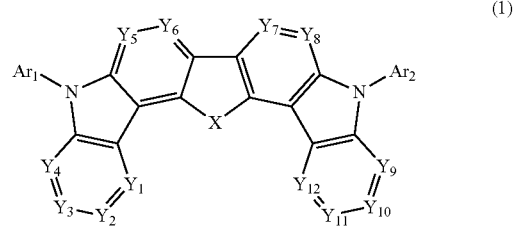

(1)

15 Claims, 1 Drawing Sheet

(56) References Cited

U.S. PATENT DOCUMENTS

Figure 1:
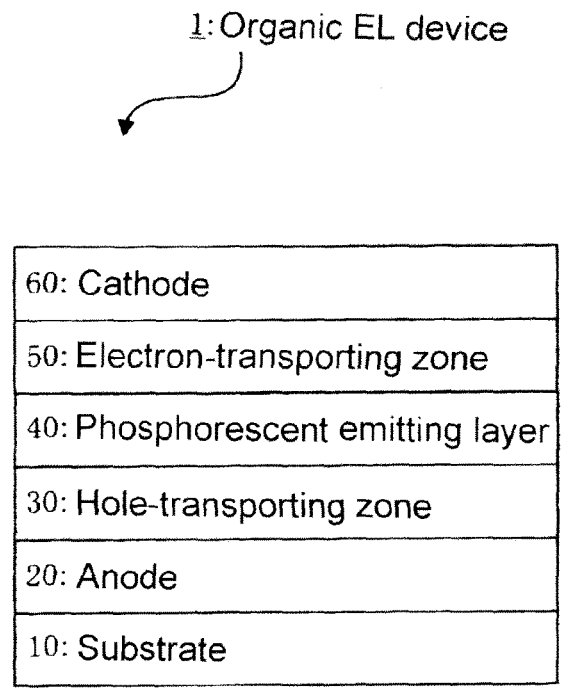

2013/0087776 A1  4/2013  Lee et al.

FOREIGN PATENT DOCUMENTS

| WO | WO-2010/050496 A1 | 5/2010 |
| WO | WO-2011/019173 A2 | 2/2011 |
| WO | WO 2011/152596 A1 | 12/2011 |
| WO | WO-2012/108389 A1 | 8/2012 |

OTHER PUBLICATIONS

International Search Report issued in PCT/JP2013/006061 dated Jan. 21, 2014.
Translation of Written Opinion of the International Searching Authority issued in International Application No. PCT/JP2013/006061 dated Apr. 14, 2015.
Office Action dated Aug. 10, 2017 in Chinese Patent Application No. 201380053087.2.

LADDER COMPOUND, AND ORGANIC ELECTROLUMINESCENT ELEMENT USING SAME

CROSS REFERENCE TO RELATED APPLICATIONS

This application is the National Phase of PCT/JP2013/006061, filed Oct. 10, 2013, which claims priority to Japanese Application No. 2012-225916, filed Oct. 11, 2012.

TECHNICAL FIELD

The invention relates to a novel ladder compound, a material for an organic electroluminescence device using the same and an organic electroluminescence device.

BACKGROUND ART

An organic electroluminescence (EL) device includes a fluorescent organic EL device and a phosphorescent organic EL device, and a device design optimum for the emission mechanism of each type of organic EL devices has been studied. It is known that a highly efficient phosphorescent organic EL device cannot be obtained by merely applying fluorescent device technology due to the emission characteristics.

Specifically, since phosphorescence emission utilizes triplet excitons, a compound used for forming an emitting layer must have a large energy gap. This is because the energy gap (hereinafter often referred to as "singlet energy") of a compound is normally larger than the triplet energy (in the invention, the difference in energy between the lowest excited triplet state and the ground state) of the compound.

As the material for a phosphorescent organic EL device, Patent Document 1 discloses a phosphorescent host material having a line symmetrical structure, for example.

RELATED ART DOCUMENTS

Patent Documents

Patent Document 1: WO2011/019173

An object of the invention is to provide a compound capable of improving efficiency of an organic EL device.

According to the invention, the following ladder compounds or the like are provided.

1. A compound represented by the following formula (1):

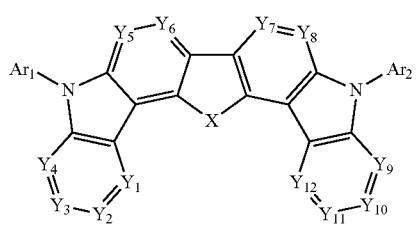

(1)

wherein in the formula (1),
X is O, S or a group represented by N—Ra;
$Y_1$ to $Y_{12}$ are independently N or a group represented by C—Ra;
$Ar_1$ and $Ar_2$ are independently a substituted or unsubstituted aryl group including 6 to 30 carbon atoms that form a ring (hereinafter referred to as "ring carbon atoms") or a substituted or unsubstituted heteroaryl group including 5 to 30 atoms that form a ring (hereinafter referred to as "ring atoms");
Ra is a hydrogen atom, a deuterium atom, a substituted or unsubstituted aryl group including 6 to 30 ring carbon atoms, a substituted or unsubstituted heteroaryl group including 5 to 30 ring atoms, a substituted or unsubstituted alkyl group including 1 to 30 carbon atoms, a substituted or unsubstituted fluoroalkyl group including 1 to 30 carbon atoms, a substituted or unsubstituted cycloalkyl group including 3 to 30 ring carbon atoms, a substituted or unsubstituted aralkyl group including 7 to 30 carbon atoms, a substituted phosphoryl group, a substituted silyl group, a substituted germanium group, a cyano group, a nitro group or a carboxy group;
if two or more Ras are present in the formula (1), the plural Ras may be the same or different; and
provided that, when $Ar_1$ and $Ar_2$ are the same substituents, as for all of the following pairs: $Y_1$ and $Y_{12}$, $Y_2$ and $Y_{11}$, $Y_3$ and $Y_{10}$, $Y_4$ and $Y_9$, $Y_5$ and $Y_8$, and $Y_6$ and $Y_7$, $Y_1$ to $Y_{12}$ of each pair are not the same as each other.

2. The compound according to 1, wherein $Ar_1$ and $Ar_2$ in the formula (1) are independently a substituted or unsubstituted aryl group including 6 to 30 ring carbon atoms.

3. The compound according to 1, wherein $Ar_1$ and $Ar_2$ in the formula (1) are independently a substituted or unsubstituted heteroaryl group including 5 to 30 ring atoms.

4. The compound according to any one of 1 to 3, wherein X in the formula (1) is a group represented by N—Ra.

5. The compound according to any one of 1 to 3, wherein X in the formula (1) is O or S.

6. The compound according to any one of 1 to 5, wherein $Y_1$ to $Y_{12}$ in the formula (1) are independently a group represented by C—Ra.

7. The compound according to any one of 1 to 6, wherein $Ar_1$ in the formula (1) is represented by -$L_1$-$R_1$:
wherein $L_1$ is a substituted or unsubstituted arylene group including 6 to 30 ring carbon atoms or a substituted or unsubstituted heteroarylene group including 5 to 30 ring atoms; and $R_1$ is a substituted or unsubstituted aryl group including 6 to 30 ring carbon atoms or a substituted or unsubstituted heteroaryl group including 5 to 30 ring atoms.

8. The compound according to 7, wherein $L_1$ is a substituted or unsubstituted arylene group including 6 to 30 ring carbon atoms.

9. The compound according to 7, wherein $L_1$ is a substituted or unsubstituted heteroarylene group including 5 to 30 ring atoms.

10. A material for an organic electroluminescence device that comprises the compound according to any one of 1 to 9.

11. A hole-transporting material for an organic electroluminescence device that is represented by the following formula (2):

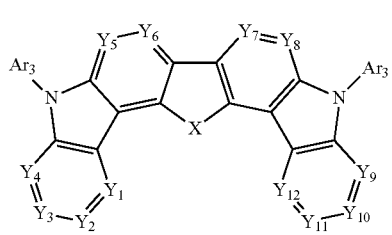

(2)

wherein in the formula (2),

X is O, S or a group represented by N—Ra;

$Y_1$ to $Y_{12}$ are independently N or a group represented by C—Ra;

the two $Ar_3$s are the same substituted or unsubstituted heteroaryl group including 5 to 30 ring atoms;

Ra is a hydrogen atom, a deuterium atom, a substituted or unsubstituted aryl group including 6 to 30 ring carbon atoms, a substituted or unsubstituted heteroaryl group including 5 to 30 ring atoms, a substituted or unsubstituted alkyl group including 1 to 30 carbon atoms, a substituted or unsubstituted fluoroalkyl group including 1 to 30 carbon atoms, a substituted or unsubstituted cycloalkyl group including 3 to 30 ring carbon atoms, a substituted or unsubstituted aralkyl group including 7 to 30 carbon atoms, a substituted phosphoryl group, a substituted silyl group, a cyano group, a nitro group or a carboxy group;

if two or more Ras are present in the formula (2), the plural Ras may be the same or different; and provided that, as for all of the following pairs: $Y_1$ and $Y_{12}$, $Y_2$ and $Y_{11}$, $Y_3$ and $Y_{10}$, $Y_4$ and $Y_9$, $Y_5$ and $Y_8$, and $Y_6$ and $Y_7$, $Y_1$ to $Y_{12}$ of each pair are the same as each other.

12. A hole-transporting material for an organic electroluminescence device that is represented by the following formula (3):

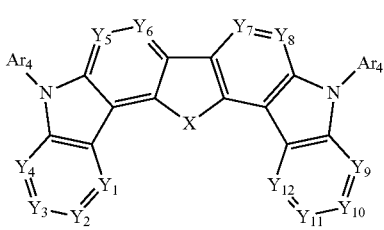

(3)

wherein in the formula (3),

X is O, S or a group represented by N—Ra;

$Y_1$ to $Y_{12}$ are independently N or a group represented by C—Ra;

the two $Ar_4$s are the same substituted or unsubstituted aryl group including 6 to 30 ring carbon atoms;

Ra is a hydrogen atom, a deuterium atom, a substituted or unsubstituted aryl group including 6 to 30 ring carbon atoms, a substituted or unsubstituted heteroaryl group including 5 to 30 ring atoms, a substituted or unsubstituted alkyl group including 1 to 30 carbon atoms, a substituted or unsubstituted fluoroalkyl group including 1 to 30 carbon atoms, a substituted or unsubstituted cycloalkyl group including 3 to 30 ring carbon atoms, a substituted or unsubstituted aralkyl group including 7 to 30 carbon atoms, a substituted phosphoryl group, a substituted silyl group, a cyano group, a nitro group or a carboxy group;

if two or more Ras are present in the formula (3), the plural Ras may be the same or different; and provided that, as for all of the following pairs: $Y_1$ and $Y_{12}$, $Y_2$ and $Y_{11}$, $Y_3$ and $Y_{10}$, $Y_4$ and $Y_9$, $Y_5$ and $Y_8$, and $Y_6$ and $Y_7$, $Y_1$ to $Y_{12}$ of each pair are the same as each other.

13. An organic electroluminescence device comprising:
an anode and a cathode; and
one or more organic thin film layers including an emitting layer between the anode and the cathode,
wherein at least one layer of the organic thin film layers comprises the material for an organic electroluminescence device according to 10.

14. The organic electroluminescence device according to 13, wherein the emitting layer comprises the material for an organic electroluminescence device.

15. The organic electroluminescence device according to 14, further comprising an electron-transporting zone between the cathode and the emitting layer, wherein the electron-transporting zone comprises the material for an organic electroluminescence device.

16. An organic electroluminescence device comprising:
an anode and a cathode;
one or more organic thin film layers including an emitting layer between the anode and the cathode; and
a hole-transporting zone between the anode and the emitting layer;
wherein the hole-transporting zone comprises the hole-transporting material for an organic electroluminescence device according to 11.

17. An organic electroluminescence device comprising:
an anode and a cathode;
one or more organic thin film layers including an emitting layer between the anode and the cathode; and a hole-transporting zone between the anode and the emitting layer,
wherein the hole-transporting zone comprises the hole-transporting material for an organic electroluminescence device according to 12.

18. The organic electroluminescence device according to any one of 13 to 17, wherein the emitting layer comprises a phosphorescent emitting material and the phosphorescent emitting material is an ortho-metalated complex of a metal atom selected from iridium (Ir), osmium (Os) and platinum (Pt).

According to the invention, it is possible to provide a compound that enables an organic EL device to emit light highly efficiently.

BRIEF DESCRIPTION OF THE INVENTION

Figure 2:
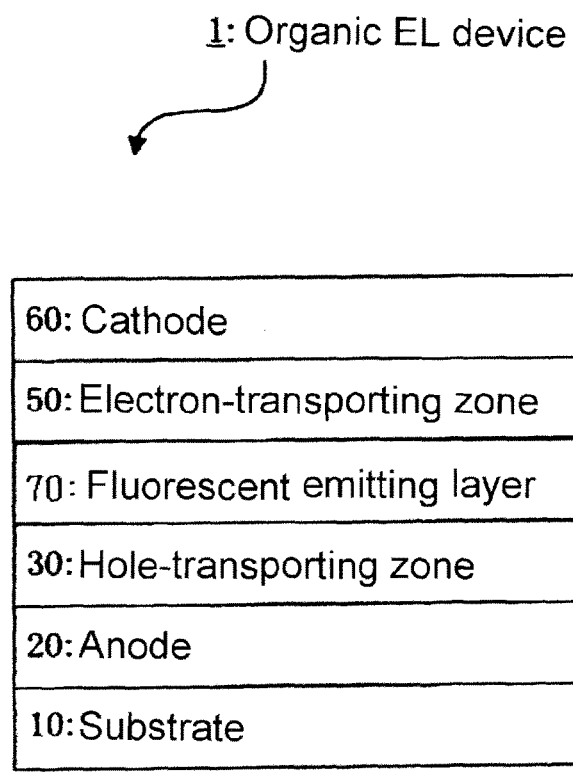

FIG. 1 is a view showing one embodiment of the organic EL device of the invention; and FIG. 2 is a view showing one embodiment of the organic EL device of the invention.

MODE FOR CARRYING OUT THE INVENTION

The compound of the invention is represented by the following formula (1):

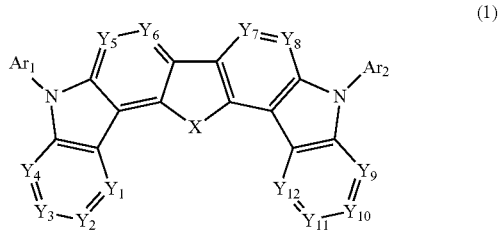

(1)

wherein in the formula (1),

X is O, S or a group represented by N—Ra;

$Y_1$ to $Y_{12}$ are independently N or a group represented by C—Ra;

$Ar_1$ and $Ar_2$ are independently a substituted or unsubstituted aryl group including 6 to 30 ring carbon atoms or a substituted or unsubstituted heteroaryl group including 5 to 30 ring atoms;

Ra is a hydrogen atom, a deuterium atom, a substituted or unsubstituted aryl group including 6 to 30 ring carbon atoms, a substituted or unsubstituted heteroaryl group including 5 to 30 ring atoms, a substituted or unsubstituted alkyl group including 1 to 30 carbon atoms, a substituted or unsubstituted fluoroalkyl group including 1 to 30 carbon atoms, a substituted or unsubstituted cycloalkyl group including 3 to 30 ring carbon atoms, a substituted or unsubstituted aralkyl group including 7 to 30 carbon atoms, a substituted phosphoryl group, a substituted silyl group, a substituted germanium group, a cyano group, a nitro group or a carboxy group;

if two or more Ras are present in the formula (1), the plural Ras may be the same or different; and provided that, when $Ar_1$ and $Ar_2$ are the same substituent, as for all of the following pairs: $Y_1$ and $Y_{12}$, $Y_2$ and $Y_{11}$, $Y_3$ and $Y_{10}$, $Y_4$ and $Y_9$, $Y_5$ and $Y_8$, and $Y_6$ and $Y_7$, $Y_1$ to $Y_{12}$ of each pair are not the same group with each other.

The compound of the invention has, as a central skeleton, a bisindrodibenzofuran skeleton, a bisindrodibenzothiophene skeleton or a bisindrocarbazole skeleton, that is a skeleton having an extended π-conjugated plane, forms a ladder structure, and hence has excellent carrier transporting properties.

By using the compound of the invention having excellent carrier transporting properties as the material of an organic EL device, the carrier balance in the device can be adjusted, whereby the efficiency of the device can be improved.

Further, in the formula (1), a structure including a hetero atom X is bonded to the 3rd and 4th positions of the two carbazolyl groups that constitute the compound shown in the formula (1), thereby forming a ladder structure. This ladder structure contributes to formation of a compound having a large triplet energy.

In the compound of the invention, if $Ar_1$ and $Ar_2$ are the same substituents, as for all of the following pairs: $Y_1$ and $Y_{12}$, $Y_2$ and $Y_{11}$, $Y_3$ and $Y_{10}$, $Y_4$ and $Y_9$, $Y_5$ and $Y_8$, and $Y_6$ and $Y_7$, $Y_1$ to $Y_{12}$ of each pair are not the same group with each other. That is, the carbazole part formed by $Y_1$ to $Y_6$ and the carbazole part formed by $Y_7$ to $Y_{12}$ have different structures from each other, and the compound of the invention does not have a line symmetrical structure.

In the compound of the invention, it is preferred that $Ar_1$ and $Ar_2$ be different substituents. Here, if $Ar_1$ and $Ar_2$ are the same groups, if they bond to the ladder structure at different positions, the compound does not take a line symmetrical structure. Therefore, $Ar_1$ and $Ar_2$ are different substituents. As examples of such a structure, a structure can be given in which, of the two dibenzofuranyl groups constituting $Ar_1$ and $Ar_2$, one is bonded to the ladder structure at the 2nd position, and the other is bonded to the ladder structure at the 4th position. However, as for the structure before bonding to the ladder structure, it is preferred that the structure before bonding to the ladder structure, i.e. $Ar_1$ and $Ar_2$ be different groups.

Due to the asymmetricstructure, the compound of the invention has low crystallinity, and keeps an amorphous organic film, whereby adequate hole-transporting properties can be maintained.

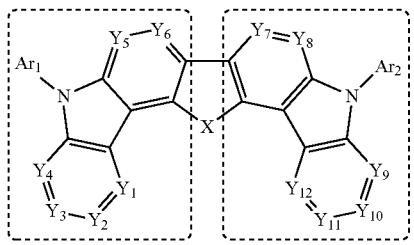

$Ar_1$ and $Ar_2$ are preferably a substituted or unsubstituted aryl group including 6 to 30 ring carbon atoms, or a substituted or unsubstituted heteroaryl group including 5 to 30 ring atoms.

In one aspect, $Ar_1$ is represented by $-L_1-R_1$. $L_1$ is a substituted or unsubstituted arylene group including 6 to 30 ring carbon atoms, or a substituted or unsubstituted heteroarylene group including 5 to 30 ring atoms. $R_1$ is a substituted or unsubstituted aryl group including 6 to 30 ring carbon atoms or a substituted or unsubstituted heteroaryl group including 5 to 30 ring atoms.

X is preferably a group represented by N—Ra or O or S.

In respect of a long lifetime, it is preferred that $Y_1$ to $Y_{12}$ be independently a group represented by C—Ra, further preferably —CH. If adjacent groups of $Y_1$ to $Y_{12}$ are C—Ra (may be —CH), these adjacent groups may be bonded each other to form a ring. In respect of keeping the extended π-conjugated plane, it is preferred that the ring formed by bonding of adjacent groups be an aromatic ring. In this case, the aromatic ring may be an aromatic ring that contains a hetero atom such as N, O and S as a ring atom. On the other hand, if an organic EL device is produced by forming an organic thin film of the compound represented by the formula (1) by the vapor deposition method, a compound that forms a ladder by the seven rings as shown in the formula (1) is preferable.

Hereinbelow, an explanation will be made on examples of each group of the compound represented by the formula (1).

As the alkyl group including 1 to 30 carbon atoms, a linear or branched alkyl group can be mentioned. Specific examples thereof include a methyl group, an ethyl group, a propyl group, an isopropyl group, a n-butyl, group, an isobutyl group, a sec-butyl group, a tert-butyl group, a n-pentyl group, a n-hexyl group, a n-heptyl group, a n-octyl group or the like. Among these, a methyl group, an ethyl group, a propyl group, an isopropyl group, a n-butyl group, an isobutyl group, a sec-butyl group and a tert-butyl group. A methyl group, an ethyl group, a propyl group, an isopropyl group, a n-butyl group, a sec-butyl group and a tert-butyl group are more preferable.

As the fluoroalkyl group including 1 to 30 carbon atoms, a group in which the alkyl group mentioned above is substituted by one or more fluorine atoms can be given. Specific examples thereof include a fluoromethyl group, a difluoromethyl group, a trifluoromethyl group, a fluoroethyl group, a trifluoromethylmethyl group, a pentafluoroethyl group and the like. A trifluoromethyl group and a pentafluoroethyl group are preferable.

As the cycloalkyl group including 3 to 30 ring carbon atoms, a cyclopropyl group, a cyclobutyl group, a cyclopentyl group, a cyclohexyl group, a 1-adamantyl group, a 2-adamantyl group, a 1-norbornyl group, a 2-norbornyl group or the like can be given. A cyclopentyl group and a cyclohexyl group are preferable.

The "carbon atoms that form a ring" means carbon atoms that form a saturated ring, an unsaturated ring or an aromatic ring.

The aryl group including 6 to 30 ring carbon atoms is preferably an aryl group including 6 to 20 ring carbon atoms.

Specific examples of the aryl group include a phenyl group, a naphthyl group, an anthryl group, a phenanthryl group, a naphthacenyl group, a pyrenyl group, a chrysenyl group, a benzo[c]phenanthryl group, a benzo[g]chrysenyl group, a triphenylenyl group, a fluorenyl group, a benzofluorenyl group, a dibenzofluorenyl group, a biphenylyl group, a terphenyl group, a quarterphenyl group, a fluoranthenyl group or the like. Among them, a naphthyl group, an anthryl group, a phenanthryl group, a naphthacenyl group, a pyrenyl group and a chrysenyl group are preferable.

The arylene group including 6 to 30 ring carbon atoms is preferably an arylene group including 6 to 20 ring carbon atoms. Specific examples thereof include divalent groups of the above-mentioned aryl groups.

As the hetero atom that constitutes the heteroaryl group including 5 to 30 ring atoms, an oxygen atom, a sulfur atom and a nitrogen atom can be given. The heteroaryl group may be a heteroaryl group including 3 to 30 ring atoms or a heteroaryl group including 3 to 30 ring carbon atoms. As for the hetero atoms that constitute these heteroaryl groups, the same as mentioned above can be given.

Specific examples of the heteroaryl group include a pyrrolyl group, a pyrazinyl group, a pyridinyl group, a pyrimidinyl group, a triazinyl group, an indolyl group, an isoindolyl group, an imidazolyl group, a furyl group, a benzofuranyl group, an isobenzofuranyl group, a dibenzofuranyl group, a dibenzothiophenyl group, an azadibenzofuranyl group, an azadibenzothiophenyl group, a diazadibenzofuranyl group, a diazadibenzothiophenyl group, a quinolyl group, an isoquinolyl group, a quinoxalinyl group, a carbazolyl group, a phenanthridinyl group, an acridinyl group, a phenanthrolinyl group, a phenazinyl group, a phenothiazinyl group, a phenoxazinyl group, an oxazolyl group, an oxadiazolyl group, a furazanyl group, a thienyl group, a benzothiophenyl group, a dihydroacridinyl group, an azacarbazolyl group, a diazacarbazolyl group and a quinazolinyl group. Among these, a pyridinyl group, a pyrimidinyl group, a triazinyl group, a dibenzofuranyl group, a dibenzothiophenyl group, an azadibenzofuranyl group, an azadibenzothiophenyl group, a diazadibenzofuranyl group, a diazadibenzothiophenyl group, a carbazolyl group, an azacarbazolyl group and a diazacarbazolyl group are preferable.

When the compound represented by the formula (1) is used in a blue-emitting phosphorescent organic EL device, a dibenzofuranyl group, a dibenzothiophenyl group, an azadibenzofuranyl group, an azadibenzothiophenyl group, a diazadibenzofuranyl group, a diazadibenzothiophenyl group, a carbazolyl group, an azacarbazolyl group and a diazacarbazolyl group are preferable.

As the heteroarylene group including 5 to 30 ring atoms, a divalent group of the above-mentioned heteroaryl group can be mentioned, specifically.

The aralykyl group including 7 to 30 carbon atoms is represented by —Y—Z. As examples of Y, the examples of the alkylene group corresponding to the examples of the alkyl group mentioned above can be given. As examples of Z, the examples of the aryl group mentioned above can be given.

It is preferred that the aryl part of the aralkyl group include 6 to 20 ring carbon atoms. The alkyl part preferably includes 1 to 8 carbon atoms. As the aralkyl group, a benzyl group, a phenylethyl group and a 2-phenylpropan-2-yl group can be mentioned, for example.

The substituted phosphoryl group is a group represented by —P(=O)RbRc, for example. The substituted silyl group is a group represented by —SiRbRcRd, for example. The substituted germanium group is a group represented by —GeRbRcRd, for example.

Rb, Rc and Rd are independently a substituted or unsubstituted aryl group including 6 to 30 ring carbon atoms, a substituted or unsubstituted heteroaryl group including 5 to 30 ring atoms, a substituted or unsubstituted alkyl group including 1 to 30 carbon atoms, a substituted or unsubstituted fluoroalkyl group including 1 to 30 carbon atoms or a substituted or unsubstituted cycloalkyl group including 3 to 30 ring carbon atoms.

Each group of these Rb, Rc and Rd are the same as those mentioned above.

As the substituent of the "substituted or unsubstituted . . . " of each of the above-mentioned groups, the alkyl group, the cycloalkyl group, the fluoroalkyl group, the aryl group and the heteroaryl group as mentioned above can be given. In addition, a halogen atom (fluorine, chlorine, bromine, iodine or the like can be given, and a fluorine atom is preferably given), a hydroxyl group, a nitro group, a cyano group, a carboxy group, an aryloxy group, a substituted phosphoryl group, a substituted silyl group, a substituted germanium group or the like can be given.

As the substituent for the substituted or unsubstituted aryl group including 6 to 30 ring carbon atoms, a substituted or unsubstituted aryl group including 6 to 30 ring carbon atoms or a substituted or unsubstituted heteroaryl group including 5 to 30 ring atoms are preferable. As the specific examples of the aryl group, a phenyl group, a naphthyl group, an anthryl group, a phenanthryl group, a naphthacenyl group, a pyrenyl group, a chrysenyl group, a benzo[c]phenanthryl group, a benzo[g]chrysenyl group, a triphenylenyl group, a fluorenyl group, a benzofluorenyl group, a dibenzofluorenyl group, a biphenylyl group, a terphenyl group, a quarterphenyl group and a fluoranthenyl group or the like can be given. A phenyl group, a naphthyl group, a triphenylenyl group, a fluorenyl group, and a biphenylyl group are preferable. Specific examples of the heteroaryl group include a pyrrolyl group, a pyrazinyl group, a pyridinyl group, a pyrimidinyl group, a triazinyl group, an indolyl group, an isoindolyl group, an imidazolyl group, a furyl group, a benzofuranyl group, an isobenzofuranyl group, a dibenzofuranyl group, a dibenzothiophenyl group, an azadibenzofuranyl group, an azadibenzothiophenyl group, a diazadibenzofuranyl group, a diazadibenzothiophenyl group, a quinolyl group, an isoquinolyl group, a quinoxalinyl group, a carbazolyl group, a phenanthridinyl group, an acridinyl group, a phenanthrolinyl group, a phenazinyl group, a phenothiazinyl group, a phenoxazinyl group, an oxazolyl group, an oxadiazolyl group, a furazanyl group, a thienyl group, a benzothiophenyl group, a dihydroacridinyl group, an azacarbazolyl group, a diazacarbazolyl group and a quinazoliny group can be given. Among these, a dibenzofuranyl group, a dibenzothiophenyl group, an azadibenzofuranyl group, an azadibenzothiophenyl group, a diazadibenzofuranyl group, a diazadibenzothiophenyl group, a carbazolyl group, an azacarbazolyl group and a diazacarbazolyl group can preferably be given.

As the substituent of the substituted or unsubstituted heteroaryl group including 5 to 30 ring atoms, a substituted or unsubstituted aryl group including 6 to 30 ring carbon atoms and a substituted or unsubstituted heteroaryl group including 5 to 30 ring atoms are preferable. As examples of the aryl group, specifically, a phenyl group, a naphthyl group, an anthryl group, a phenanthryl group, a naphthacenyl group, a pyrenyl group, a crysenyl group, a benzo[c]phenanthryl group, a benzo[g]crysenyl group, a triphenylenyl group, a fluorenyl group, a benzofluorenyl group, a dibenzofluorenyl group, a biphenylyl group, a terphenyl group, a quarterphenyl group, a fluoranthenyl group or the like can be given. A phenyl group, a naphthyl group, a triphenylenyl group, a fluorenyl group and a biphenylyl group can preferably be given. As the specific examples of the heteroaryl group, a pyrrolyl group, a pyrazinyl group, a pyridinyl group, a pyrimidinyl group, a triazinyl group, an indolyl group, an isoindolyl group, an imidazolyl group, a furyl group, a benzofuranyl group, an isobenzofuranyl group, a dibenzofuranyl group, a dibenzothiophenyl group, an azadibenzofuranyl group, an azadibenzothiophenyl group, a diazadibenzofuranyl group, a diazadibenzothiophenyl group, a quinolyl group, an isoquinolyl group, a quinoxalinyl group, a carbazolyl group, a phenanthridinyl group, an acridinyl group, a phenanthrolinyl group, a phenazinyl group, a phenothiazinyl group, a phenoxazinyl group, an oxazolyl group, an oxadiazolyl group, a furazanyl group, a thienyl group, a benzothiophenyl group, a dihydroacridinyl group, an azacarbazolyl group, a diazacarbazolyl group and a quinazolinyl group can be given. A dibenzofuranyl group, a dibenzothiophenyl group, an azadibenzofuranyl group, an azadibenzothiophenyl group, a diazadibenzofuranyl group, a diazadibenzothiophenyl group, a carbazolyl group, an azacarbazolyl group and a diazacarbazolyl group are preferable.

No specific restrictions are imposed on the method for producing the compound represented by the formula (1) of the invention, and the compound can be produced by a known method.

Hereinbelow, specific examples of the compound represented by the formula (1) are given below.

(1)

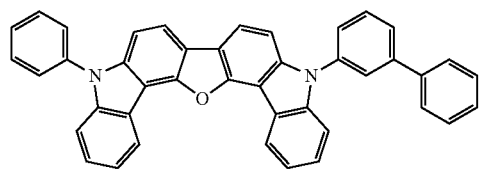

(2)

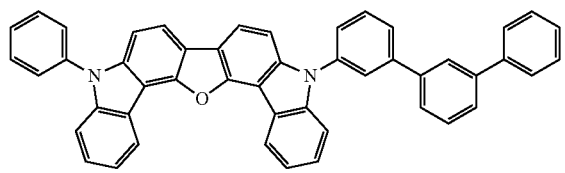

(3)

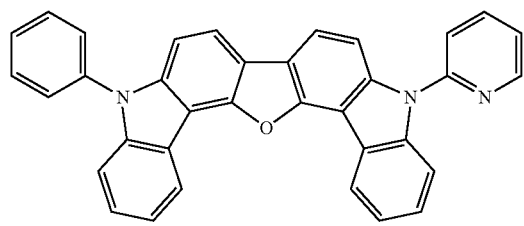

(4)

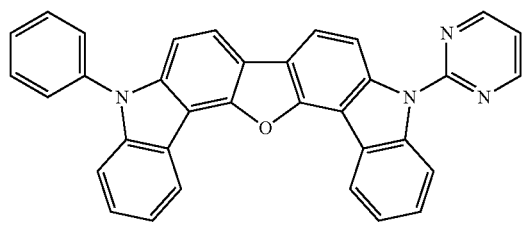

(5)

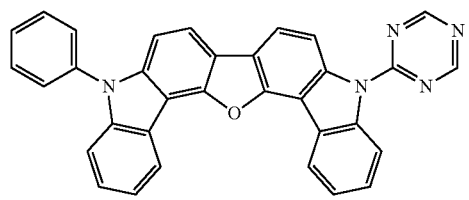

(6)

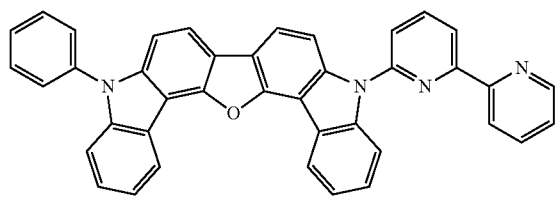

(7)

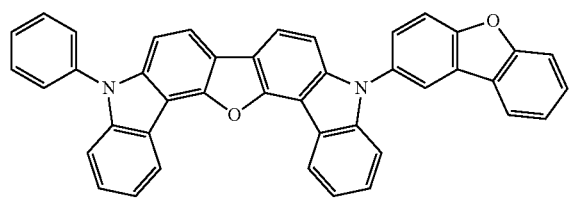

(8)

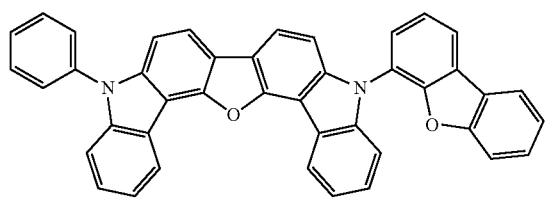

(9)

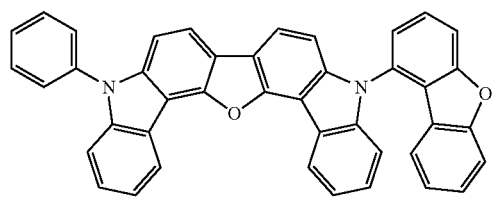

(10)

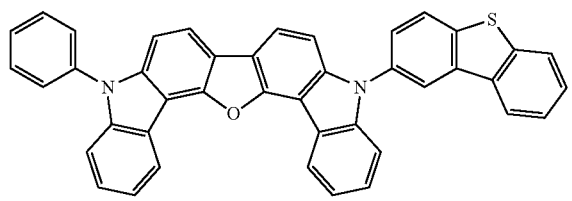

-continued
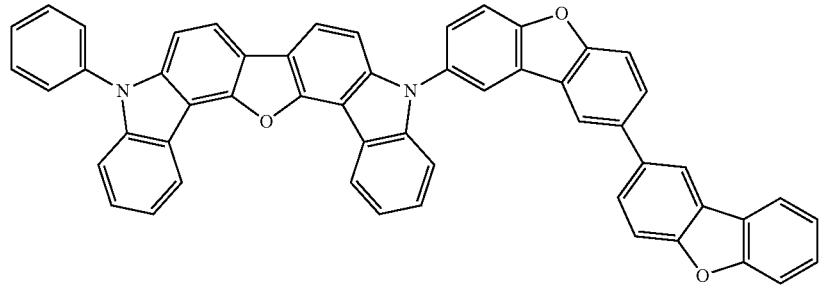
(11)
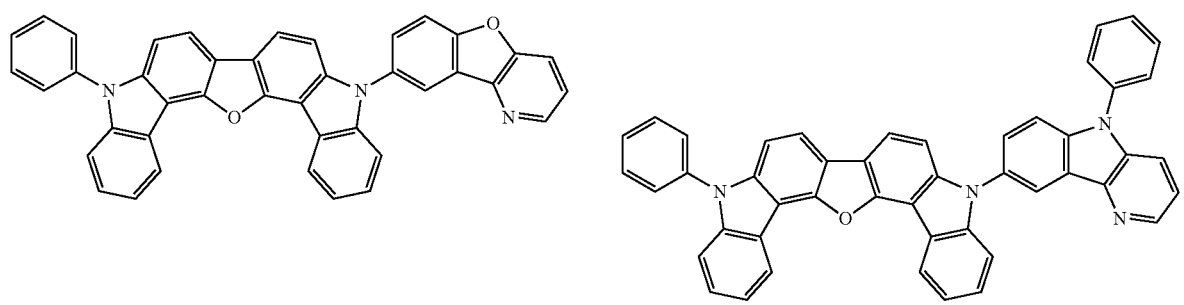
(12) (13)
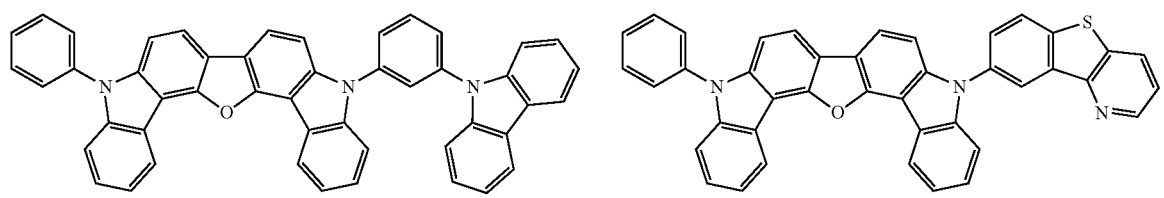
(14) (15)
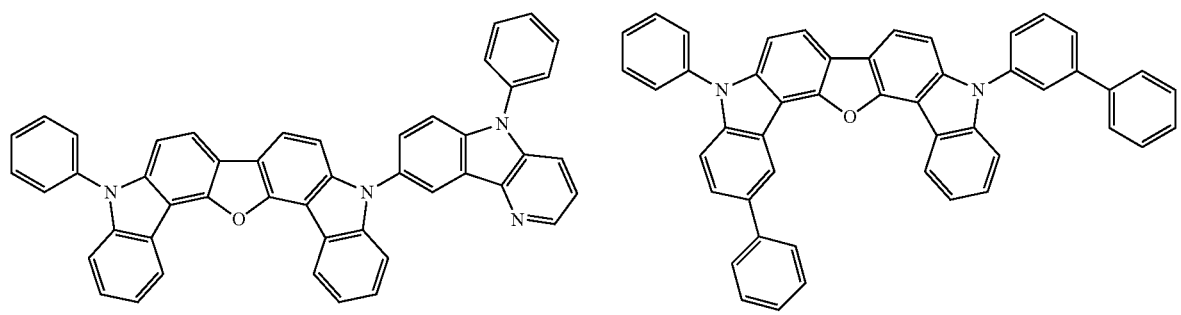
(16) (17)
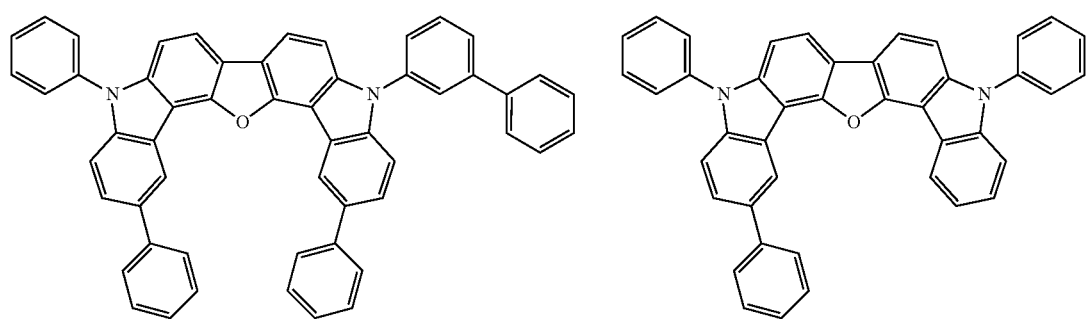
(18) (19)

-continued
(20)
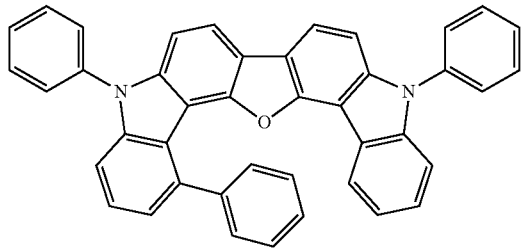
(21)
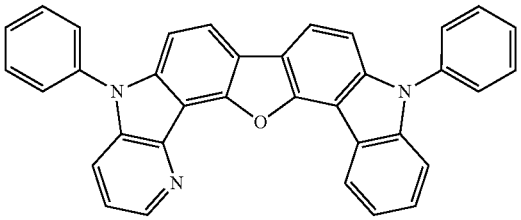
(22)
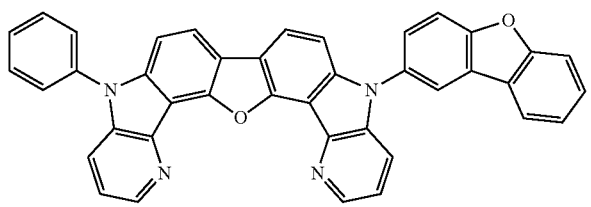
(23)
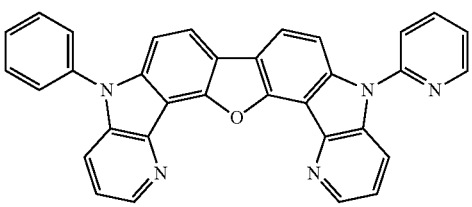
(24)
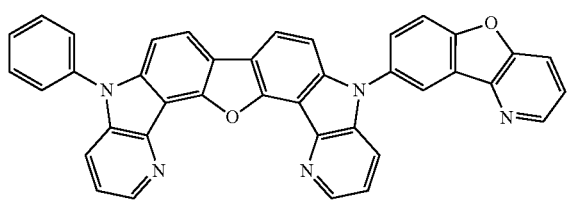
(25)
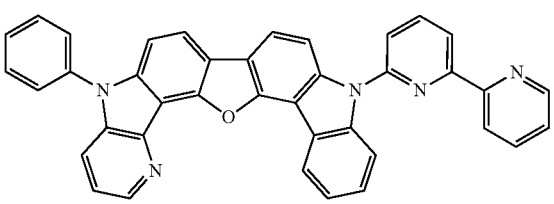
(26)
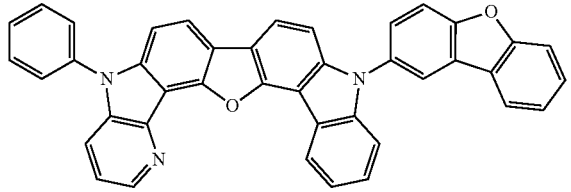
(27)
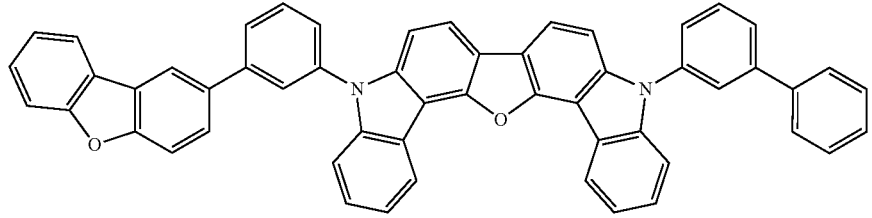
(28)
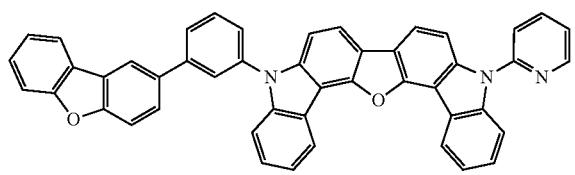
(29)
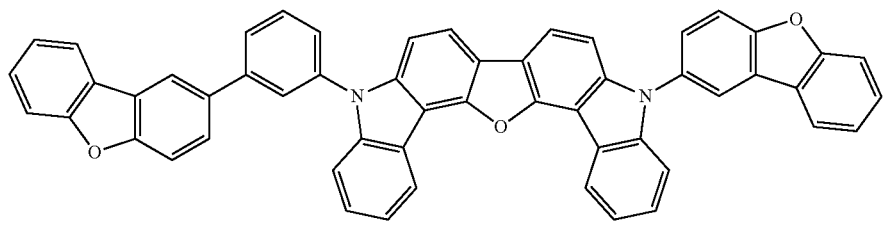

-continued
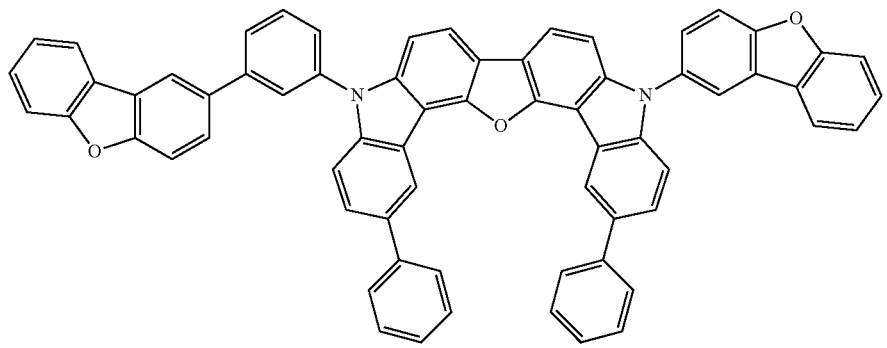
(30)
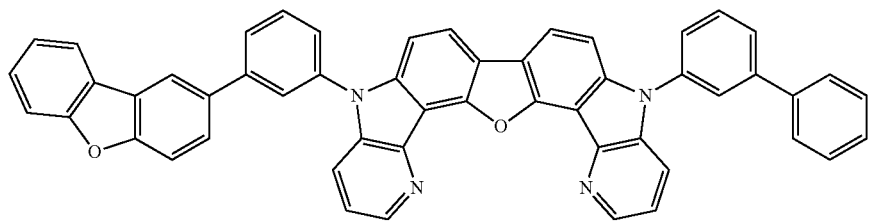
(31)
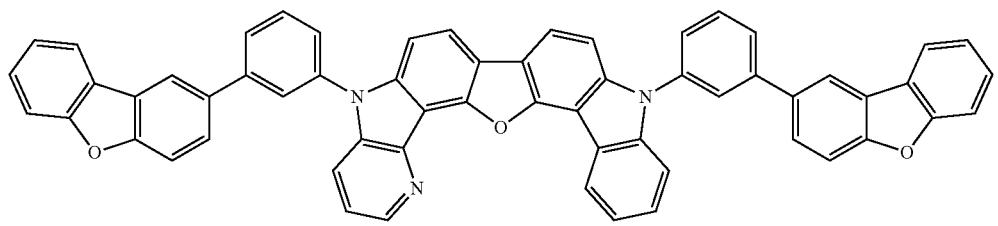
(32)
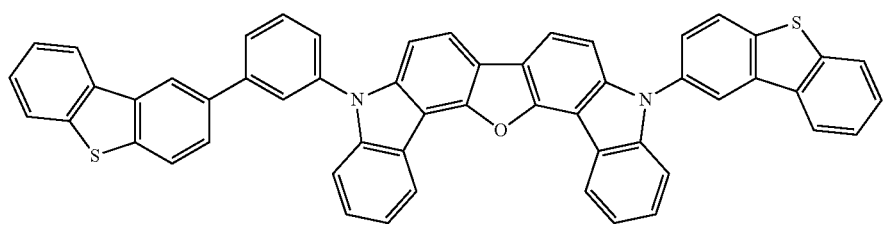
(33)
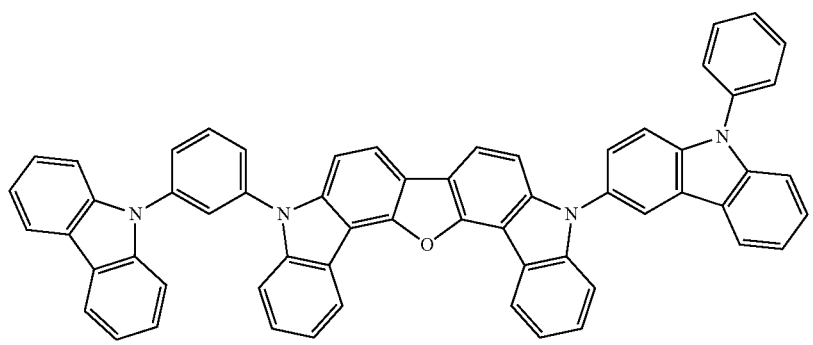
(34)
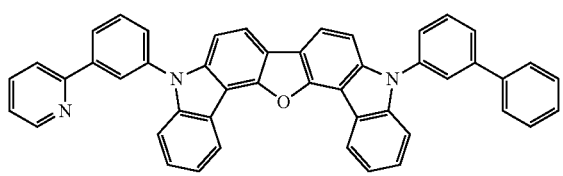
(35)
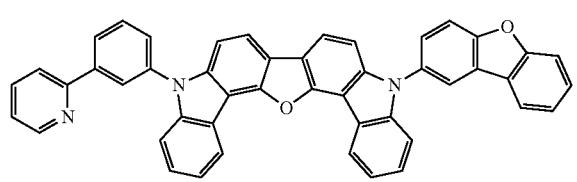
(36)

-continued
(37)
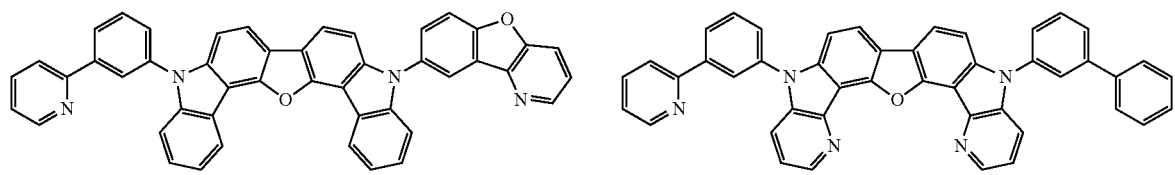
(38)
(39)
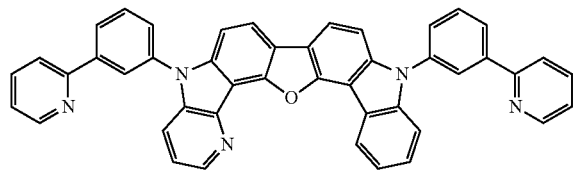
(40)
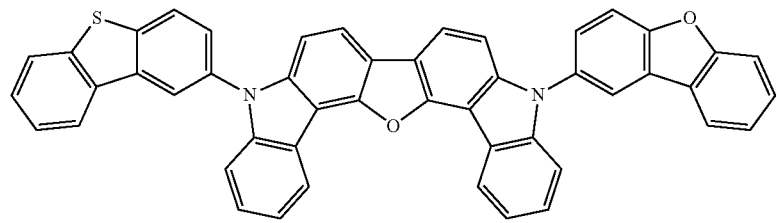
(41)
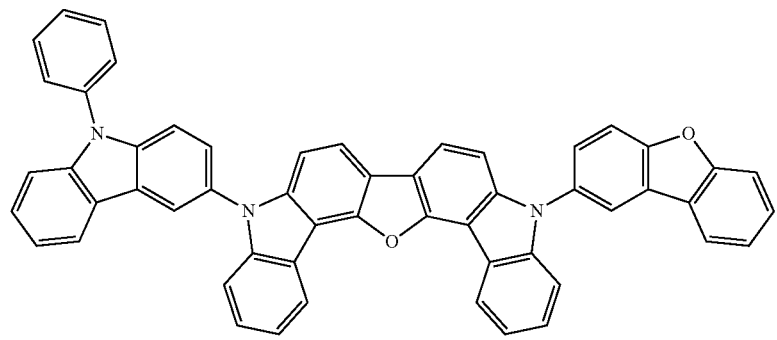
(42)
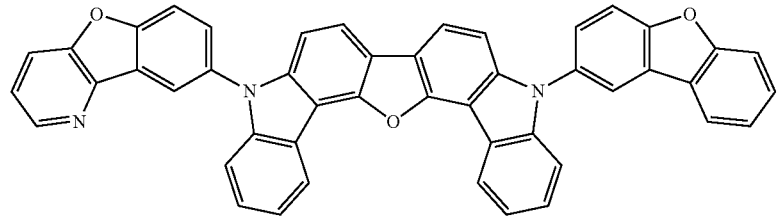
(43)
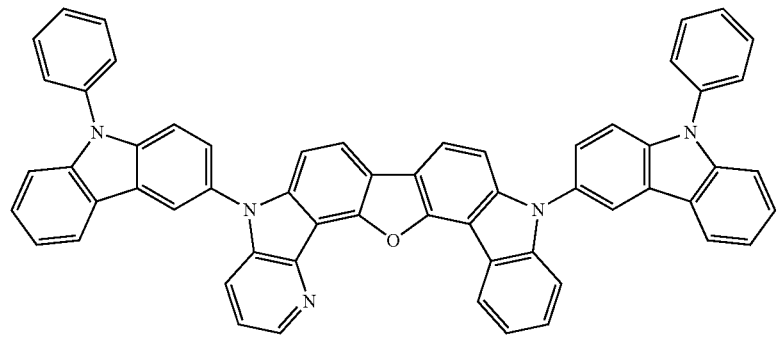

-continued
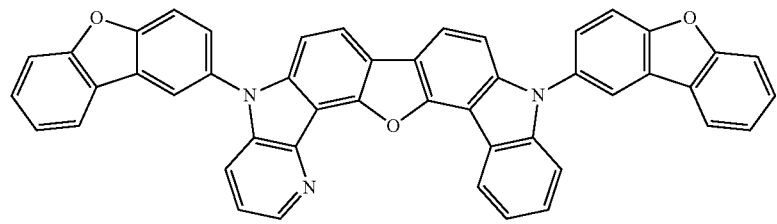
(44)
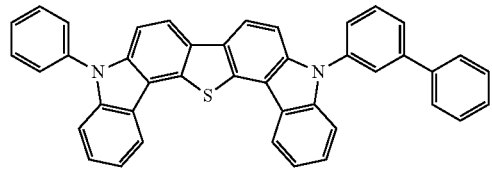
(45)
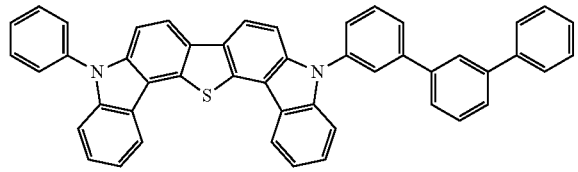
(46)
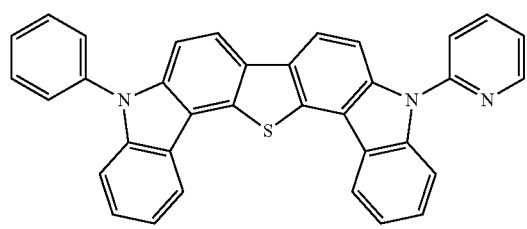
(47)
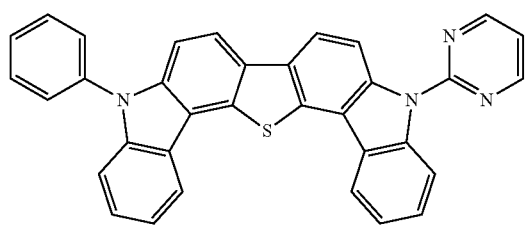
(48)
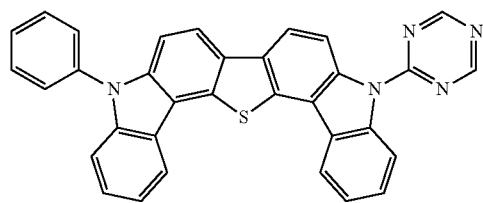
(49)
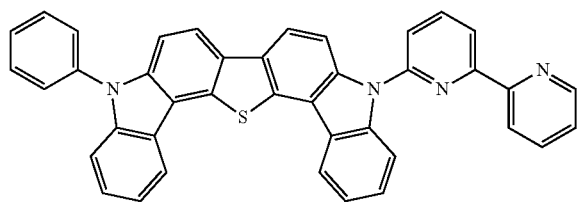
(50)
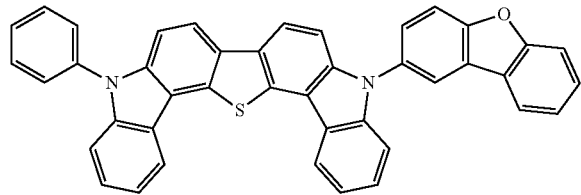
(51)
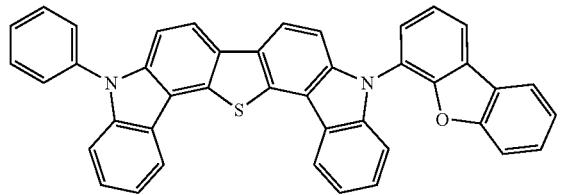
(52)
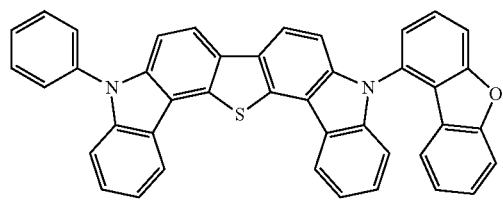
(53)
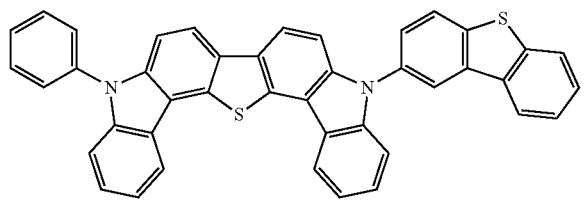
(54)
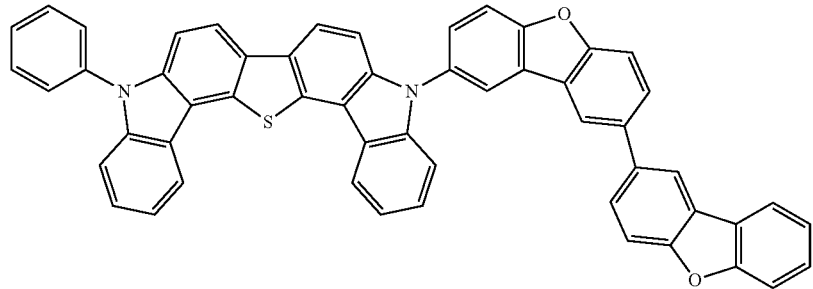
(55)

-continued
(56)
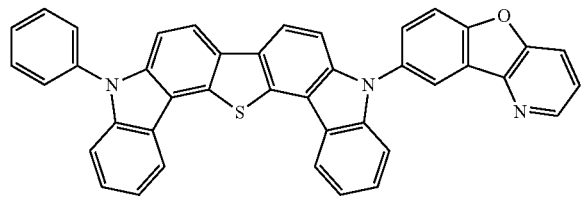
(57)
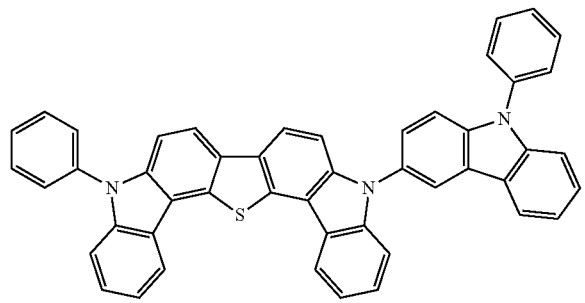
(58)
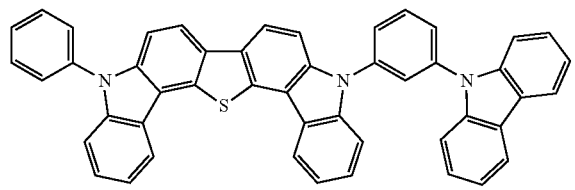
(59)
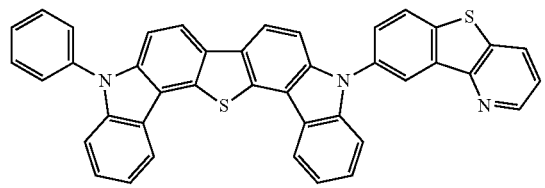
(60)
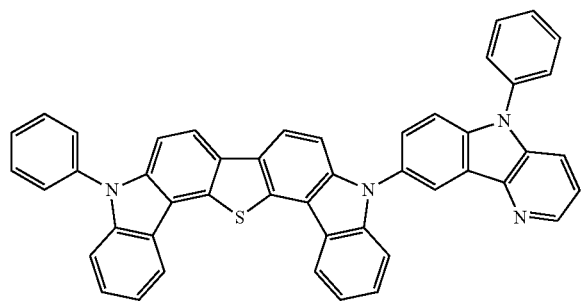
(61)
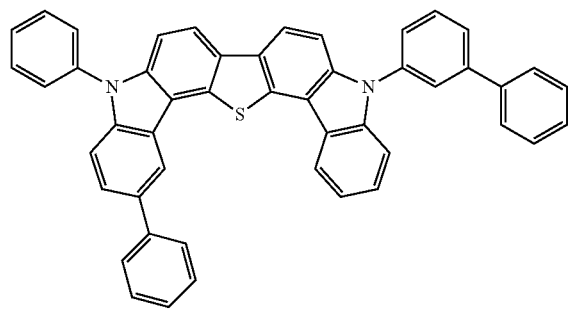
(62)
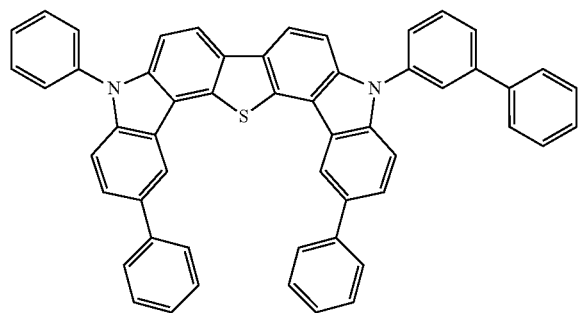
(63)
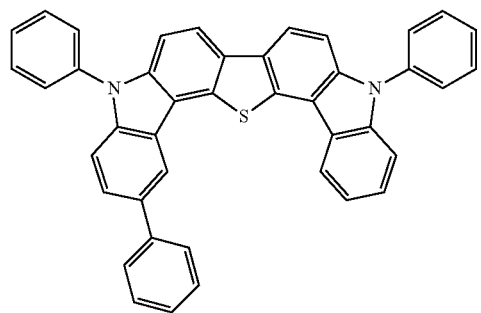
(64)
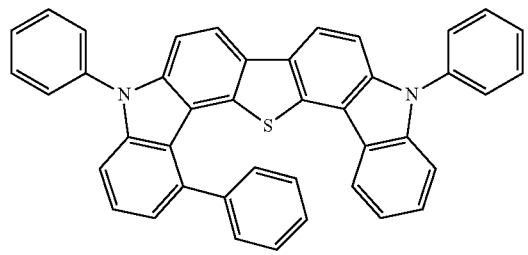
(65)
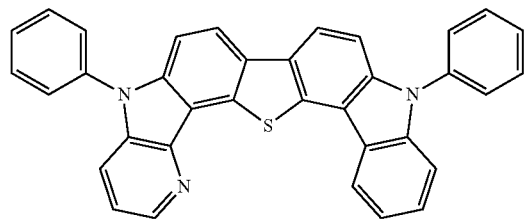

-continued
(66) 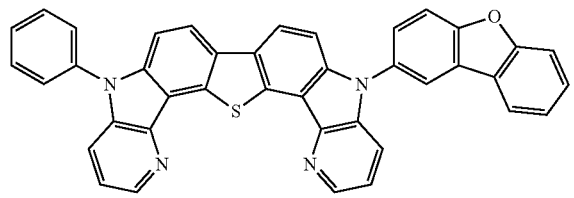
(67) 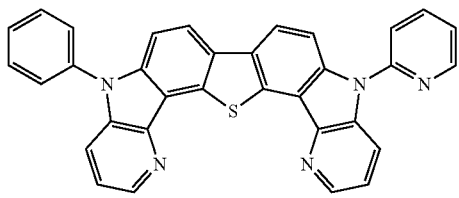
(68) 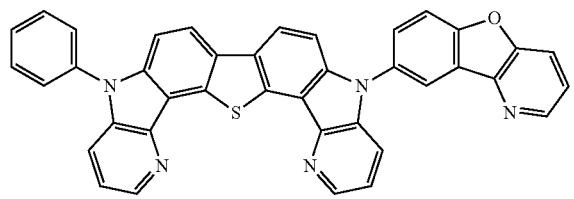
(69) 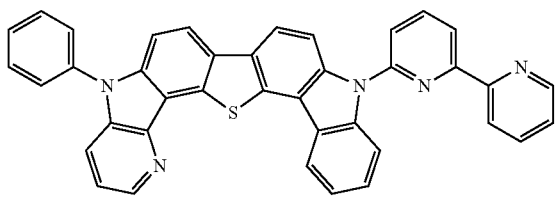
(70) 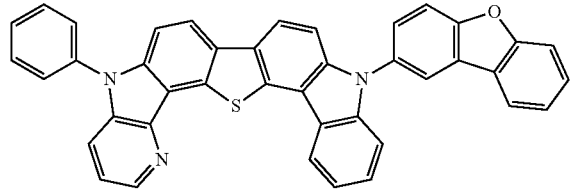
(71) 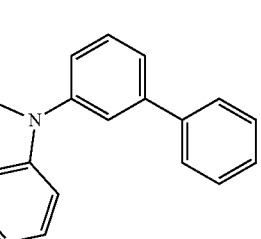
(72) 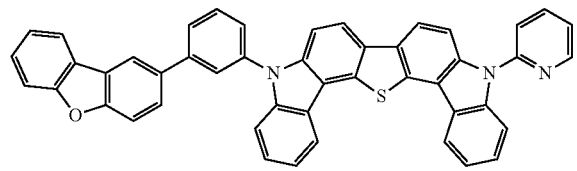
(73) 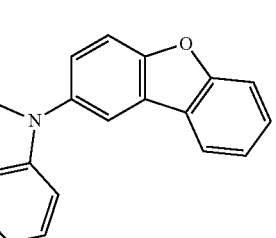
(74) 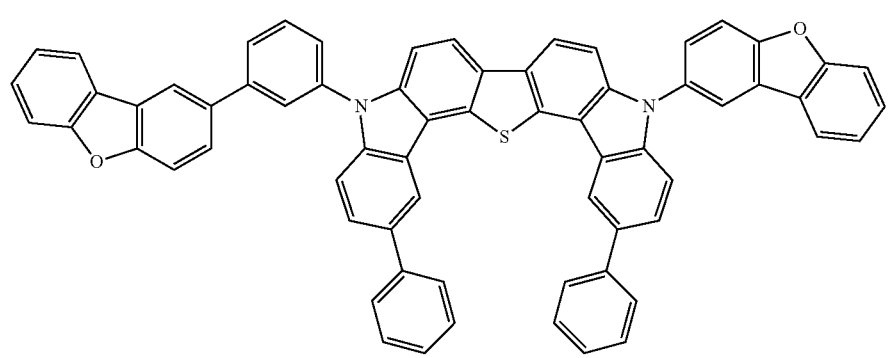

-continued
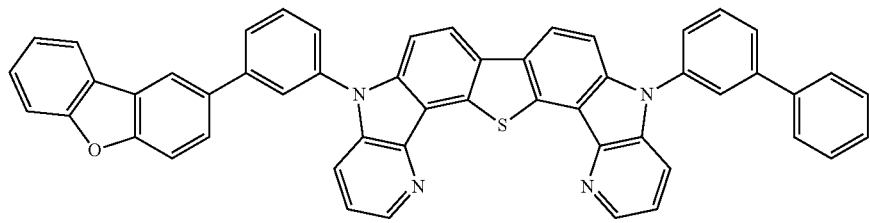
(75)
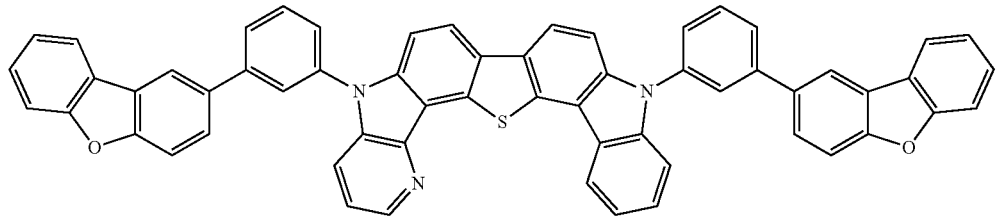
(76)
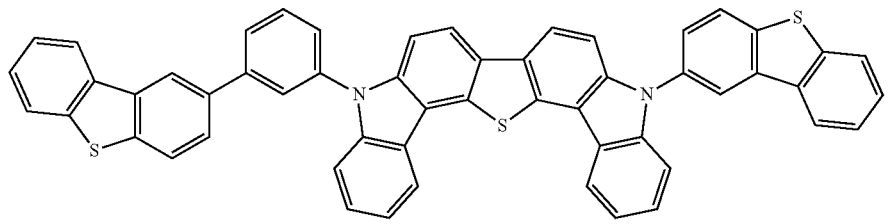
(77)
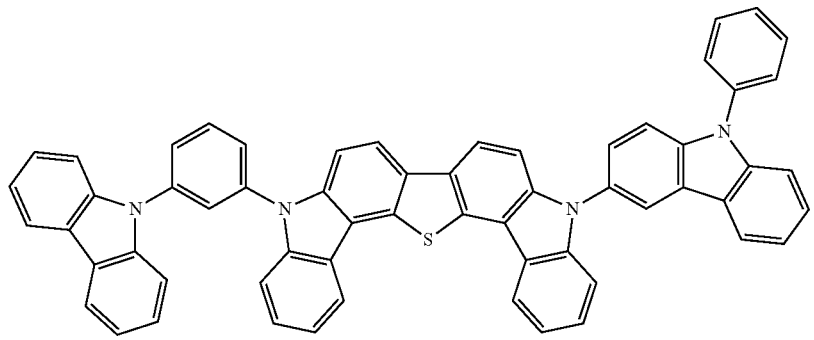
(78)
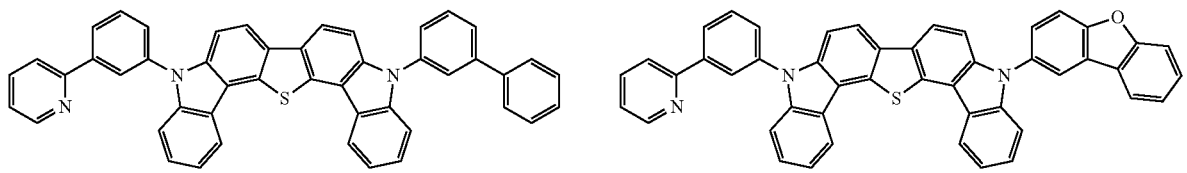
(79) (80)
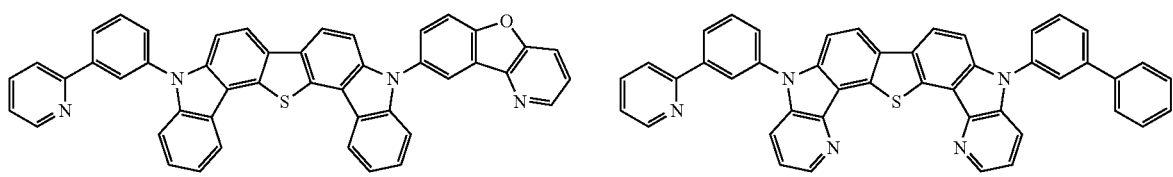
(81) (82)
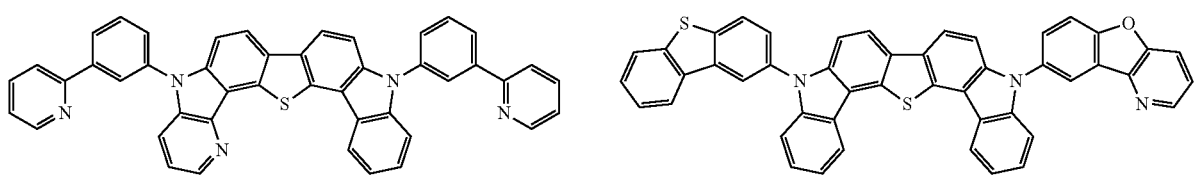
(83) (84)

-continued
(85)
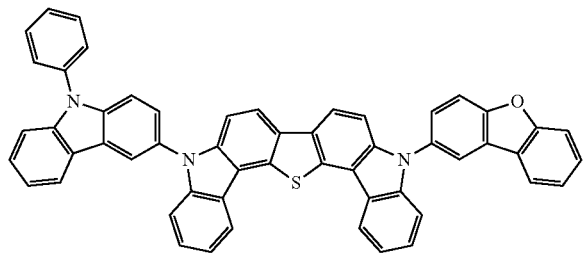
(86)
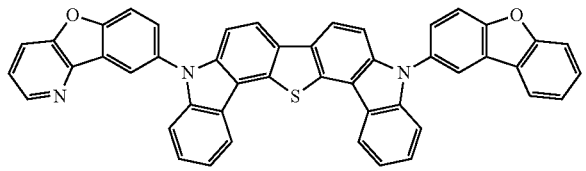
(87)
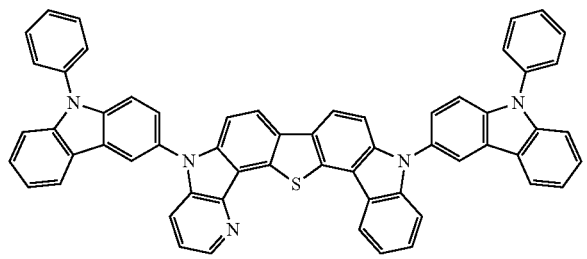
(88)
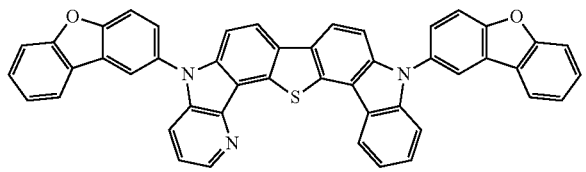
(89)
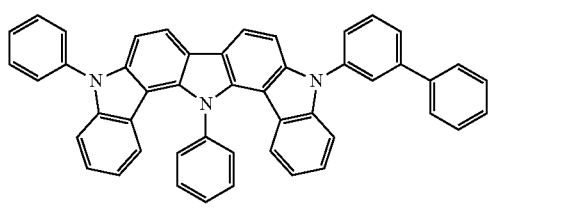
(90)
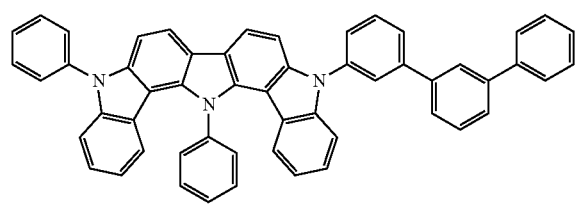
(91)
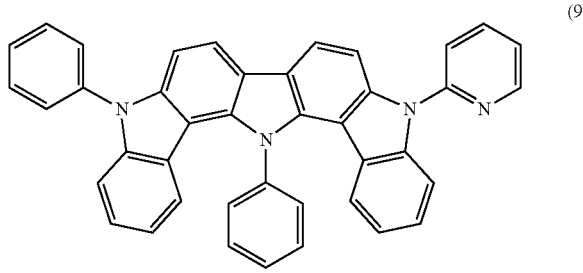
(92)
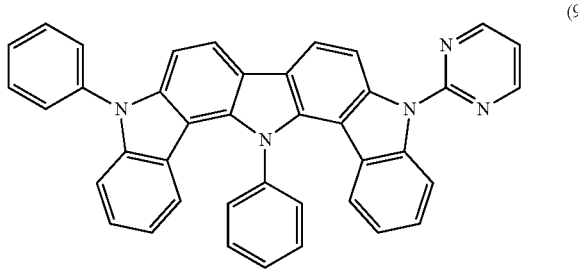
(93)
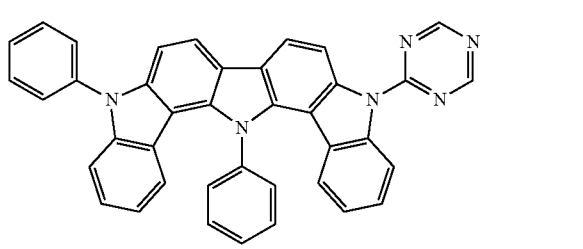
(94)
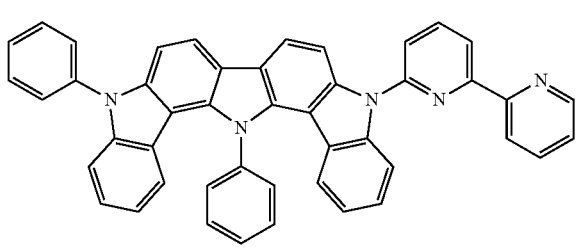
(95)
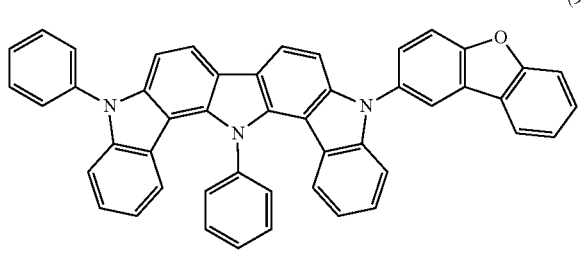
(96)
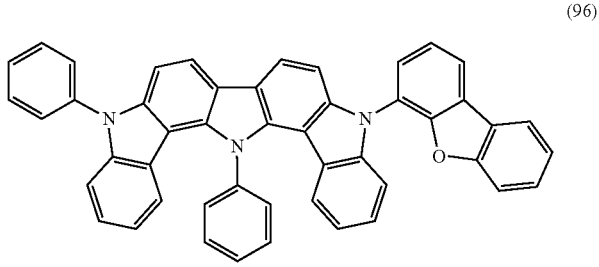

-continued
(97)
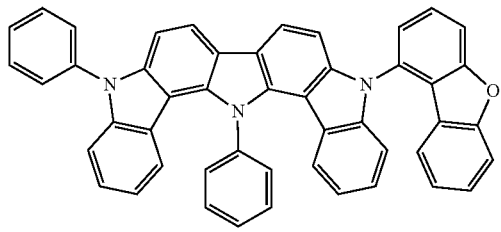
(98)
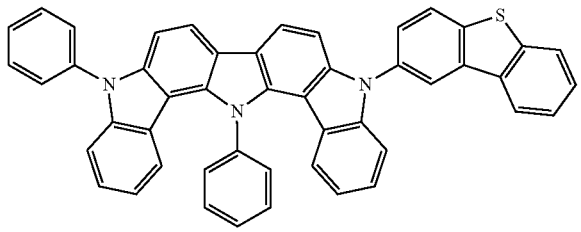
(99)
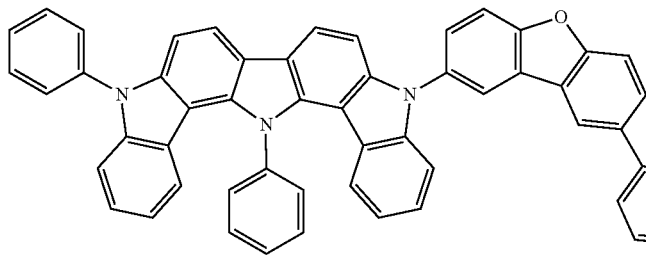
(100)
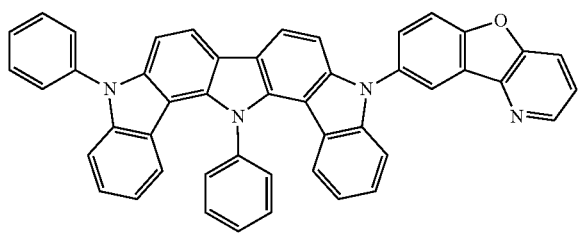
(101)
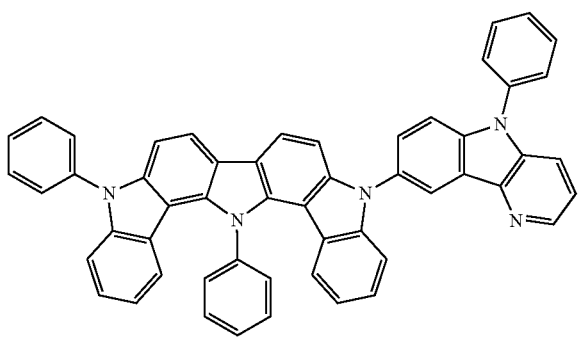
(102)
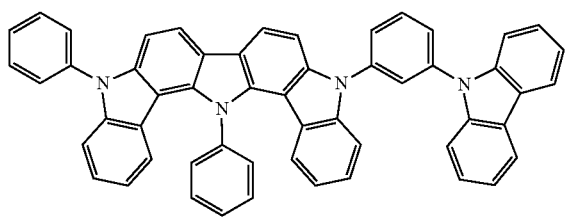
(103)
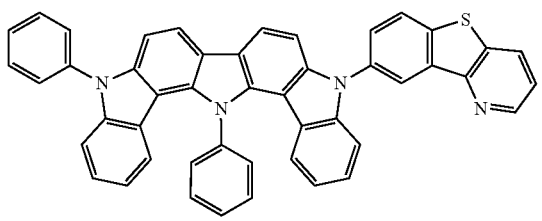
(104)
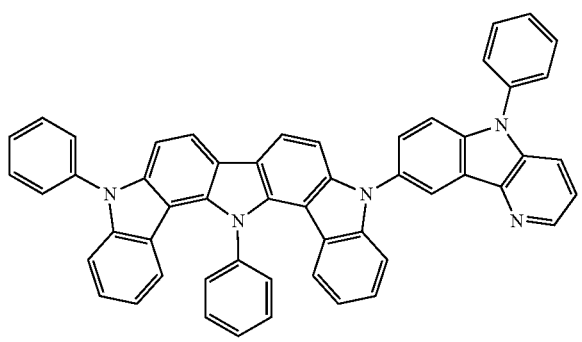
(105)
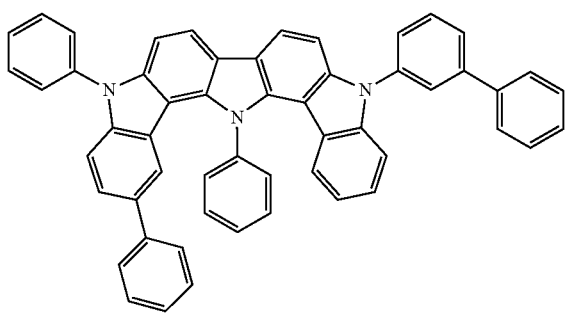

-continued
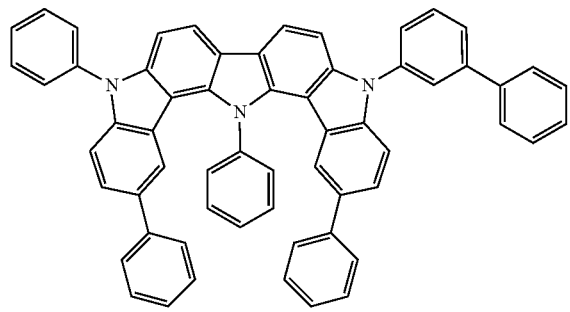
(106)
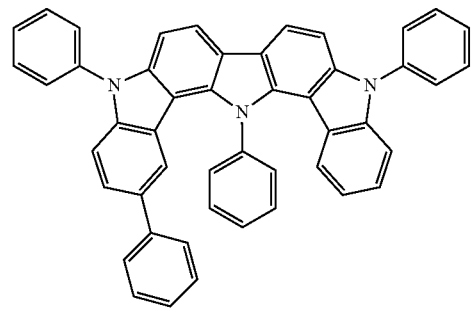
(107)
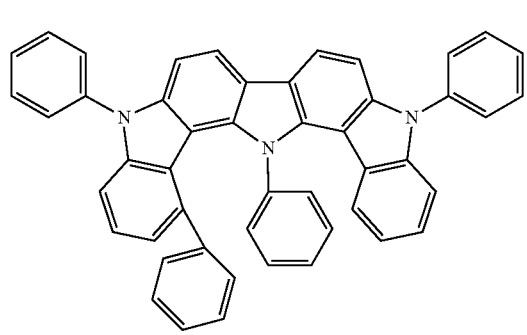
(108)
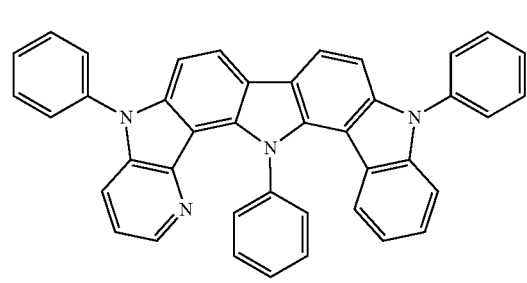
(109)
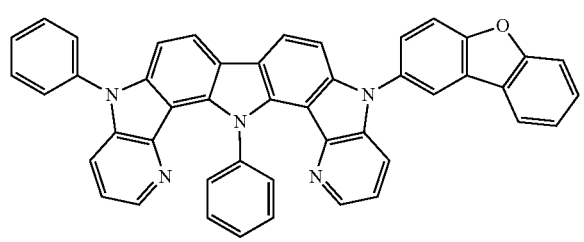
(110)
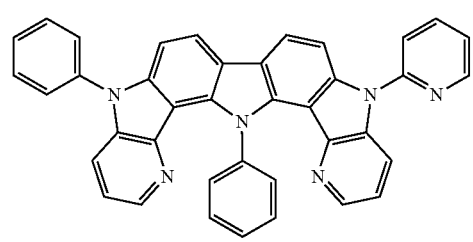
(111)
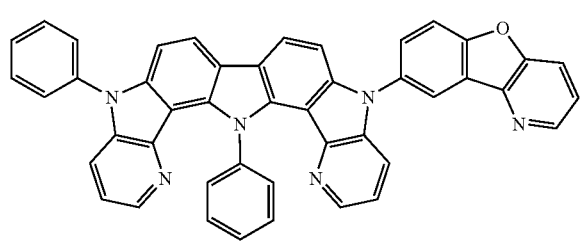
(112)
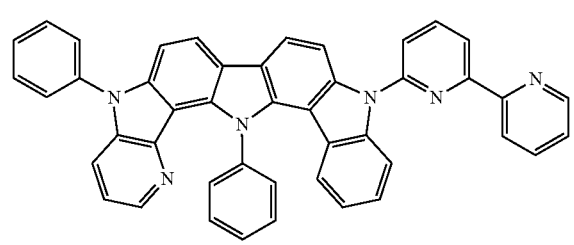
(113)
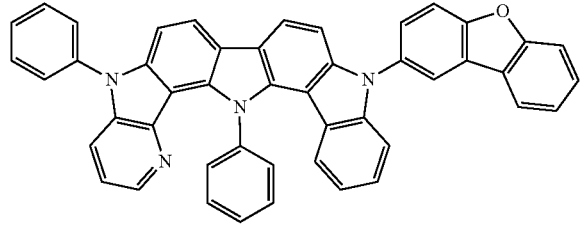
(114)

(115)
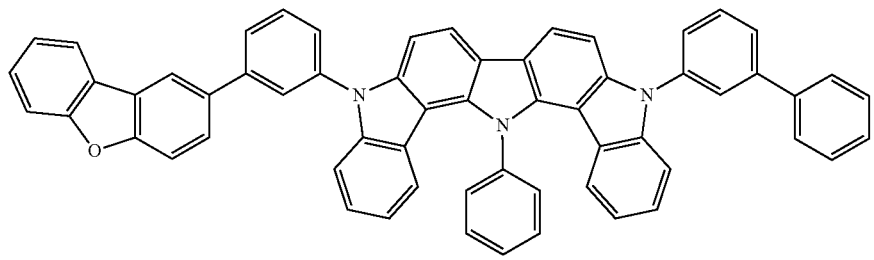
(116)
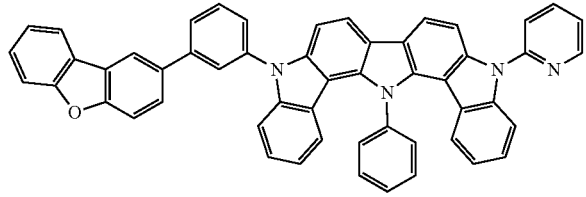
(117)
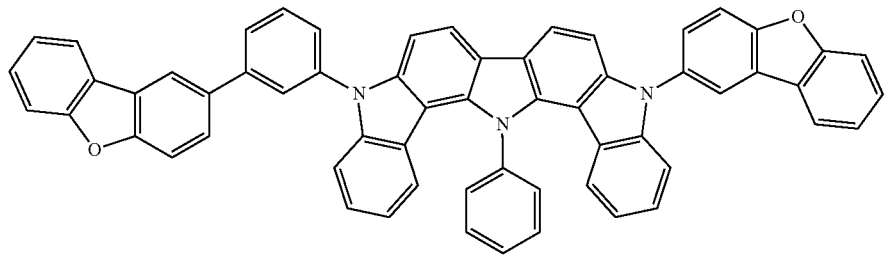
(118)
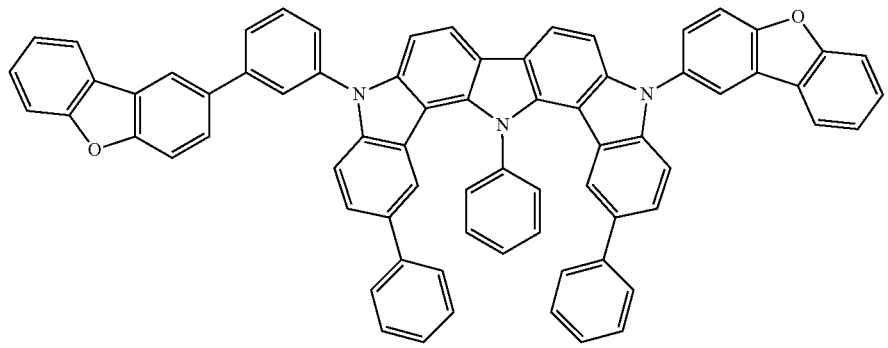
(119)
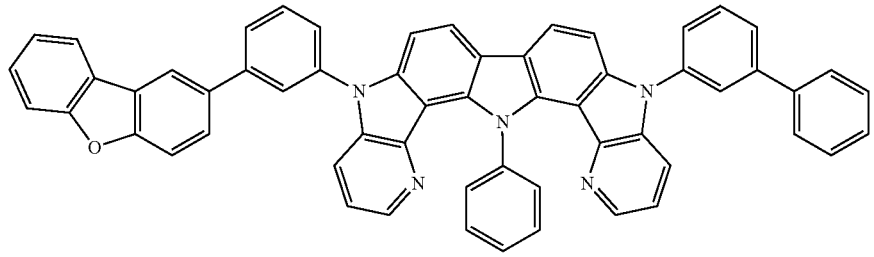
(120)
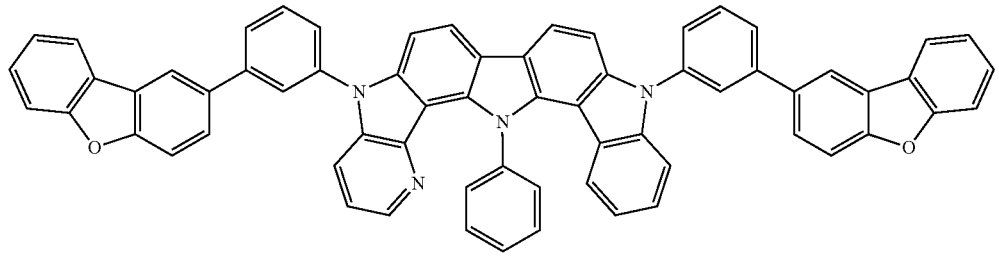

-continued
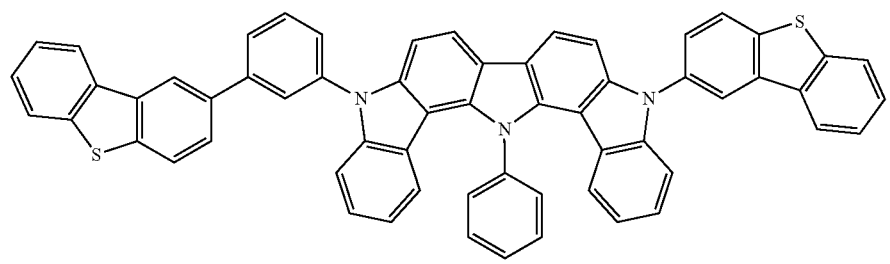
(121)
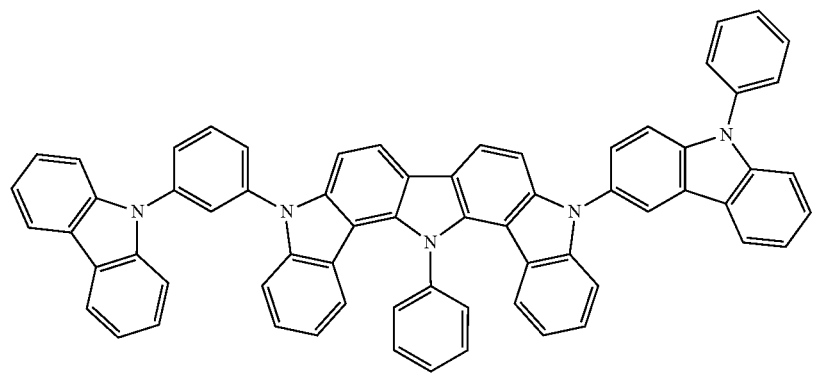
(122)
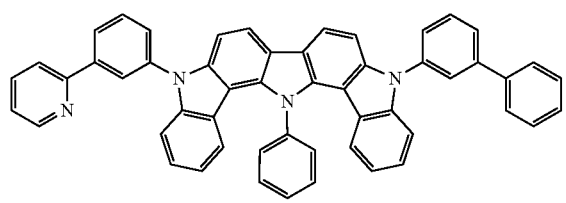
(123)
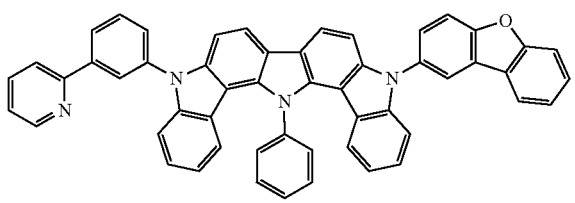
(124)
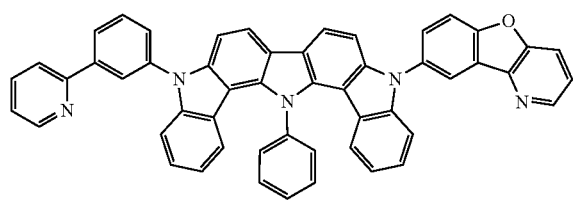
(125)
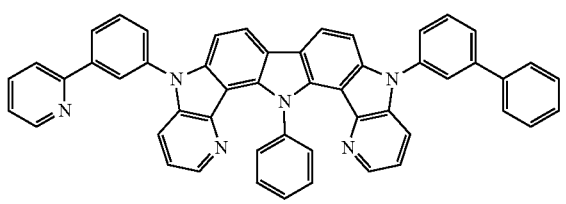
(126)
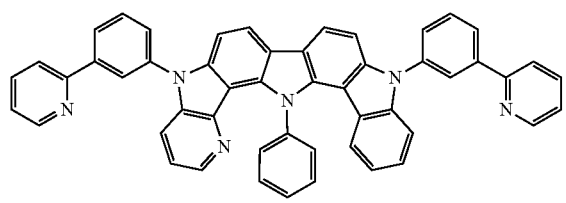
(127)
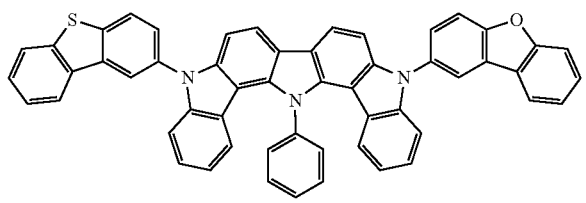
(128)
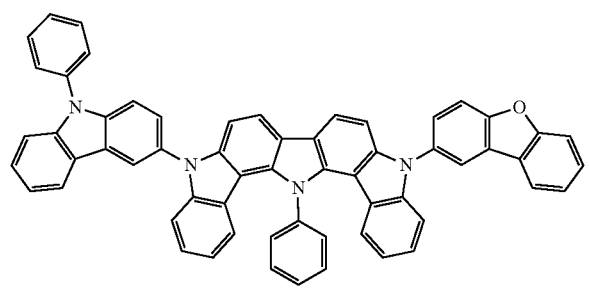
(129)
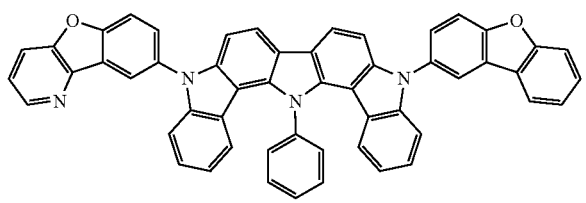
(130)

-continued
(131)
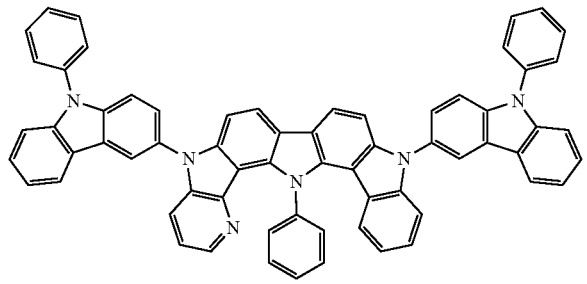
(132)
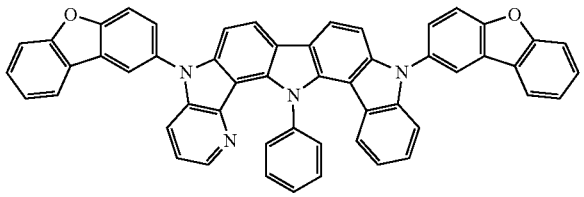
(133)
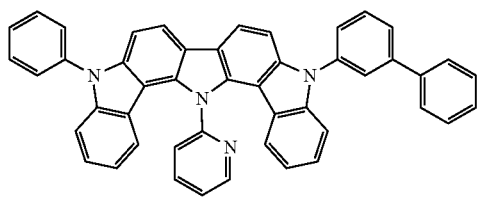
(134)
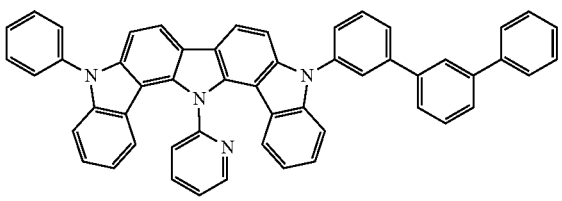
(135)
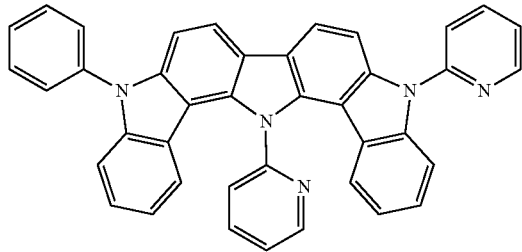
(136)
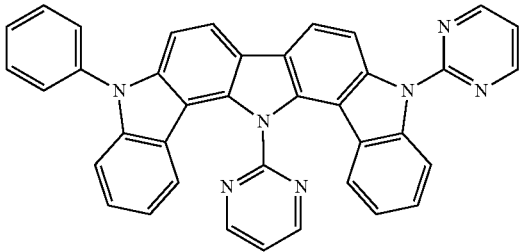
(137)
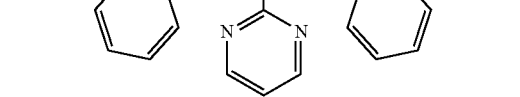
(138)
(139)
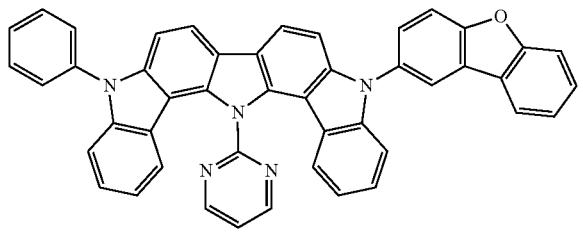
(140)
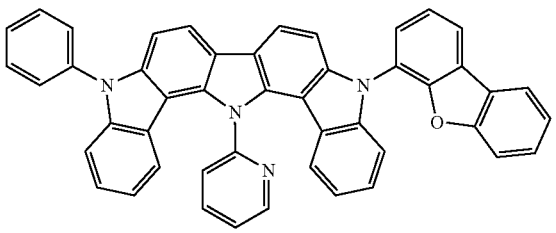
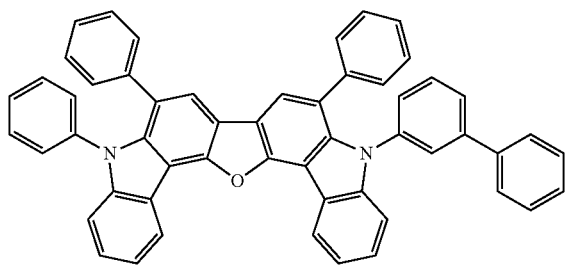
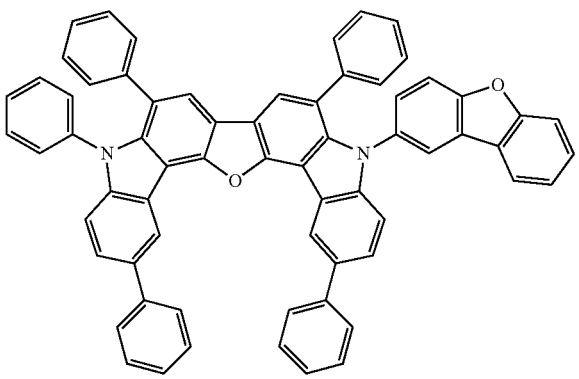

-continued
(141)
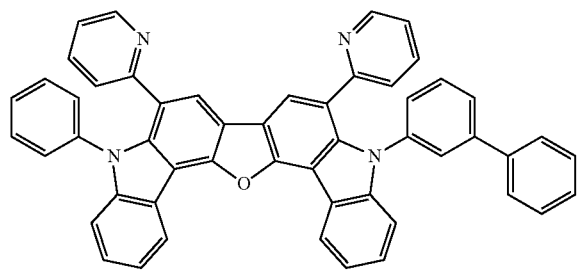
(142)
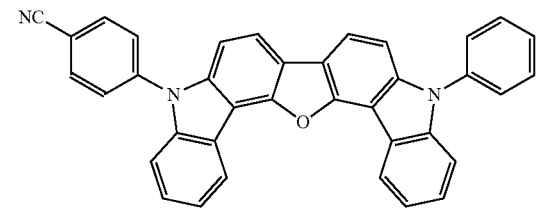
(143)
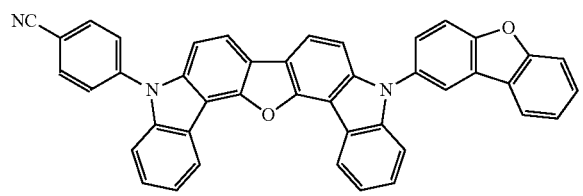
(144)
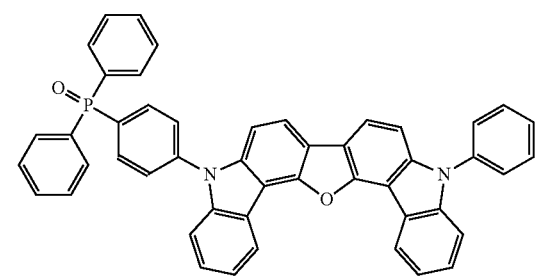
(145)
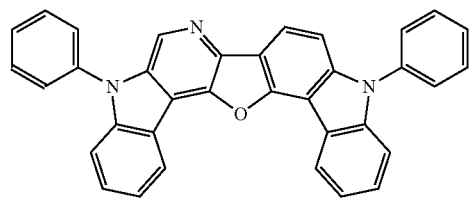
(146)
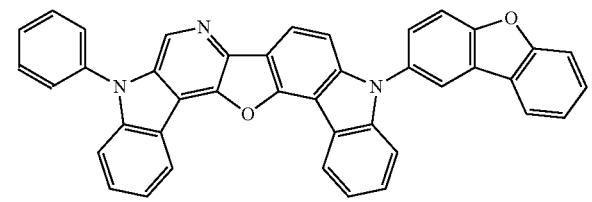
(147)
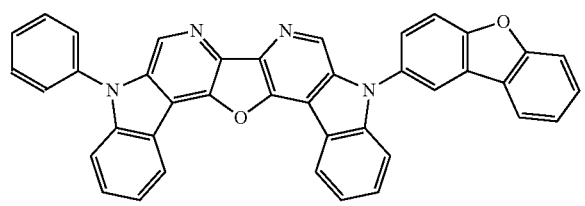
(151)
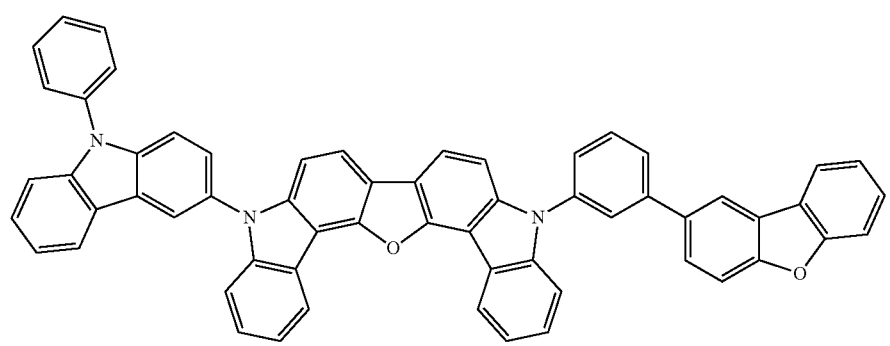

-continued
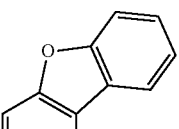
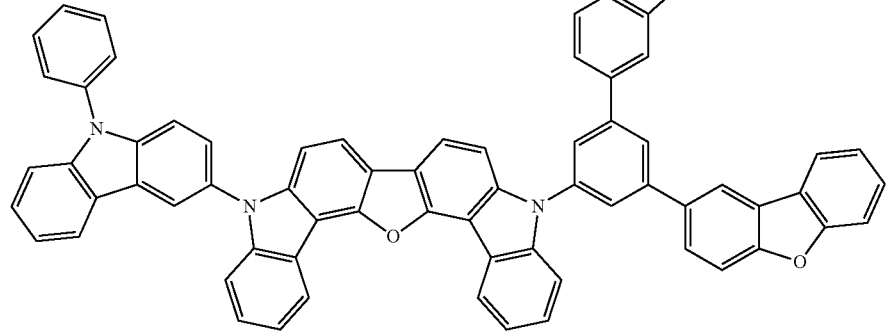
(152)
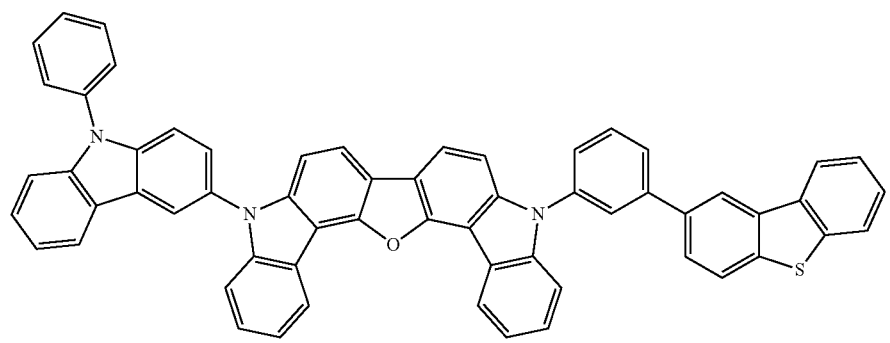
(153)
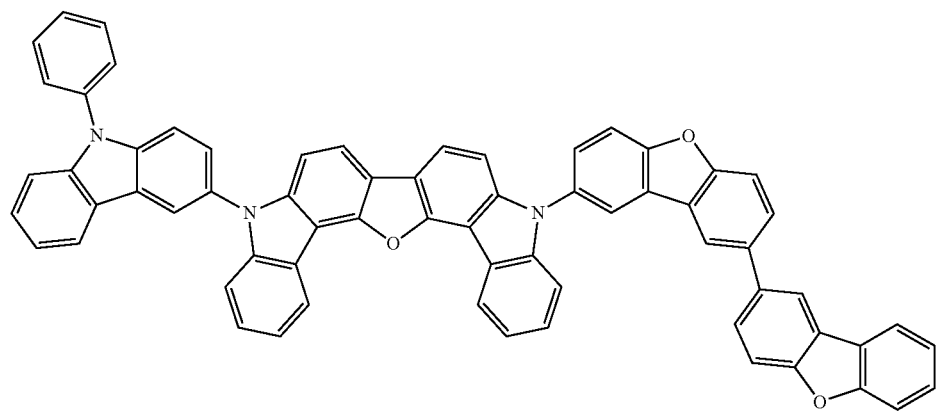
(154)
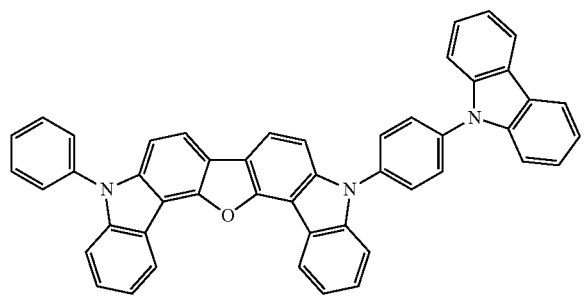
(155)

-continued
(156)
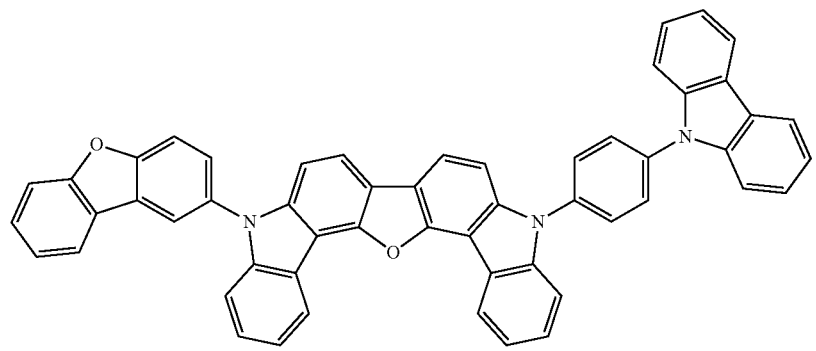
(157)
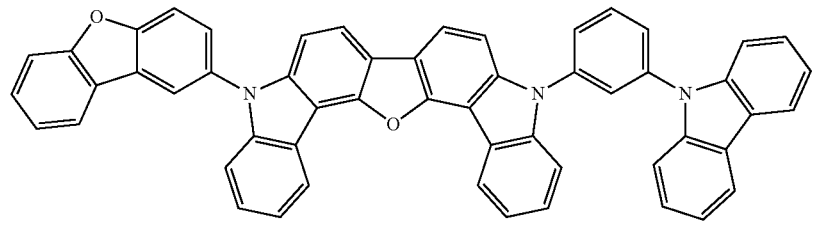
(158)
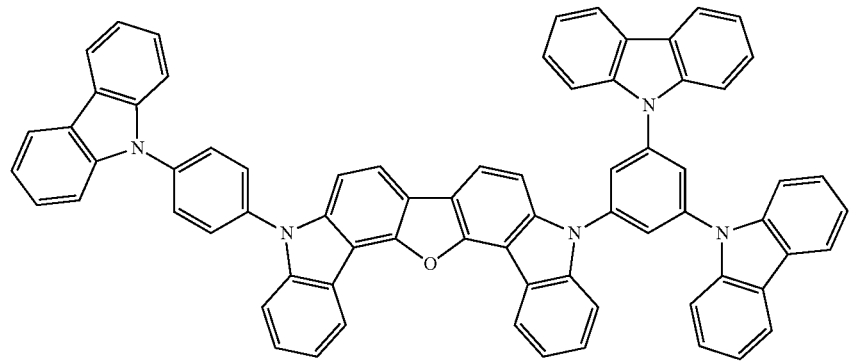
(159) (160)
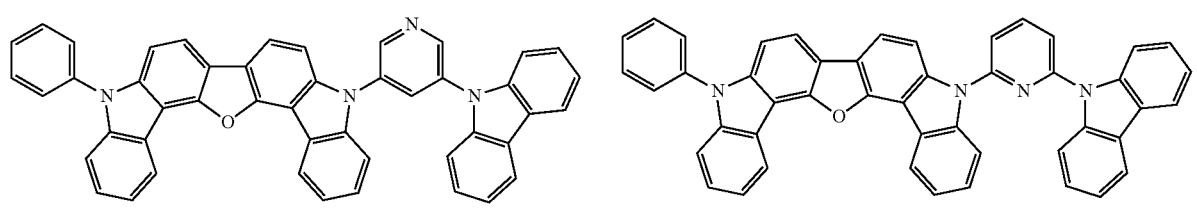
(161) (162)
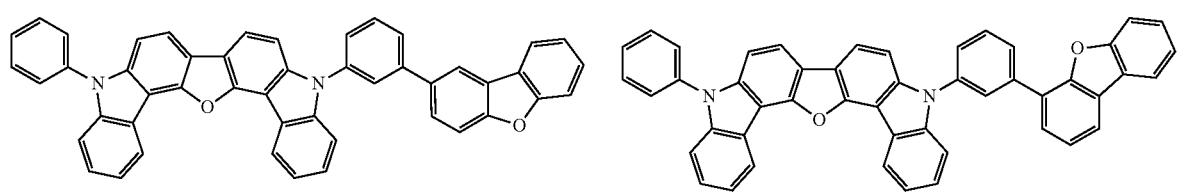
(163)
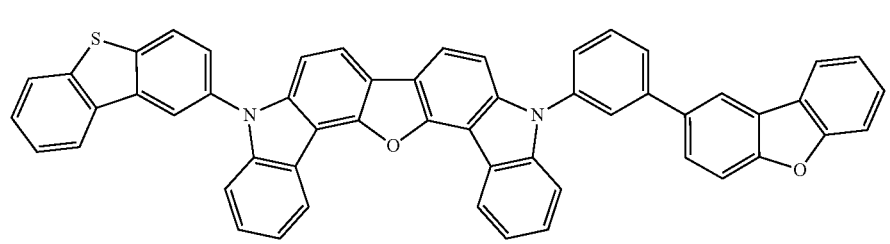

-continued
(164)
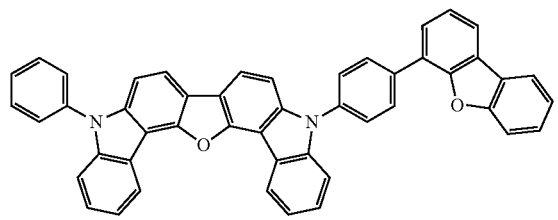
(165)
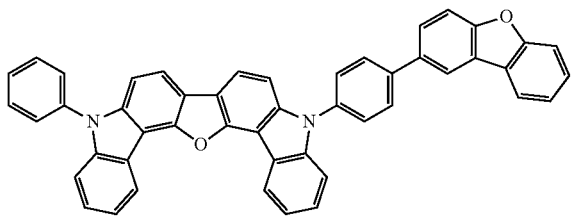
(166)
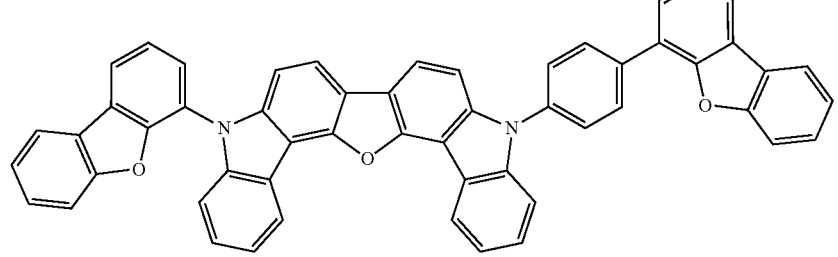
(167)
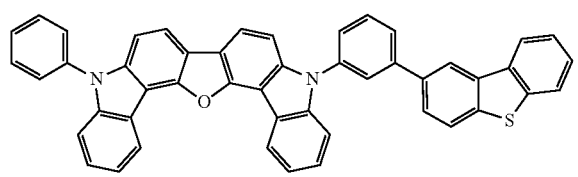
(168)
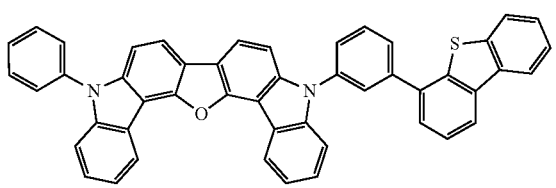
(169)
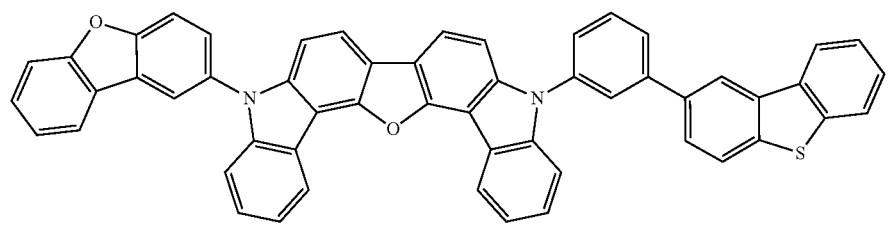
(170)
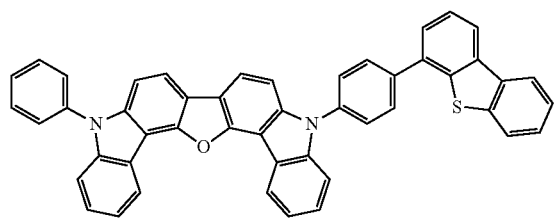
(171)
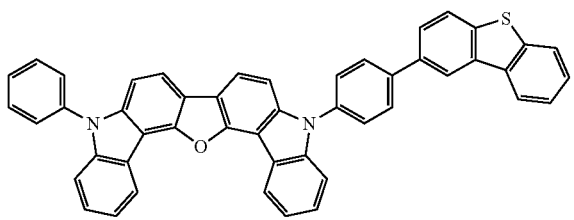
(172)
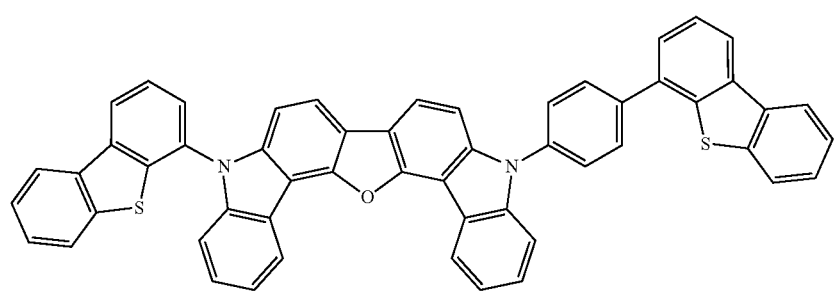

-continued
(173)
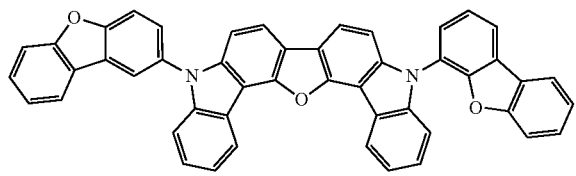
(174)
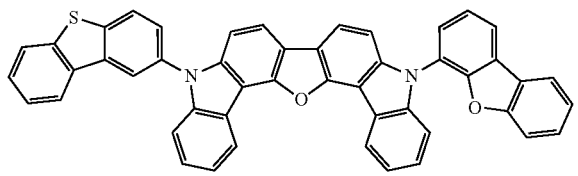
(175)
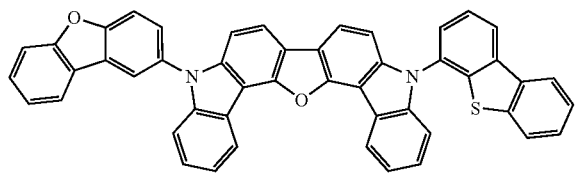
(176)
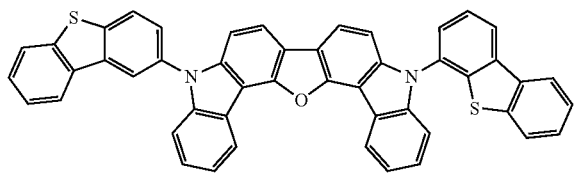
(177)
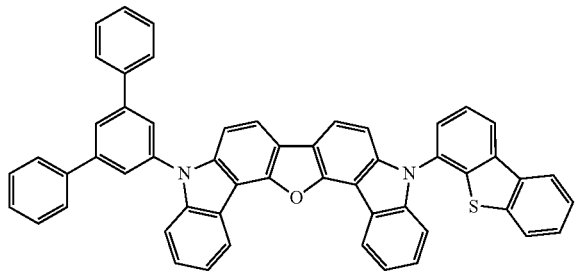
(178)
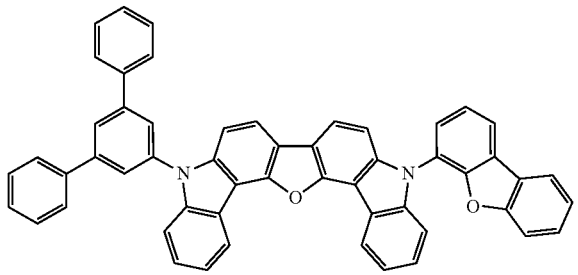
(179)
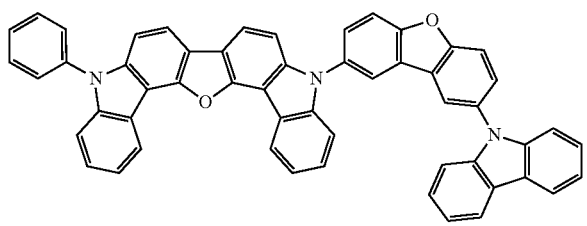
(180)
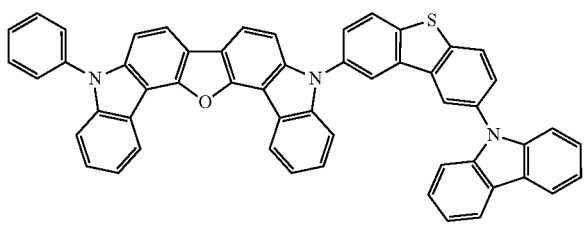
(181)
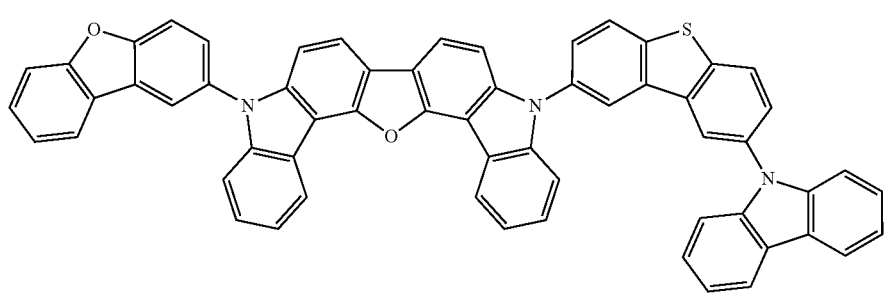
(182)
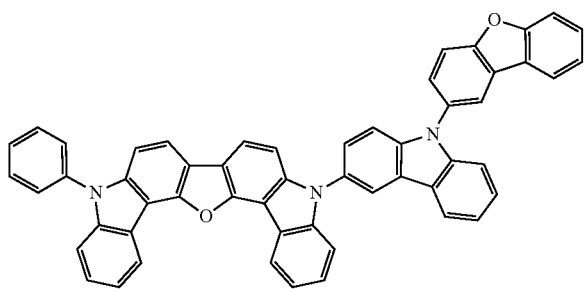
(183)
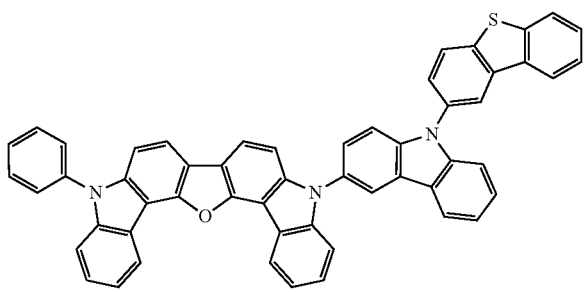

-continued
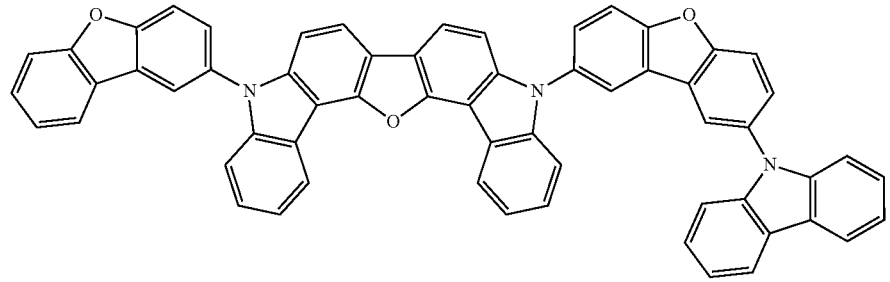
(184)
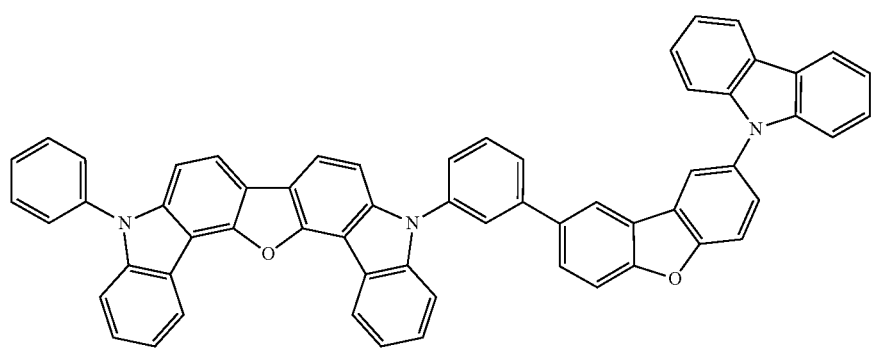
(185)
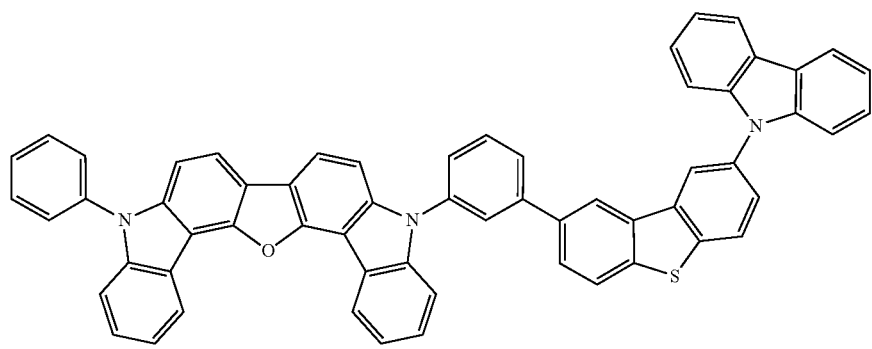
(186)
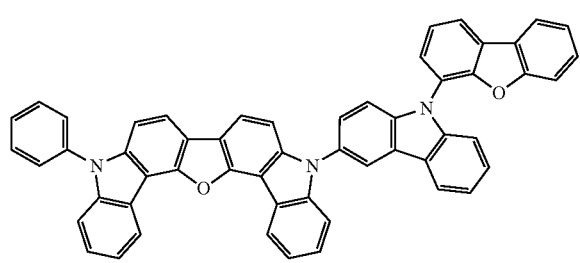
(187)
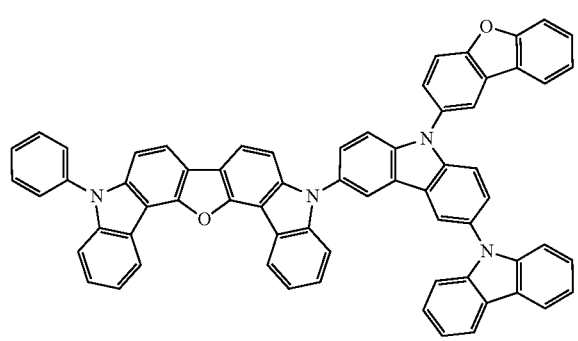
(188)

-continued
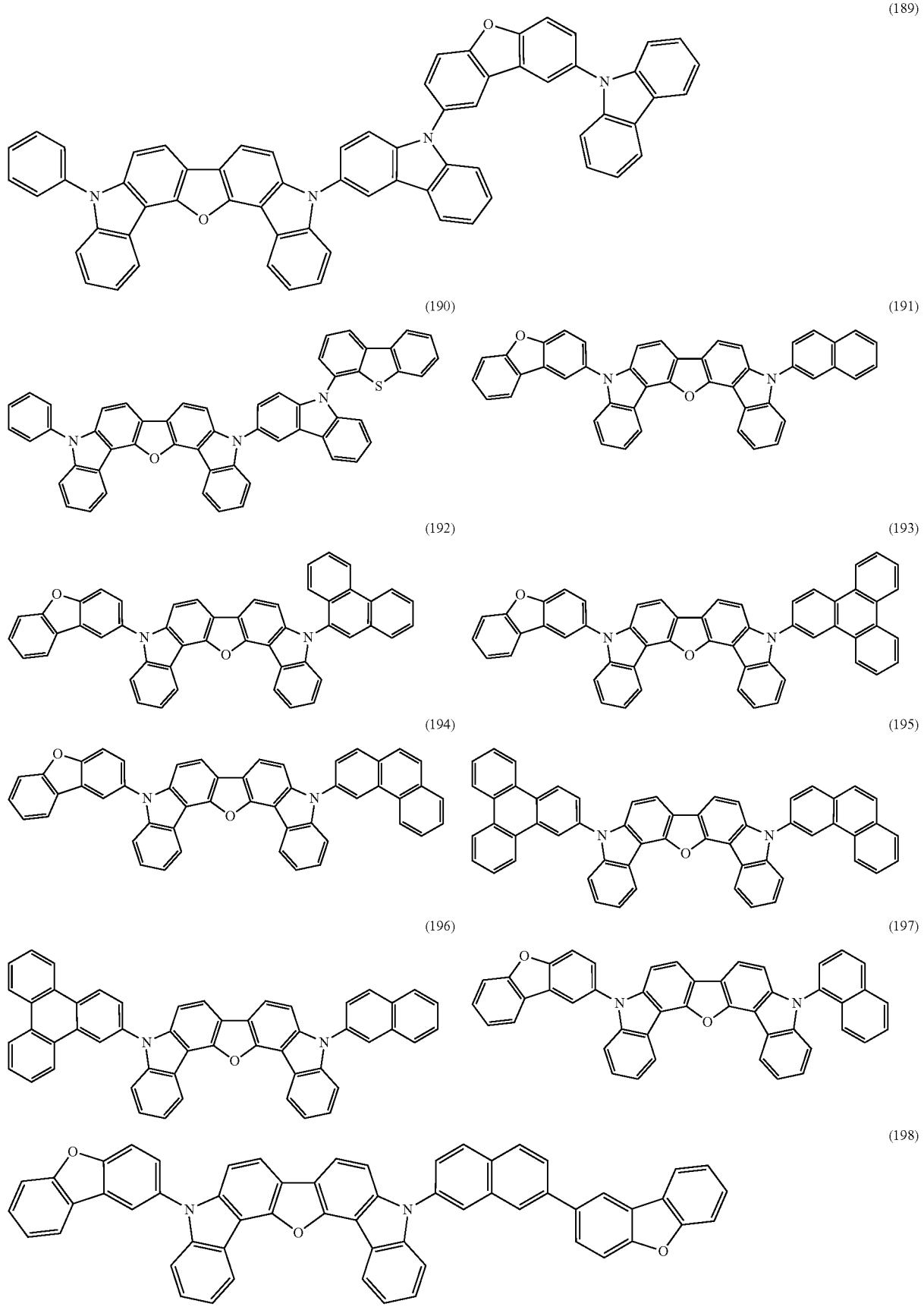

-continued
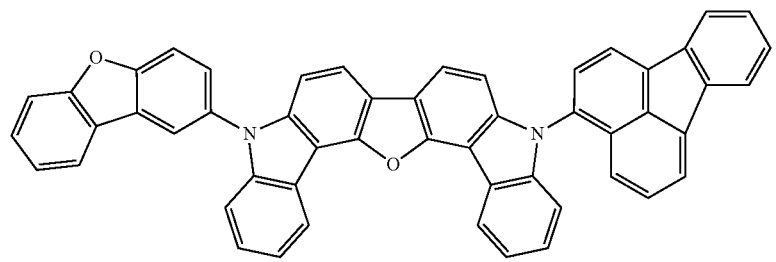
(199)
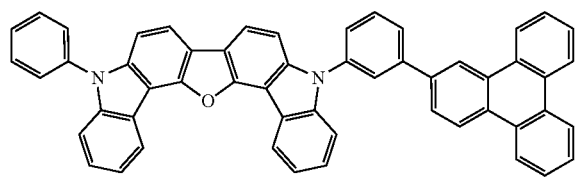
(200)
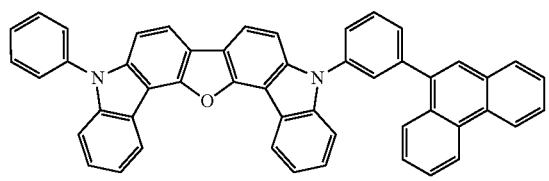
(201)
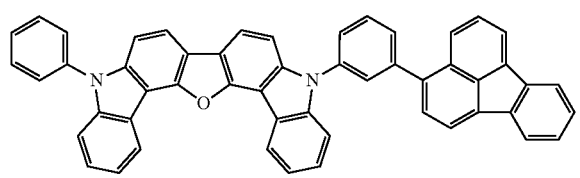
(202)
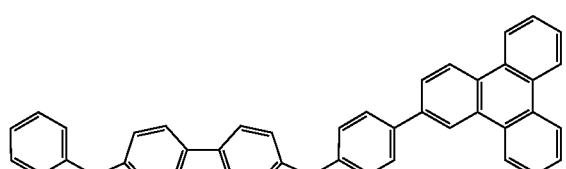
(203)
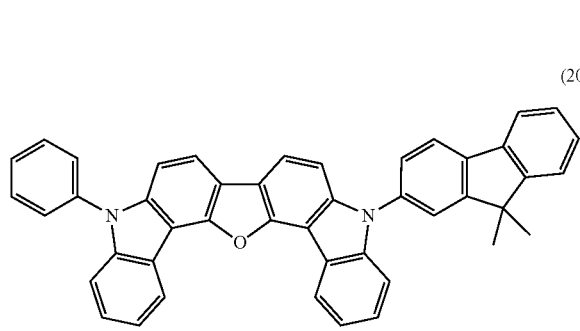
(204)
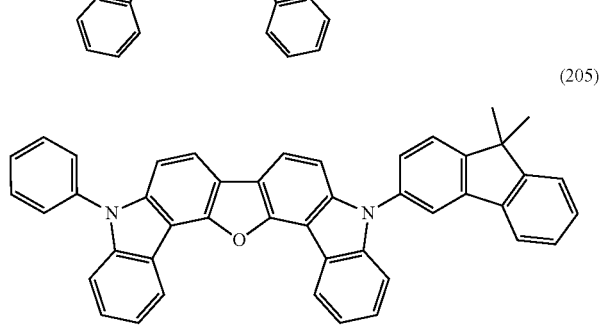
(205)
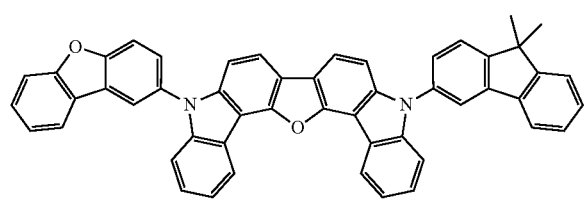
(206)
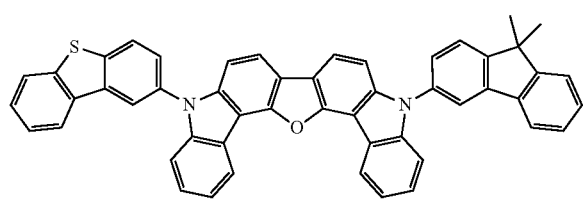
(207)
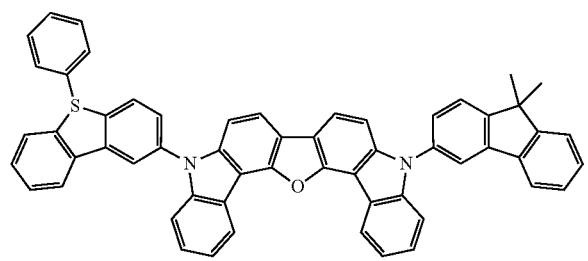
(208)
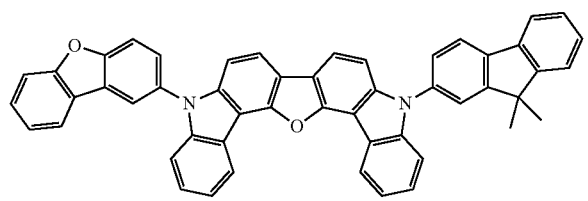
(209)

-continued
(210)
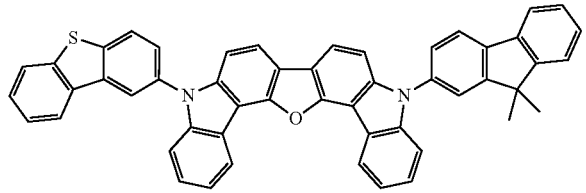
(211)
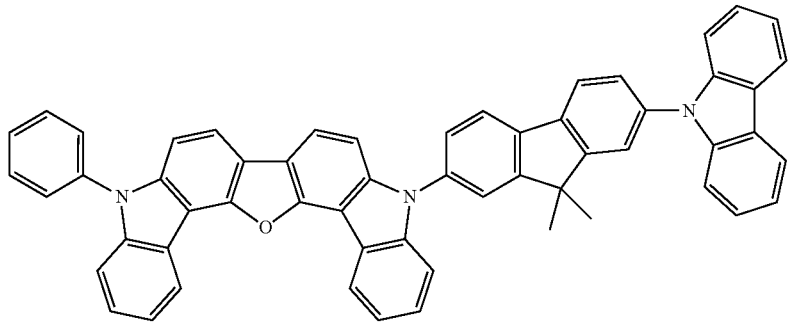
(212) (213)
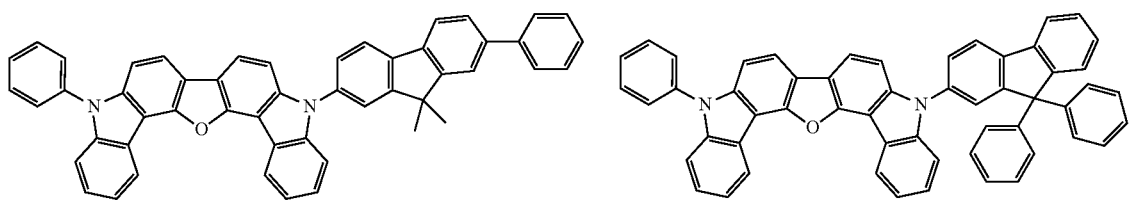
(214)
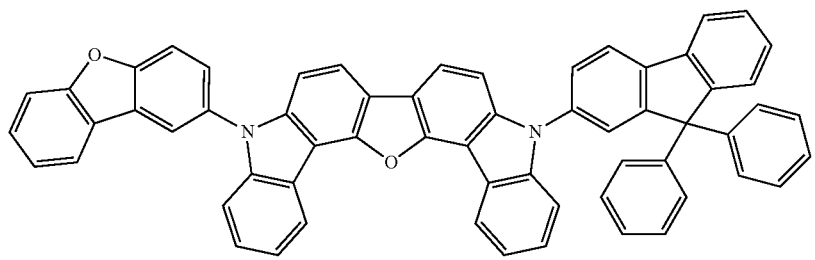
(215)
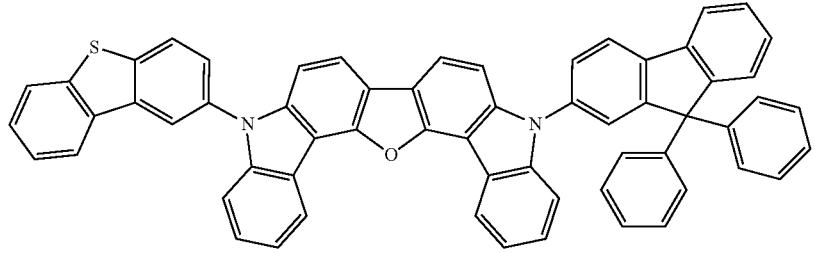
(216)
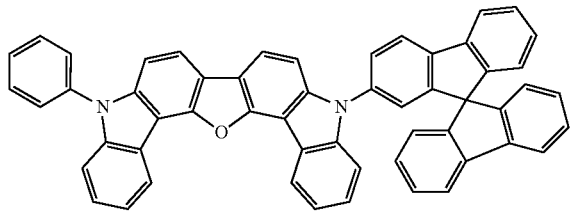

(217)
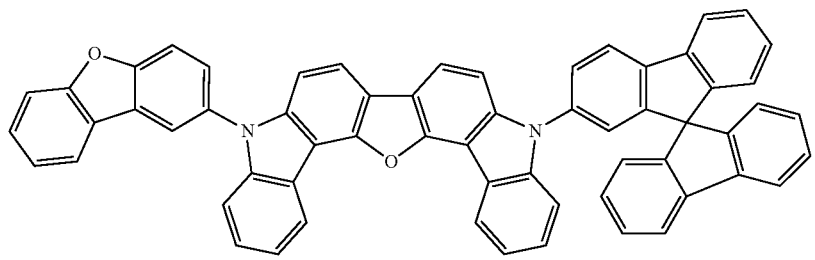
(218)
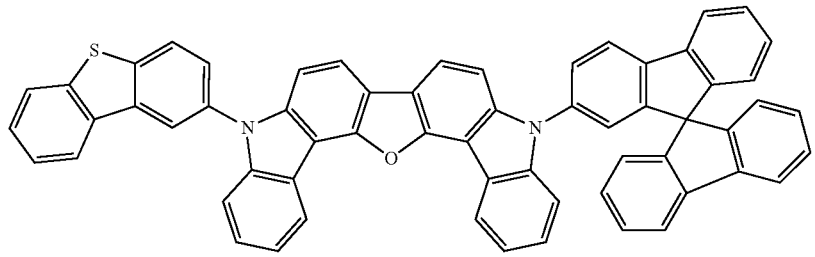
(219)
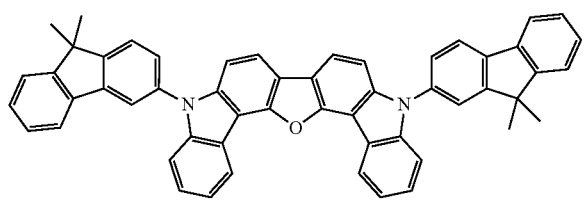
(220)
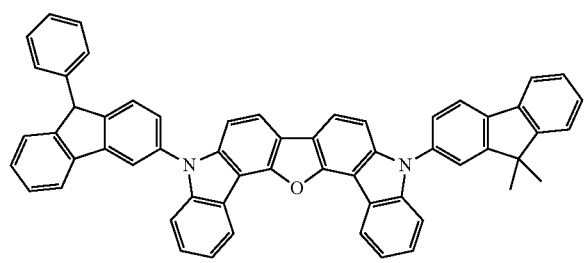
(221)
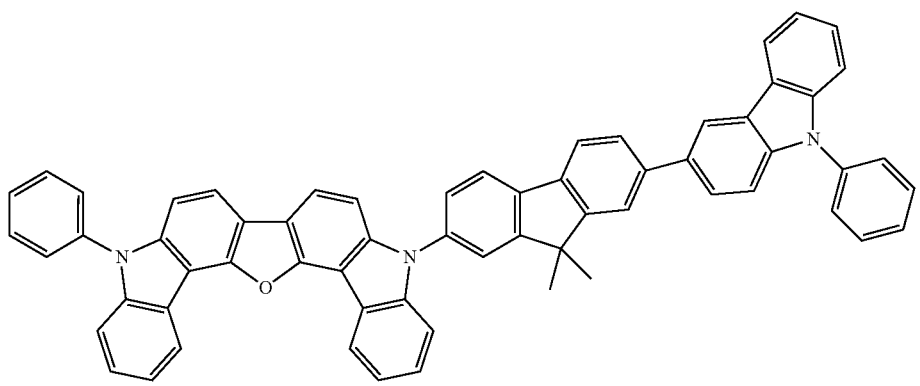
(222)
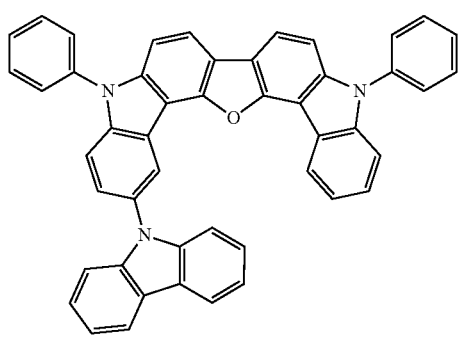
(223)
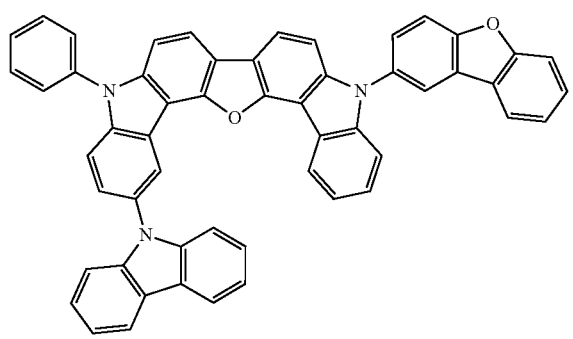

(224) 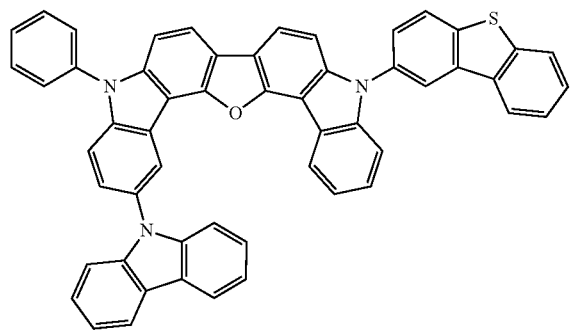
(225) 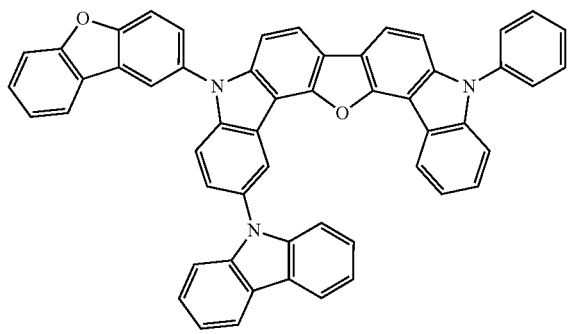
(226) 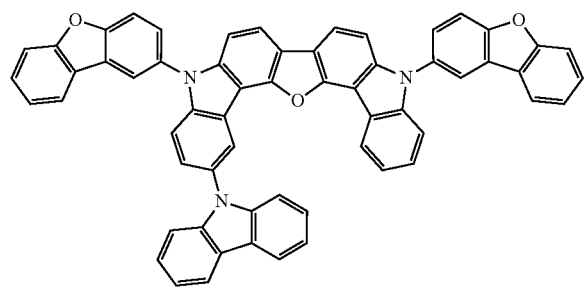
(227) 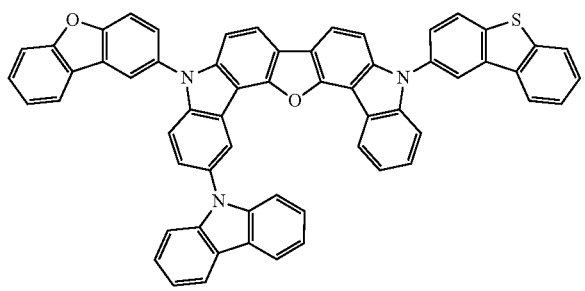
(228) 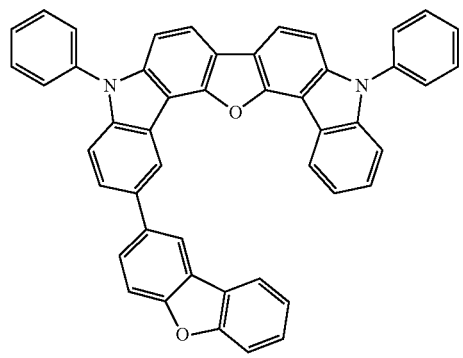
(229) 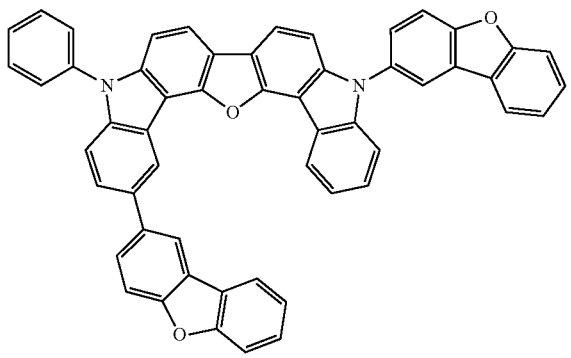
(230) 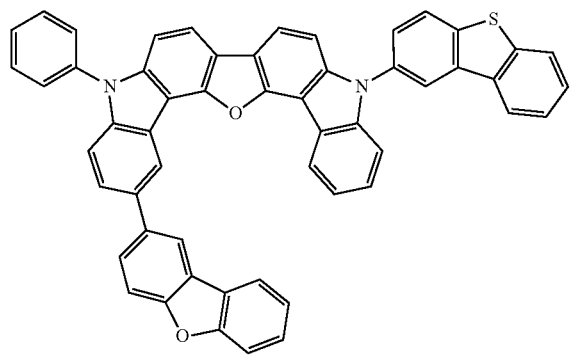
(231) 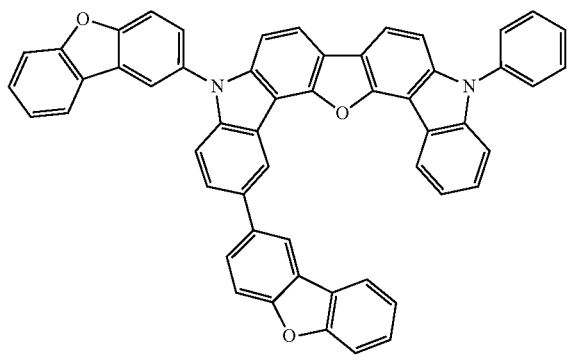

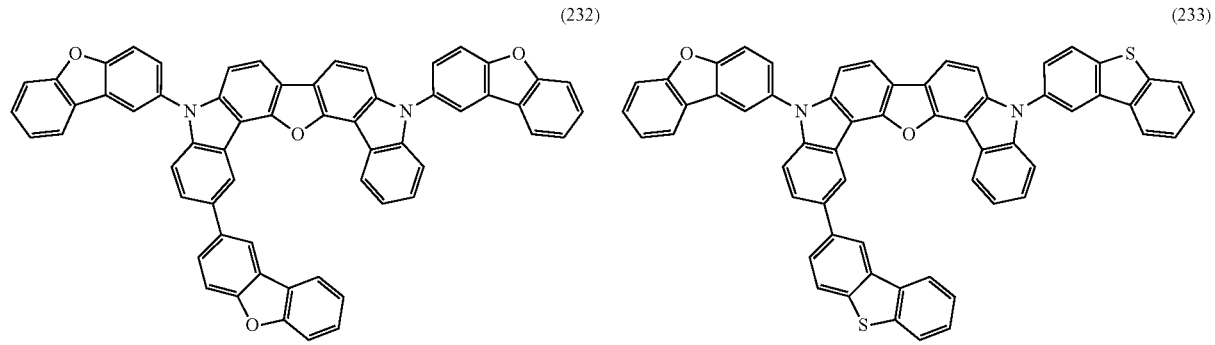
(232) (233)
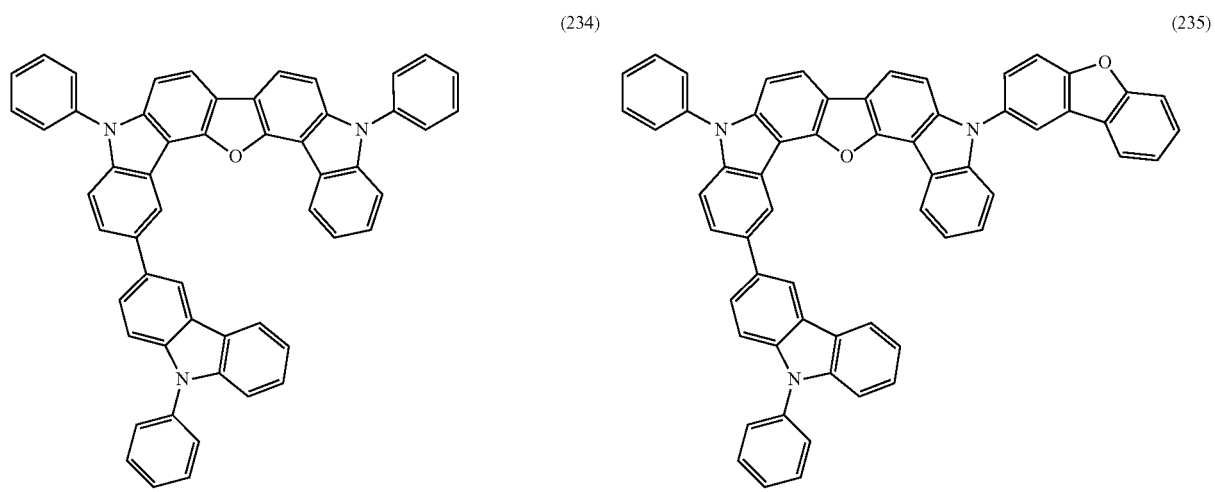
(234) (235)
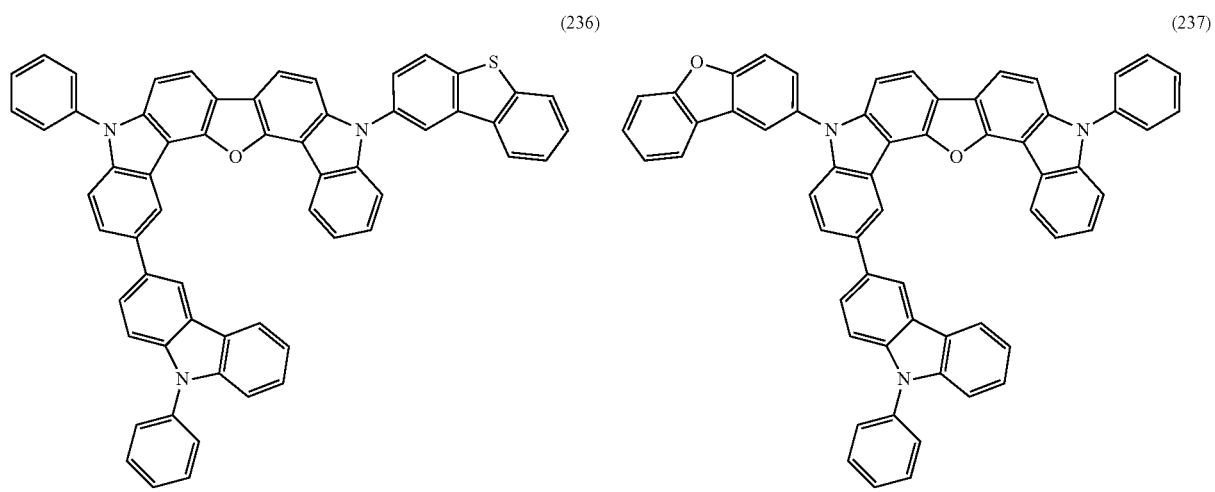
(236) (237)

-continued
(238)
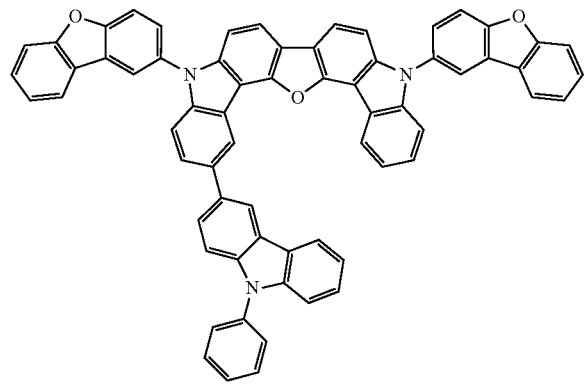
(239)
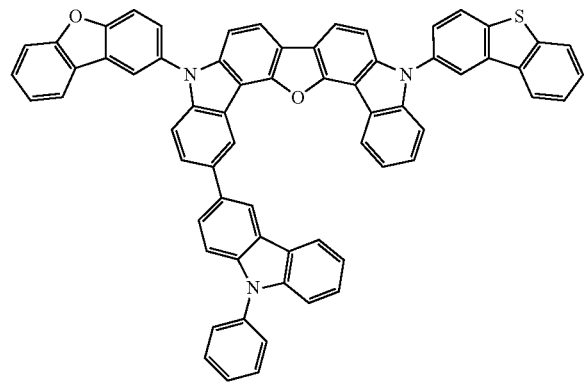
(240)
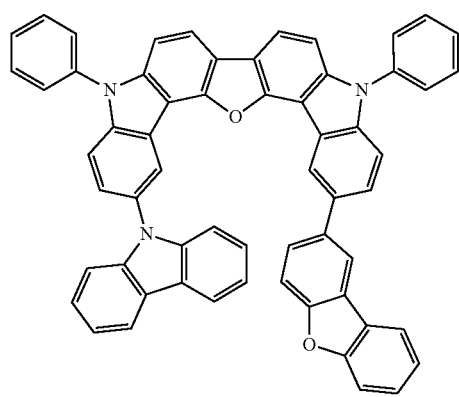
(241)
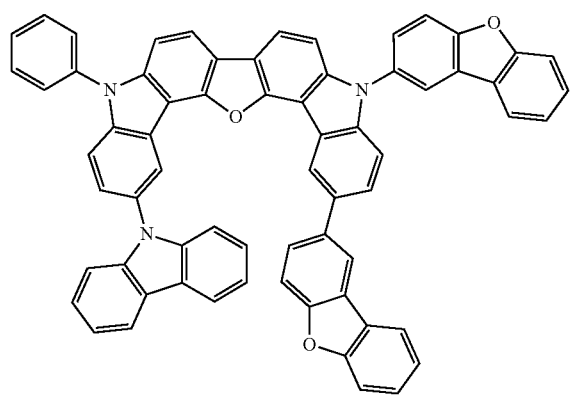
(242)
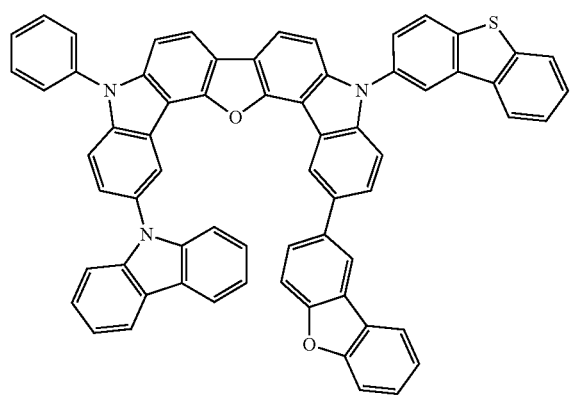
(243)
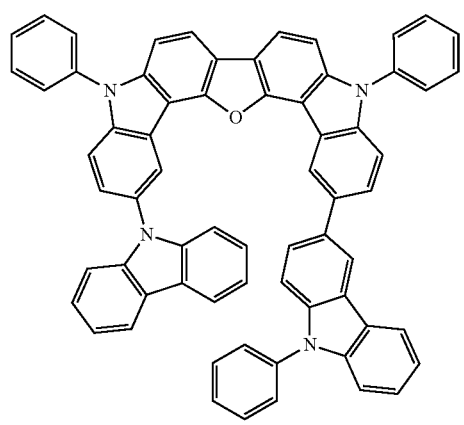

(244)
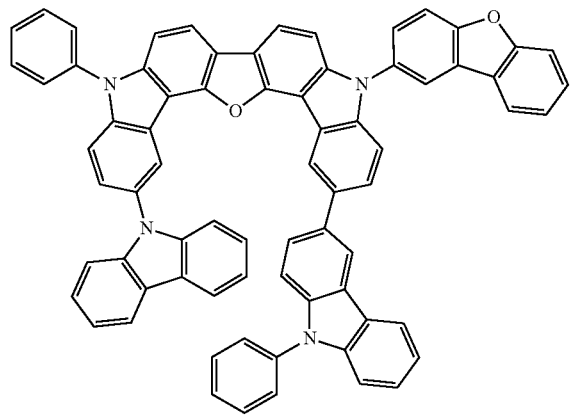
(245)
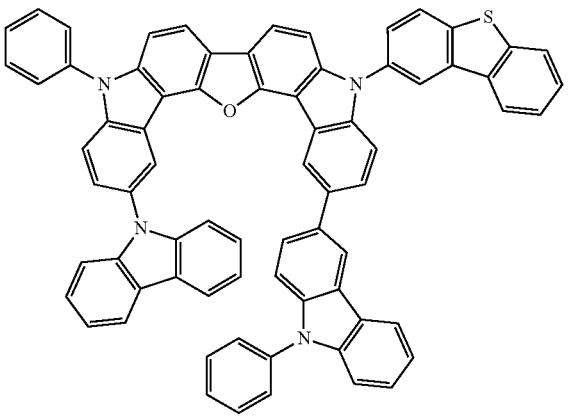
(246)
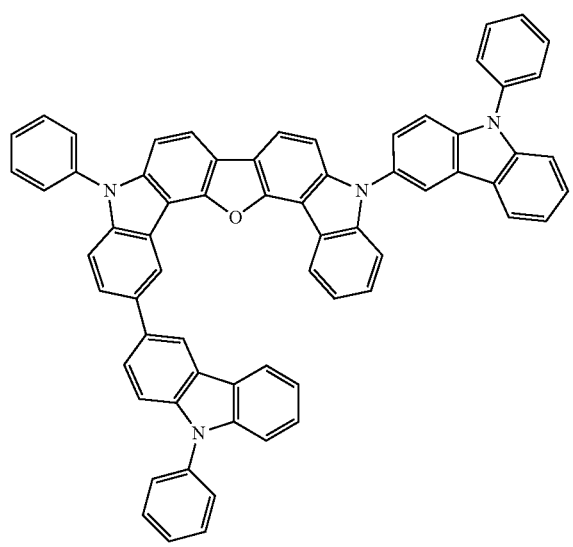
(247)
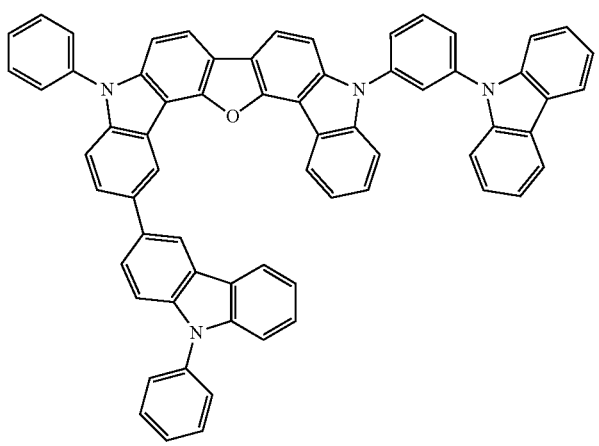
(248)
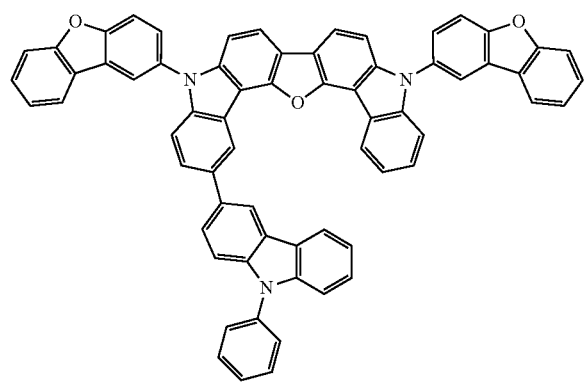
(249)
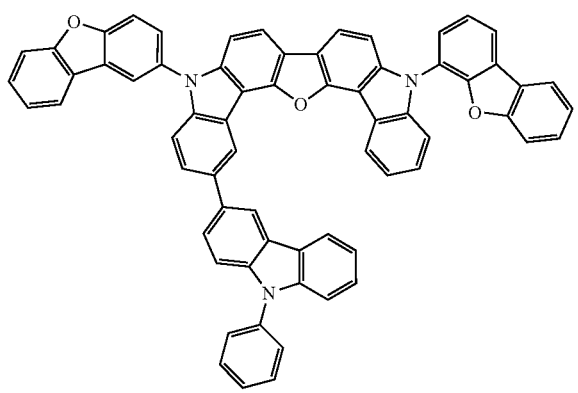

-continued
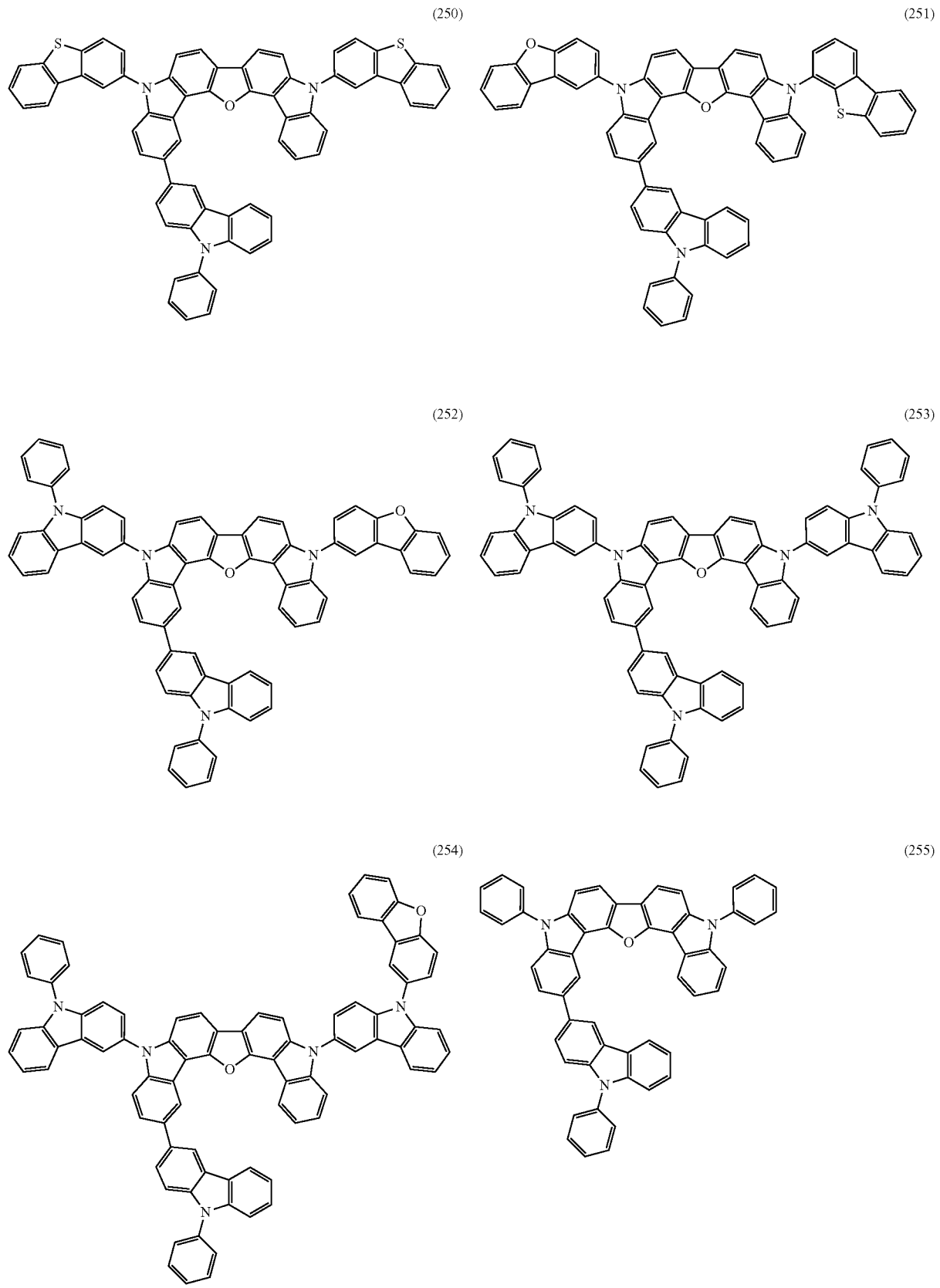

-continued
(256)
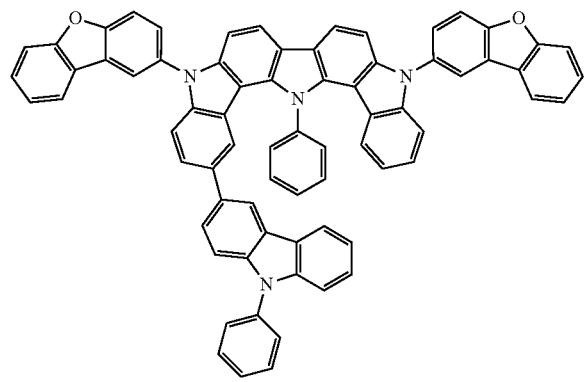
(257)
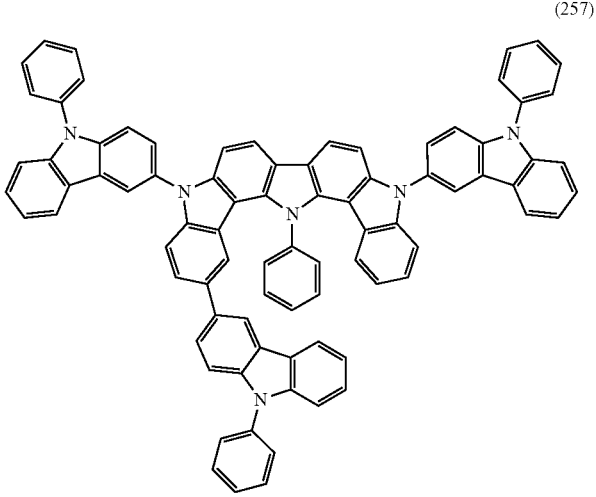
(258)
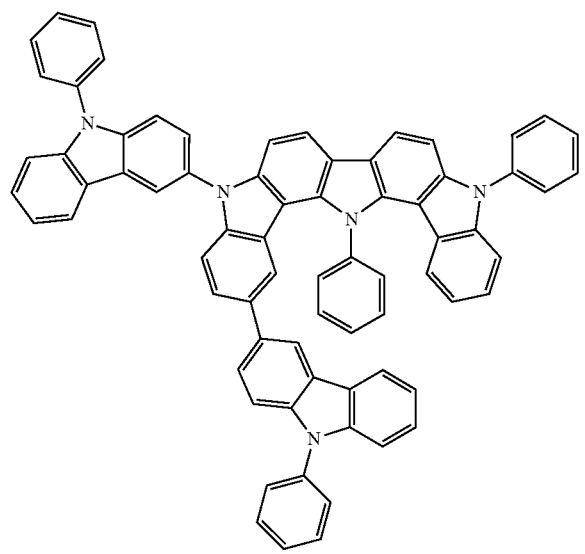
(259)
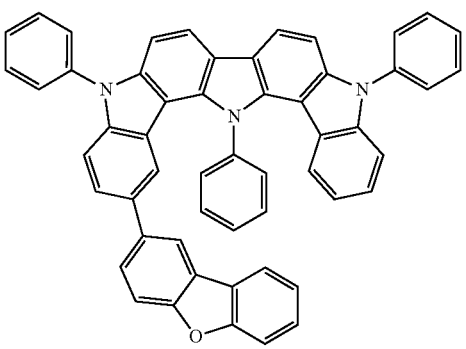
(260)
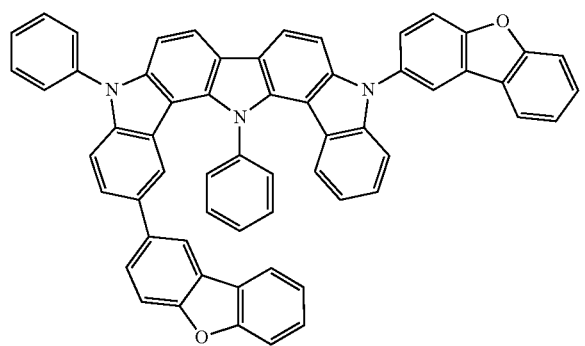
(261)
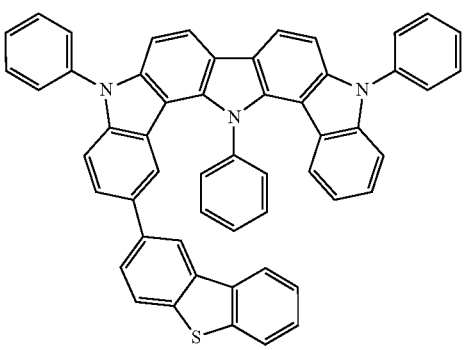

-continued
(262)
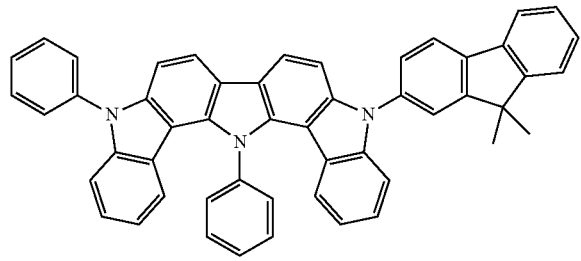
(263)
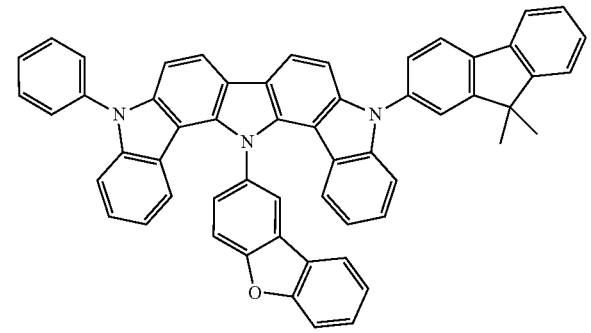
(264)
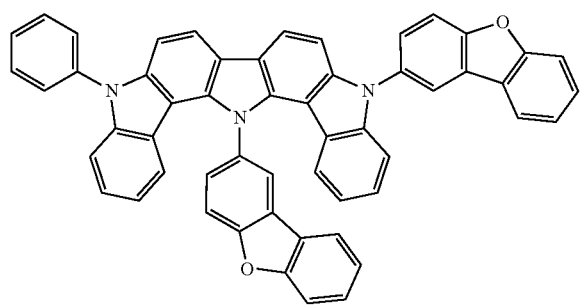
(265)
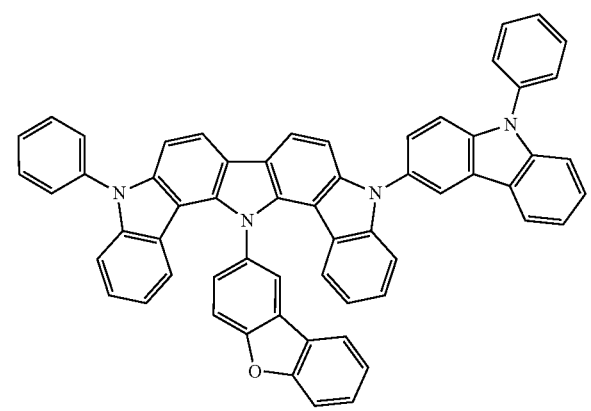
(266)
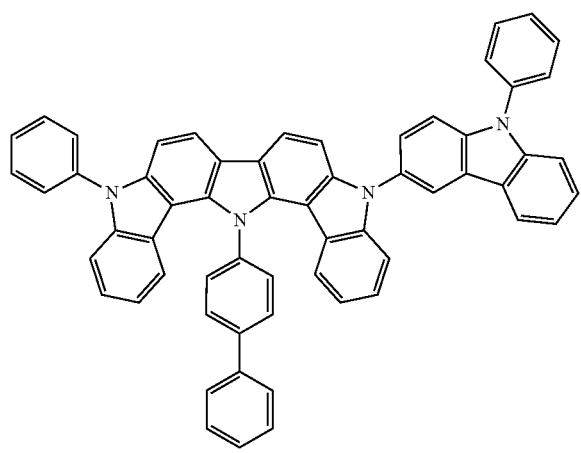
(267)
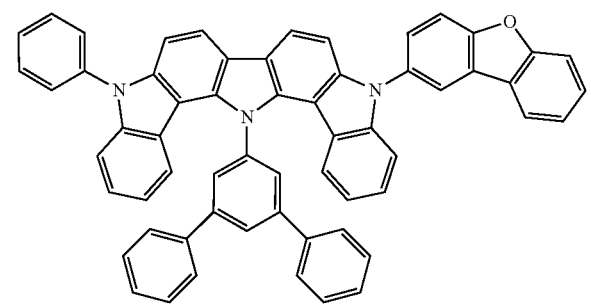
(268)
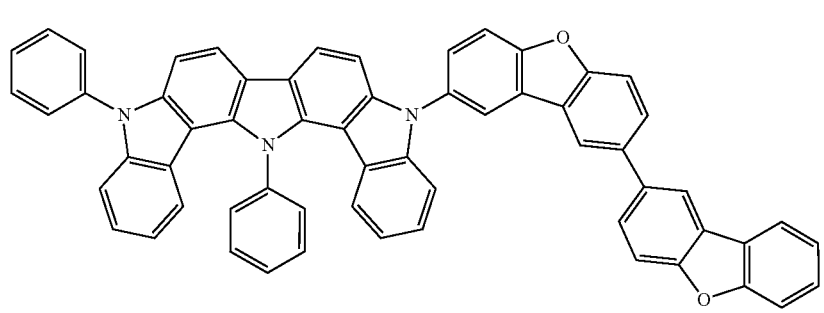

-continued
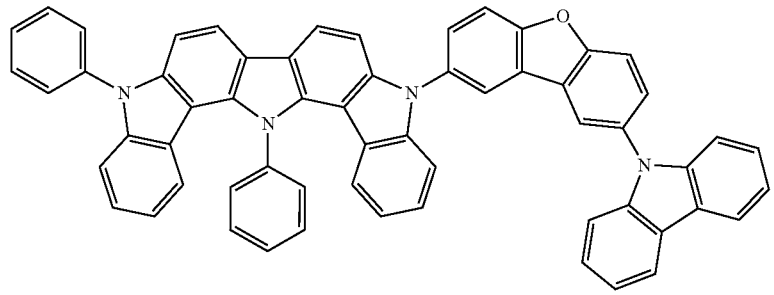
(269)
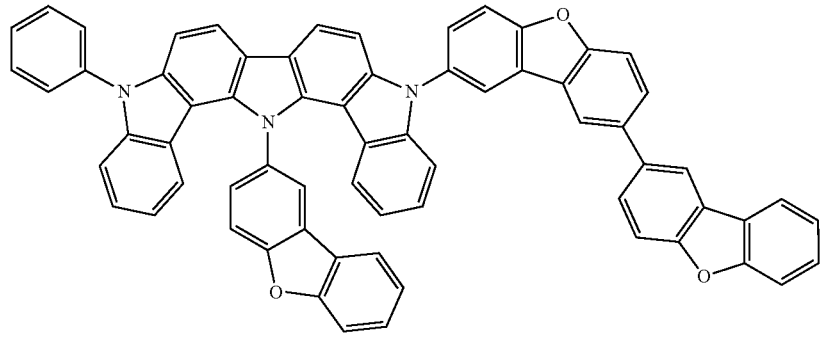
(270)
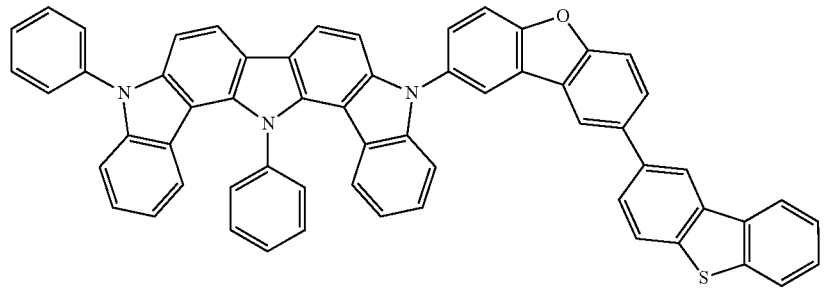
(271)
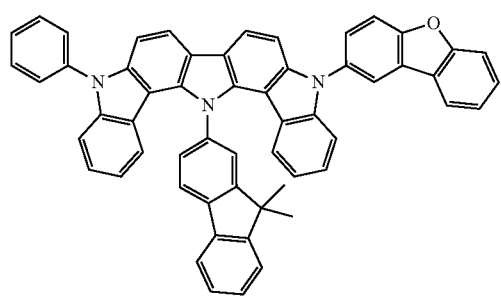
(272)
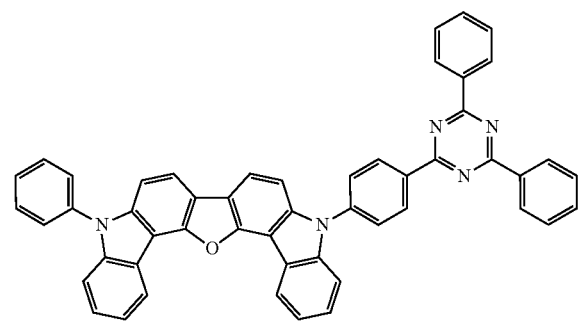
(273)
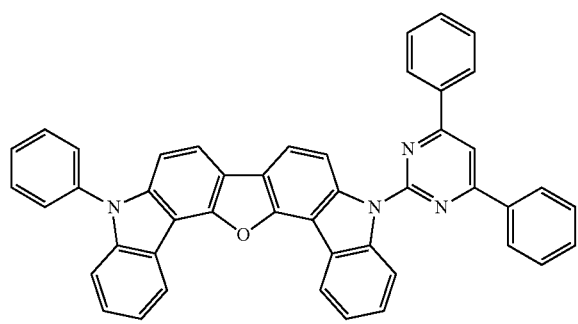
(274)
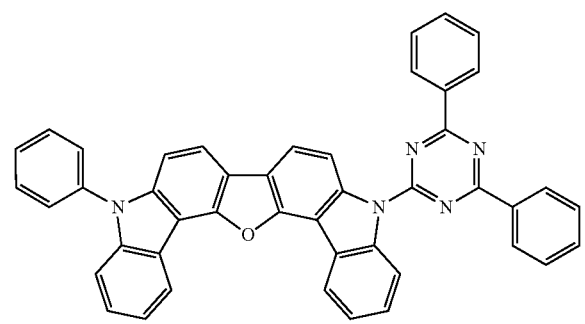
(275)

-continued
(276)
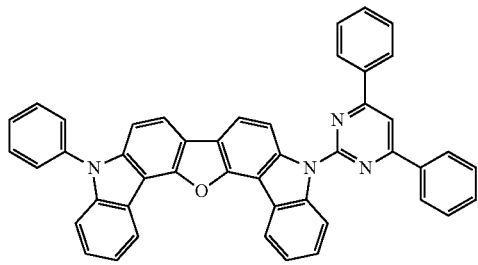
(277)
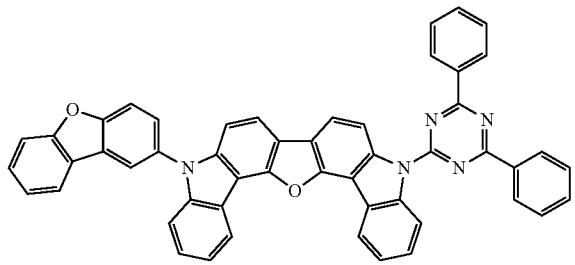
(278)
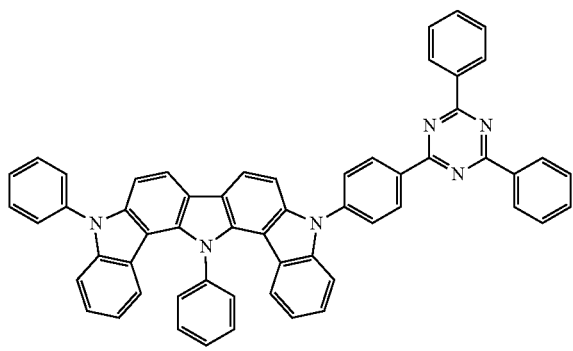
(279)
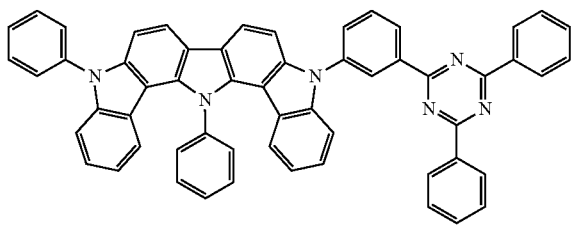
(280)
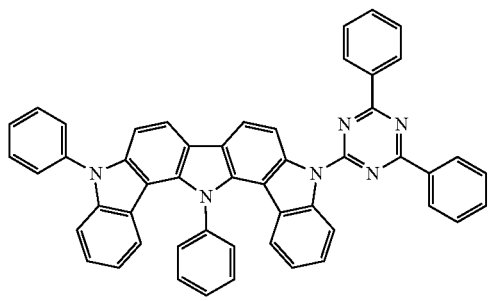
(281)
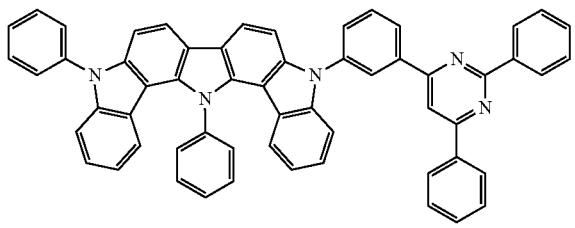
(282)
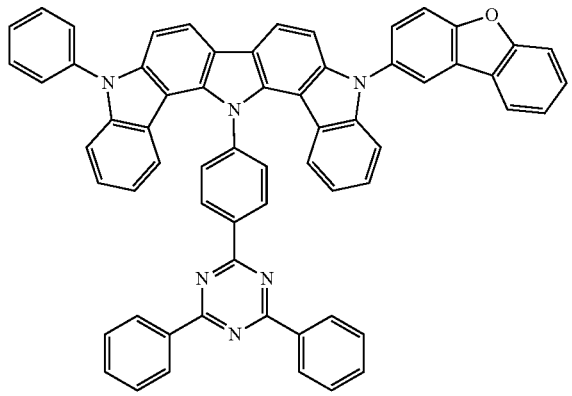
(283)
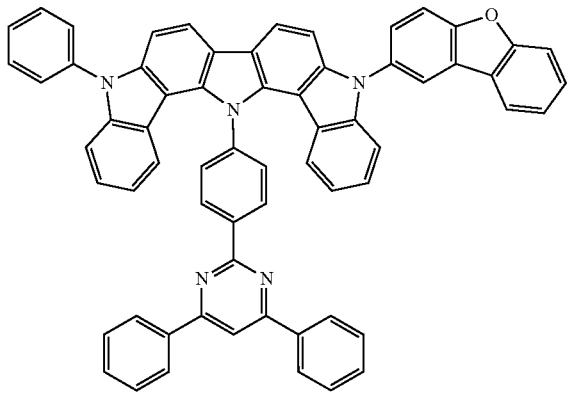

(284)

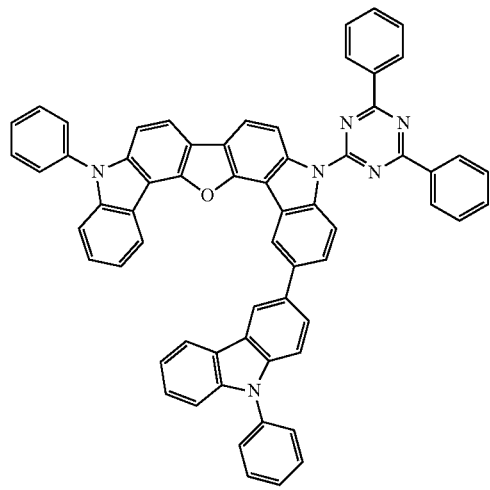

(285)

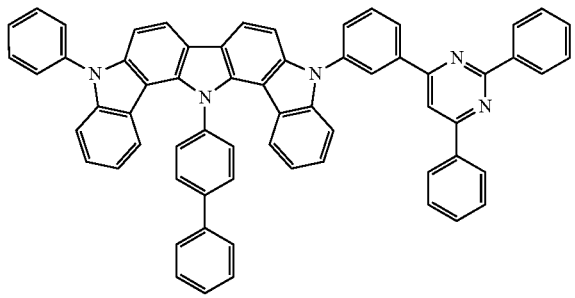

(286)

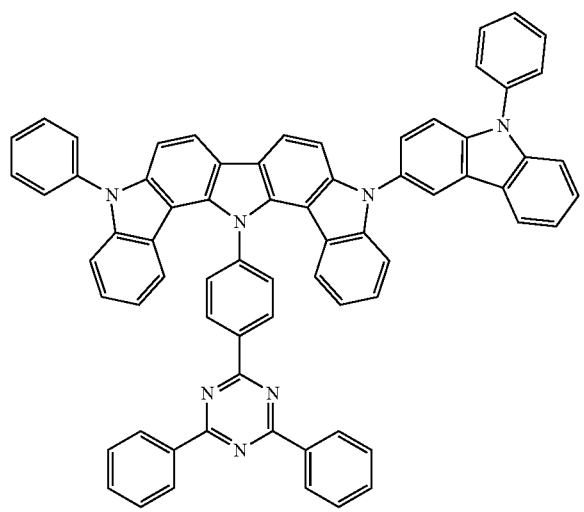

[Material for an Organic EL Device]

The compound represented by the formula (1) of the invention can preferably be used as the material for an organic EL device.

The material for an organic EL device of the invention comprises a compound represented by the formula (1). The compound is preferably used as a material for an emitting layer of an organic EL device, a material for an electron-barrier (blocking) layer of an organic EL device or a material for a hole-barrier (blocking) layer of an organic EL device. More preferably, the compound is used as a material for an emitting layer of an organic EL device and an electron-barrier (blocking) layer of an organic EL device (hereinafter, these materials may often be referred to as the material for an organic EL device of the invention).

The material for an organic EL device of the invention may comprise only the compound represented by the formula (1) of the invention. In addition to the compound represented by the formula (1) of the invention, the material for an organic EL device of the invention may comprise other materials.

[Hole-Transporting Material for an Organic EL Device]

The hole-transporting material for an organic EL device of the invention is a compound represented by the following formula (2) or (3).

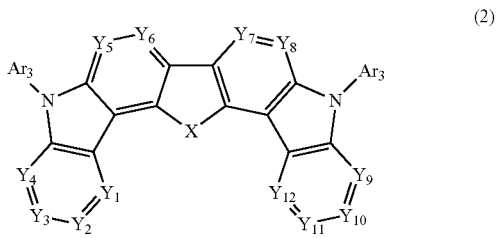

(2)

wherein in the formula (2),

X is O, S or a group represented by N—Ra;

$Y_1$ to $Y_{12}$ are independently N or a group represented by C—Ra;

the two $Ar_3$s are the same substituted or unsubstituted heteroaryl group including 5 to 30 ring atoms;

Ra is a hydrogen atom, a deuterium atom, a substituted or unsubstituted aryl group including 6 to 30 ring carbon atoms, a substituted or unsubstituted heteroaryl group including 5 to 30 ring atoms, a substituted or unsubstituted alkyl group including 1 to 30 carbon atoms, a substituted or unsubstituted fluoroalkyl group including 1 to 30 carbon atoms, a substituted or unsubstituted cycloalkyl group including 3 to 30 ring carbon atoms, a substituted or unsubstituted aralkyl group including 7 to 30 carbon atoms, a substituted phosphoryl group, a substituted silyl group, a cyano group, a nitro group or a carboxy group;

if two or more Ras are present in the formula (2), the plural Ras may be the same or different; and provided that as for all of the following pairs: $Y_1$ and $Y_{12}$, $Y_2$ and $Y_{11}$, $Y_3$ and $Y_{10}$, $Y_4$ and $Y_9$, $Y_5$ and $Y_8$, and $Y_6$ and $Y_7$, $Y_1$ to $Y_{12}$ of each pair are the same as each other.

X, $Y_1$ to $Y_{12}$ and Ra in the formula (2) are the same as those in the formula (1).

The two $Ar_3$s in the formula (2) are the same substituted or unsubstituted heteroaryl group including 5 to 30 ring atoms. This substituted or unsubstituted heteroaryl group including 5 to 30 ring atoms is the same as the substituted or unsubstituted heteroaryl group including 5 to 30 ring atoms in the formula (1).

The heteroaryl group including 5 to 30 ring atoms of $Ar_a$ is preferably a nitrogen-containing heteroaryl group, an oxygen-containing heteroaryl group or a sulfur-containing heteroaryl group, with an oxygen-containing heteroaryl group or a sulfur-containing heteroaryl group being more preferable.

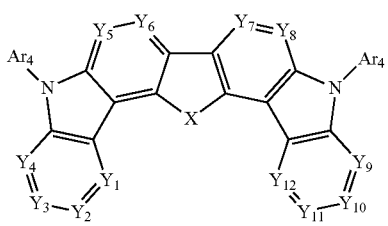

(3)

wherein in the formula (3),

X is O, S or a group represented by N—Ra;

$Y_1$ to $Y_{12}$ are independently N or a group represented by C—Ra;

the two $Ar_4$s are the same substituted or unsubstituted aryl group including 6 to 30 ring carbon atoms;

Ra is a hydrogen atom, a deuterium atom, a substituted or unsubstituted aryl group including 6 to 30 ring carbon atoms, a substituted or unsubstituted heteroaryl group including 5 to 30 ring atoms, an alkyl group including 1 to 30 carbon atoms, a substituted or unsubstituted fluoroalkyl group including 1 to 30 carbon atoms, a substituted or unsubstituted cycloalkyl group including 3 to 30 ring carbon atoms, a substituted or unsubstituted aralkyl group including 7 to 30 carbon atoms, a substituted phosphoryl group, a substituted silyl group, a cyano group, a nitro group or a carboxy group;

if two or more Ras are present in the formula (3), the plural Ras may be the same or different; and provided that as for all of the following pairs: $Y_1$ and $Y_{12}$, $Y_2$ and $Y_{11}$, $Y_3$ and $Y_{10}$, $Y_4$ and $Y_9$, $Y_5$ and $Y_8$, and $Y_6$ and $Y_7$, $Y_1$ to $Y_{12}$ of each pair are the same as each other.

X, $Y_1$ to $Y_{12}$ and Ra in the formula (3) are the same as those in the formula (1).

The two $Ar_4$s in the formula (3) are the same substituted or unsubstituted aryl group including 6 to 30 ring carbon atoms. This substituted or unsubstituted aryl group including 6 to 30 ring carbon atoms is the same as the substituted or unsubstituted aryl group including 6 to 30 ring carbon atoms in the formula (1).

The aryl group including 6 to 30 ring carbon atoms of $Ar_4$ is preferably a phenyl group, a 9,9-dimethylfluorenyl group, a 9,9-diphenylfluorenyl group, a spirofluorenyl group or a group derived from a triphenylene ring. As the aryl group including the substituent, a dibenzofuranyl group, a dibenzofluorenylphenyl group or the like can be mentioned.

Specific examples of the hole-transporting material for an organic EL device represented by the formula (2) or (3) are given below:

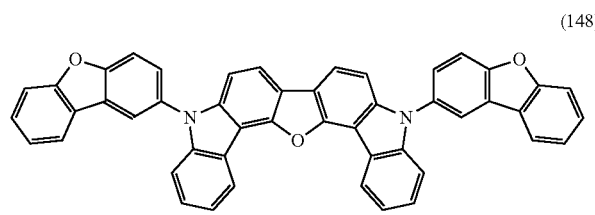
(148)

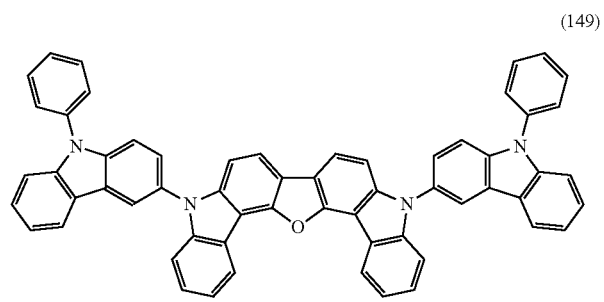
(149)

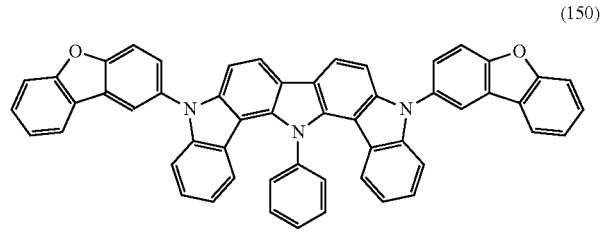
(150)

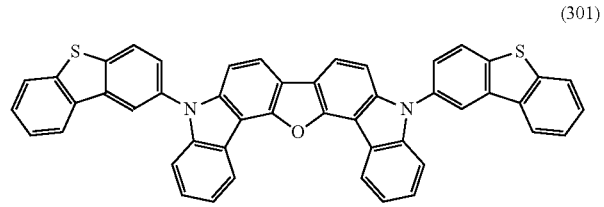
(301)

-continued
(302)
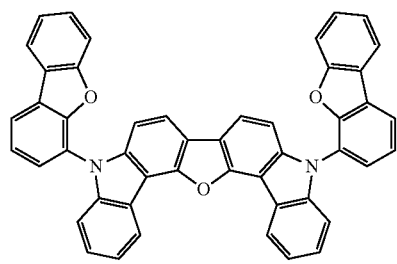
(303)
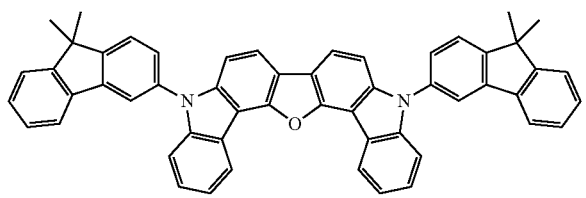
(304)
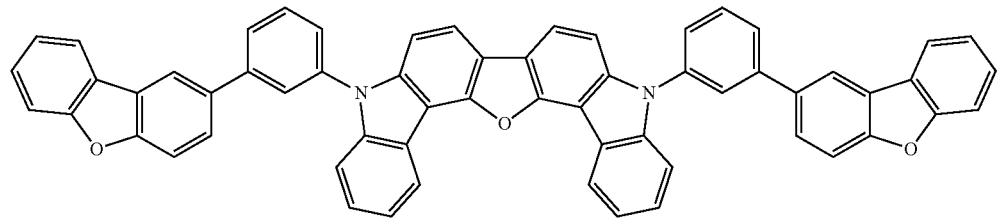
(305)
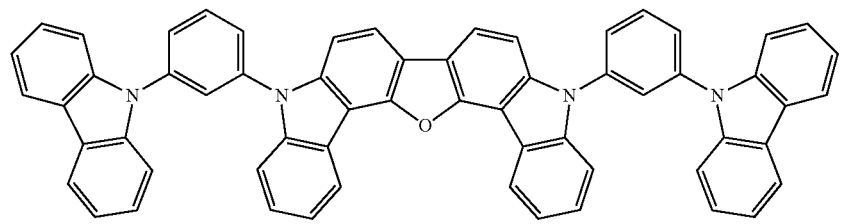
(306)
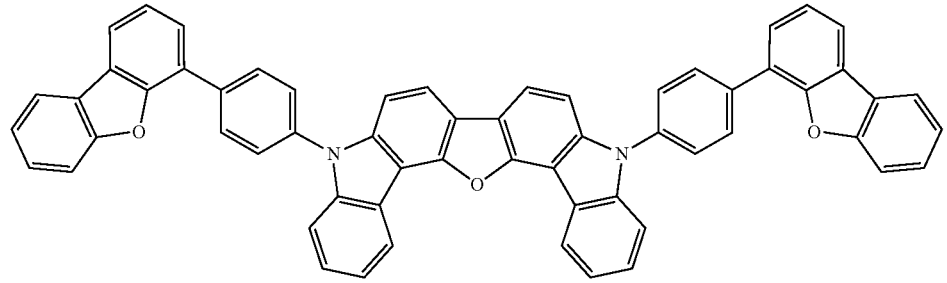
(307)
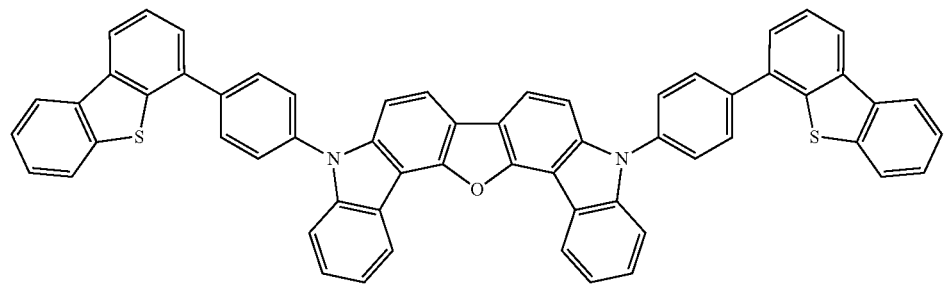
(308)
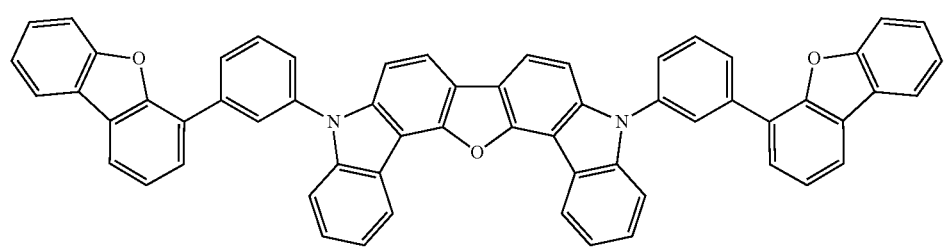

(309)
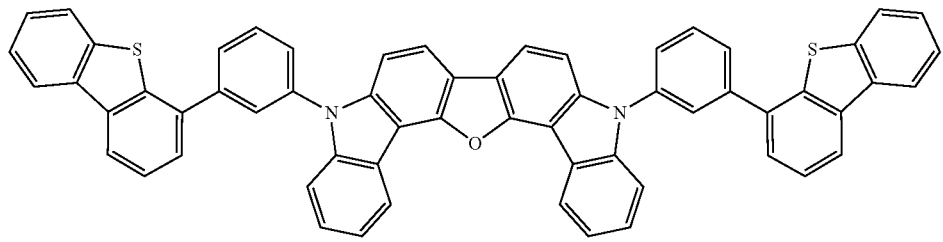
(310)
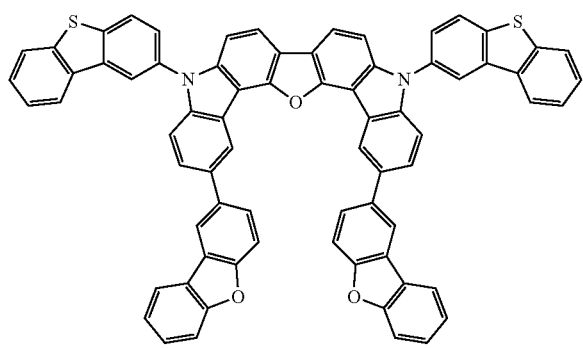
(311)
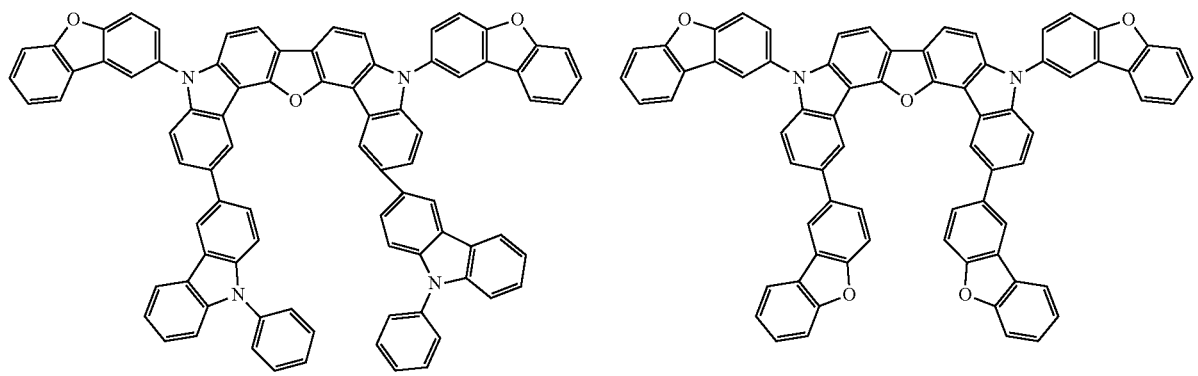
(312)
(313)
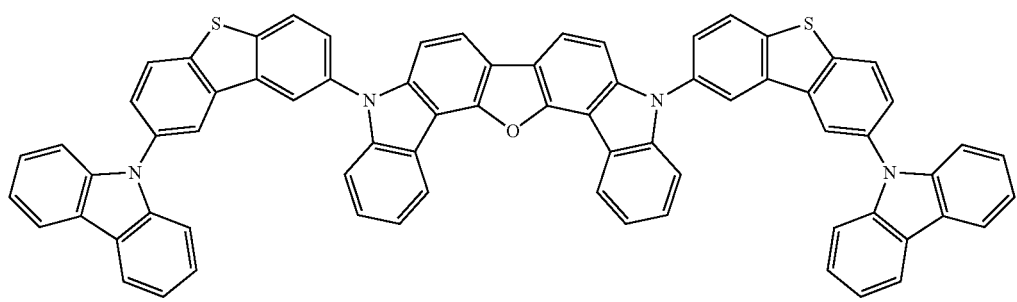
(314)
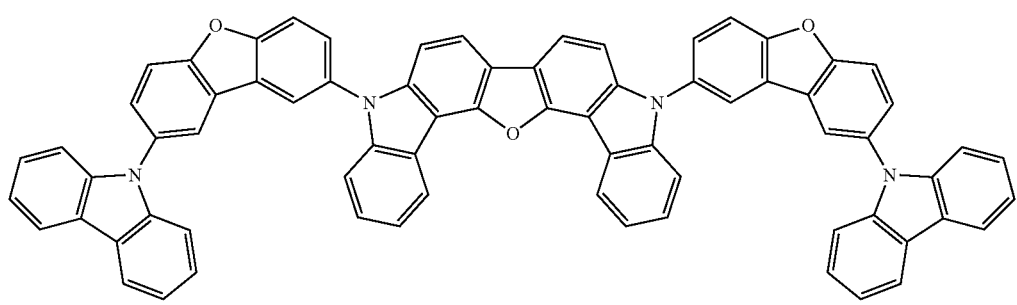

-continued
(315) 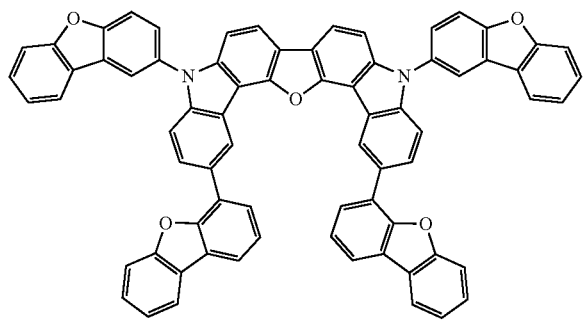
(316) 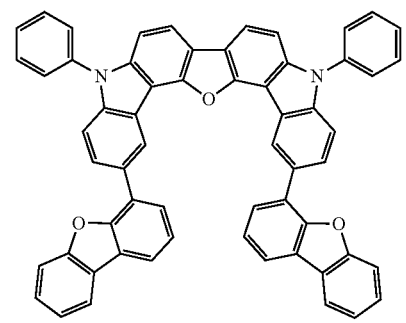
(317) 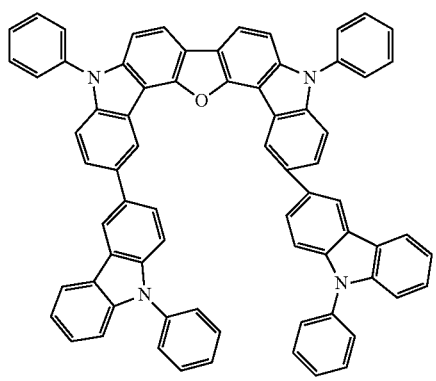
(318) 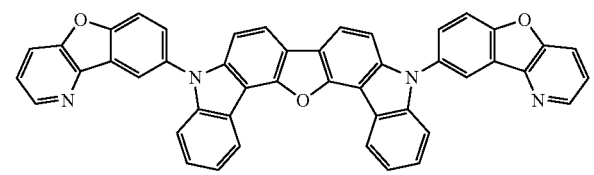
(319) 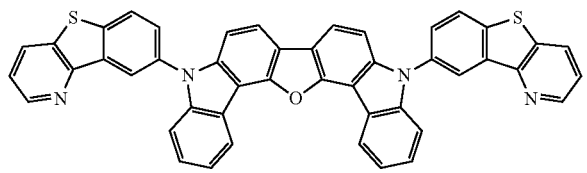
(320) 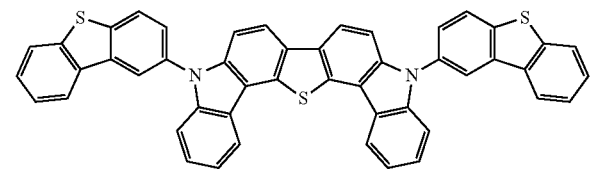
(321) 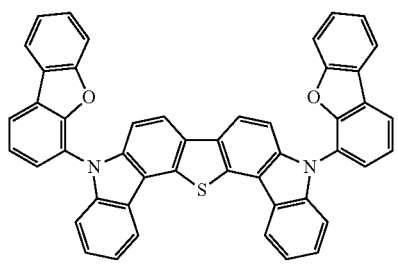
(322) 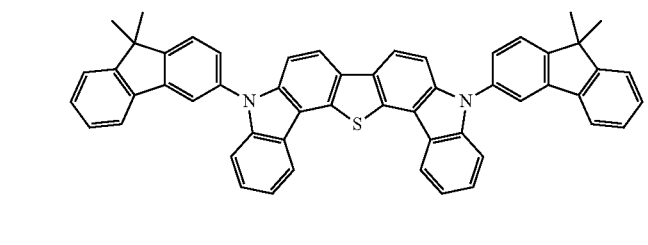
(323) 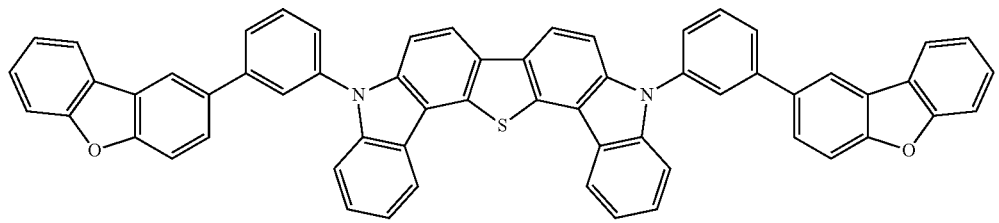

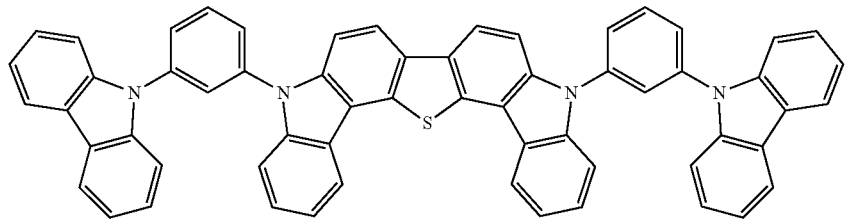
(324)
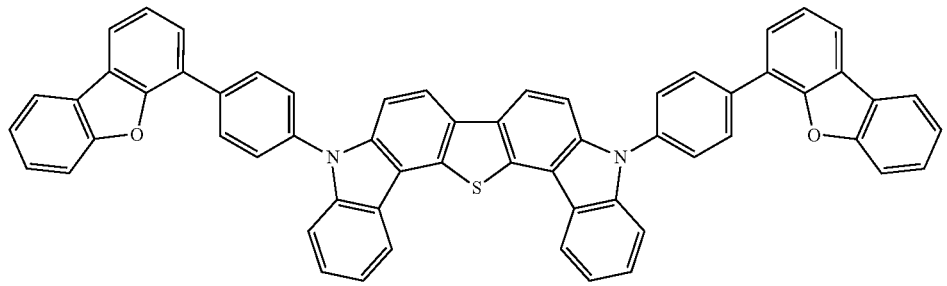
(325)
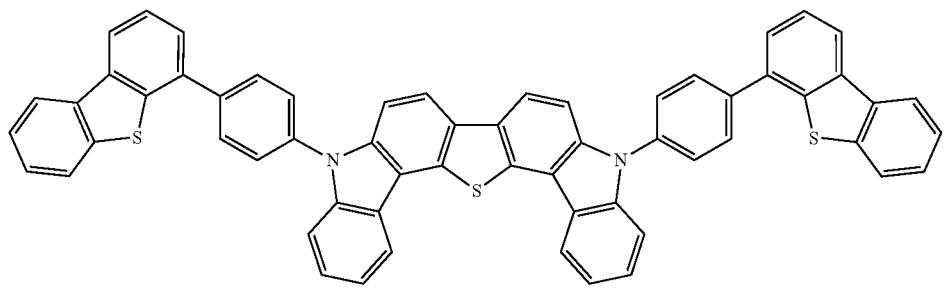
(326)
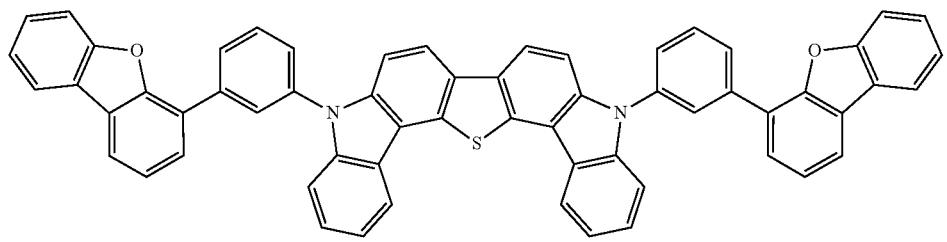
(327)
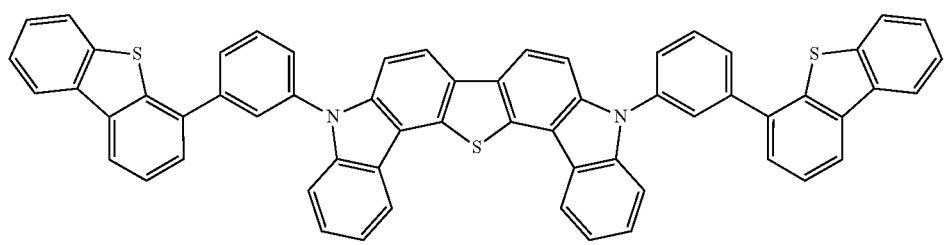
(328)

(329)
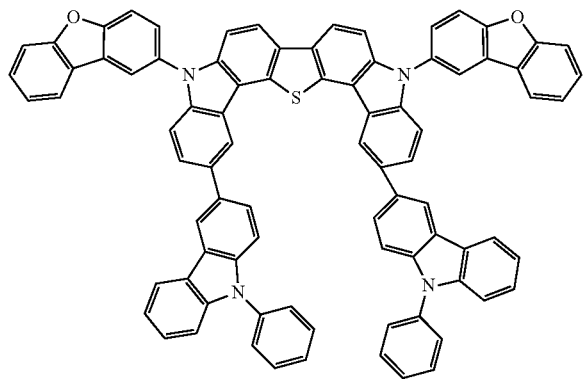
(330)
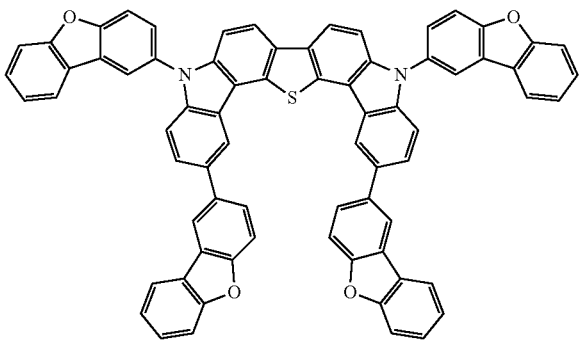
(331)
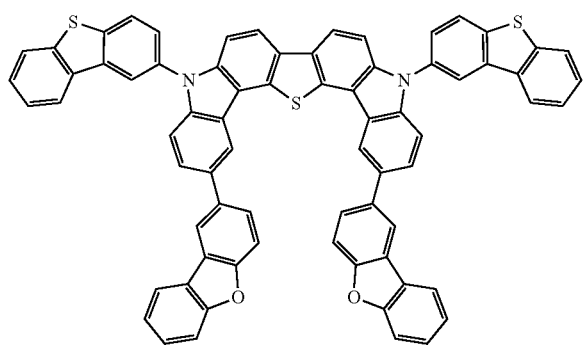
(332)
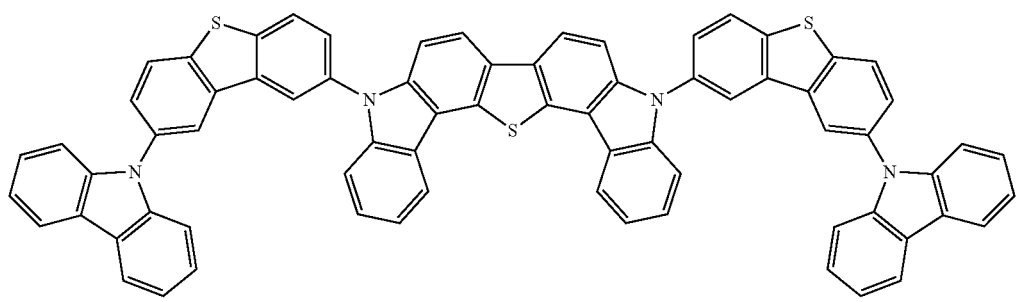
(333)
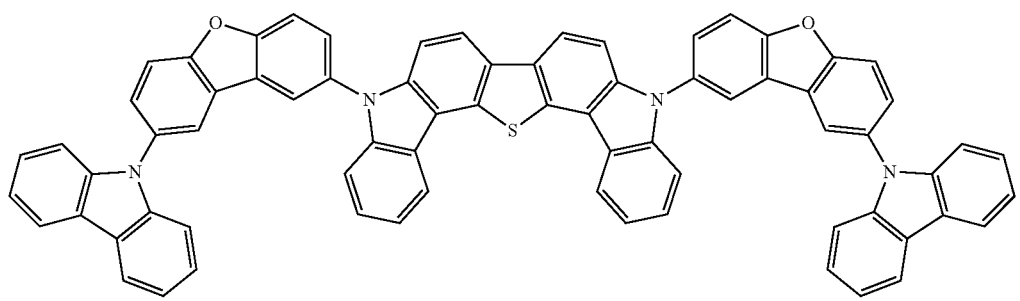

-continued
(334)
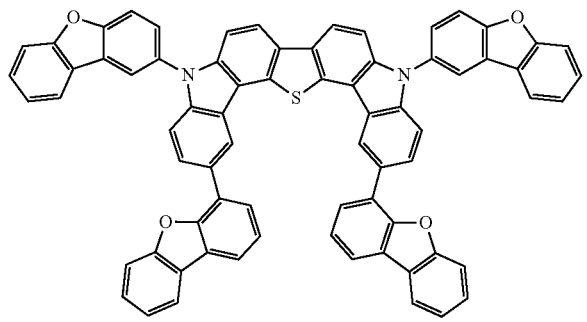
(335)
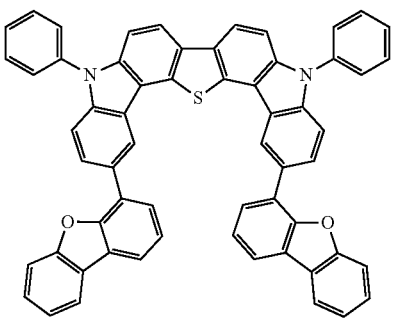
(336)
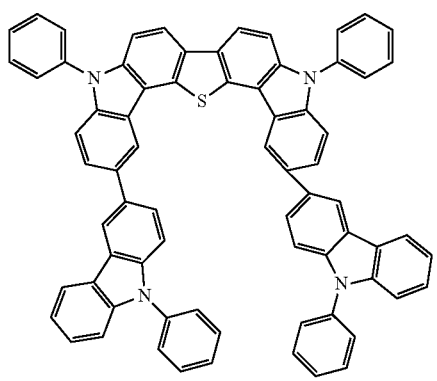
(337)
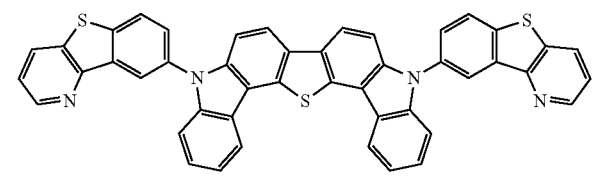
(338)
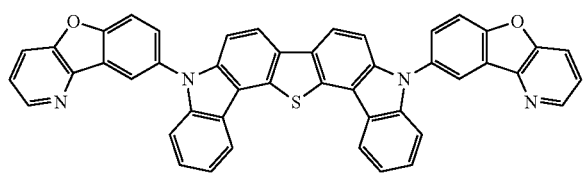
(339)
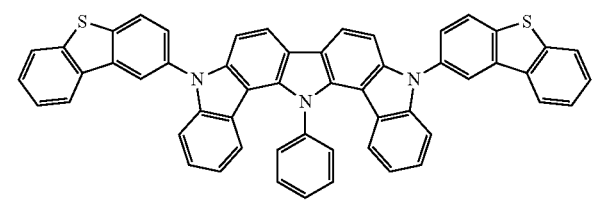
(340)
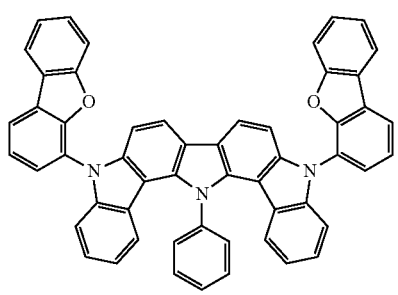
(341)
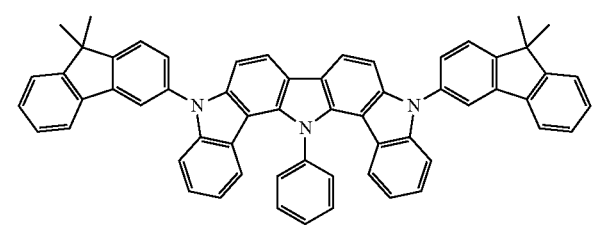
(342)
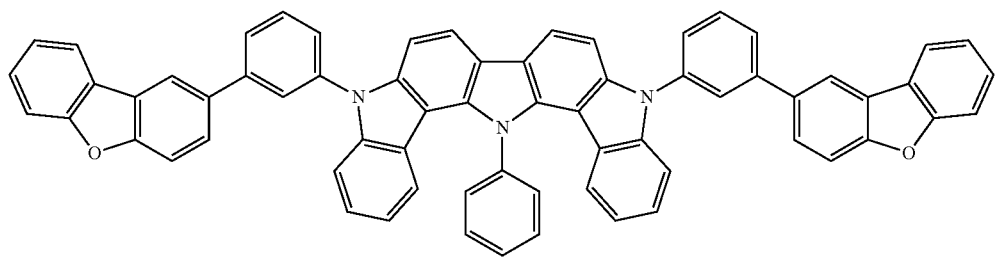

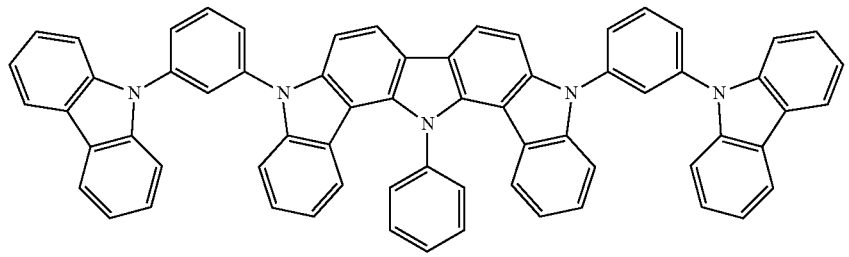
(343)
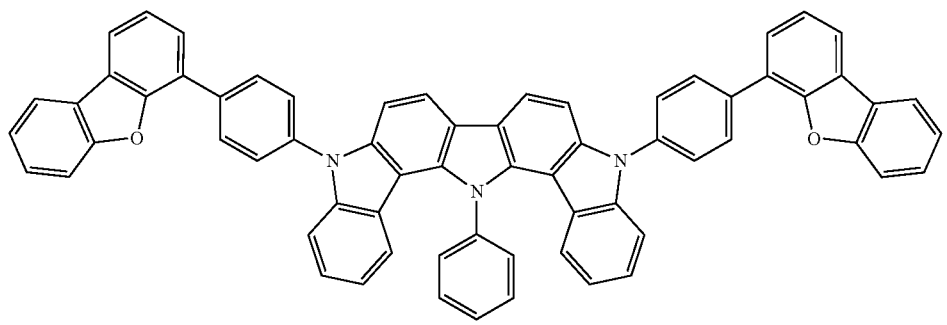
(344)
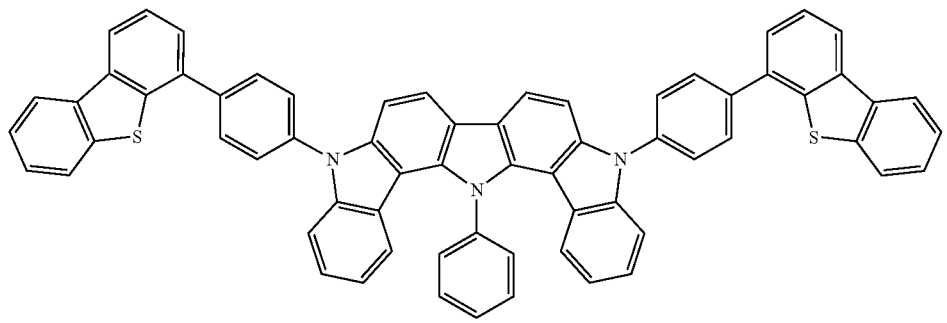
(345)
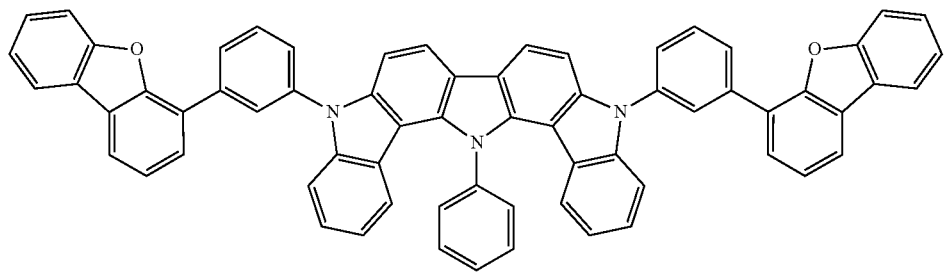
(346)
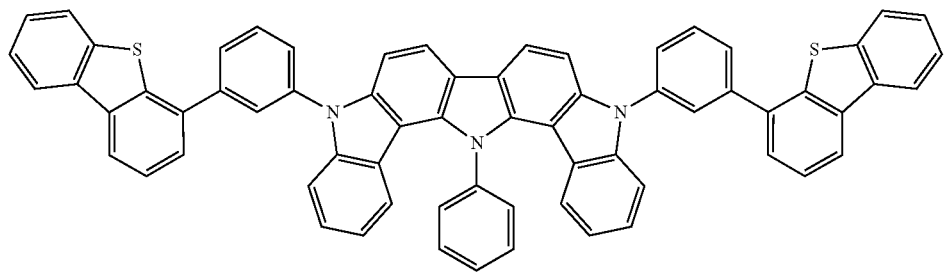
(347)

(348)
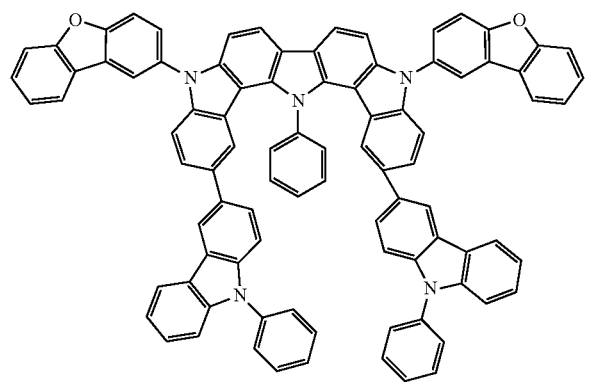
(349)
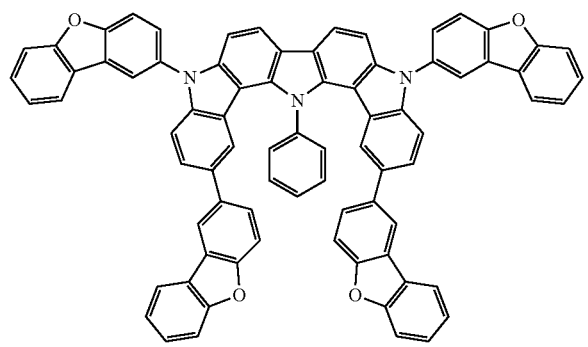
(350)
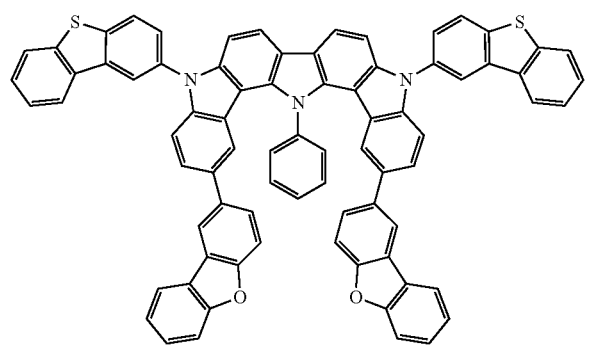
(351)
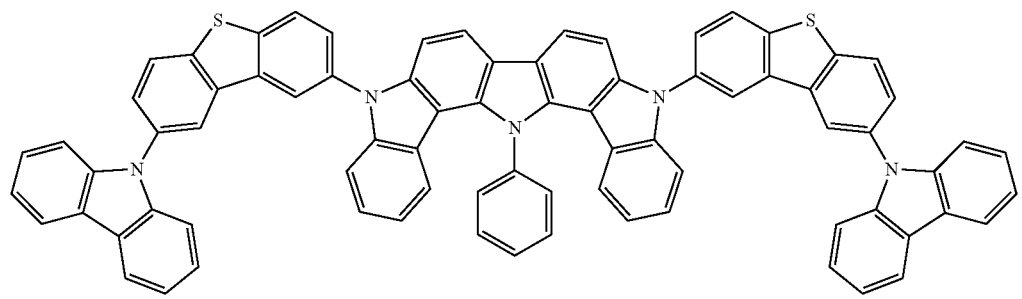
(352)
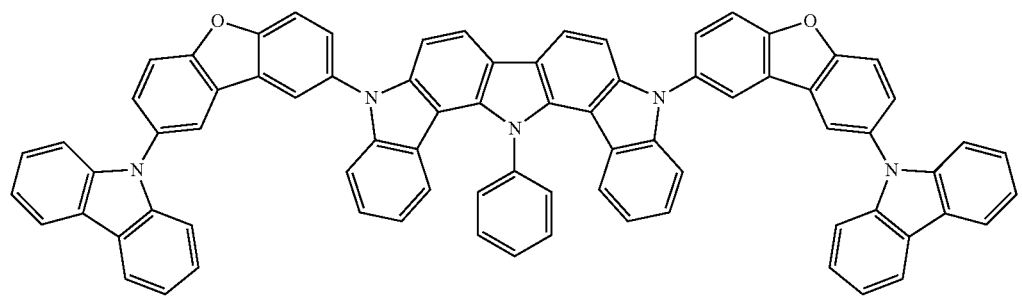

-continued
(353)
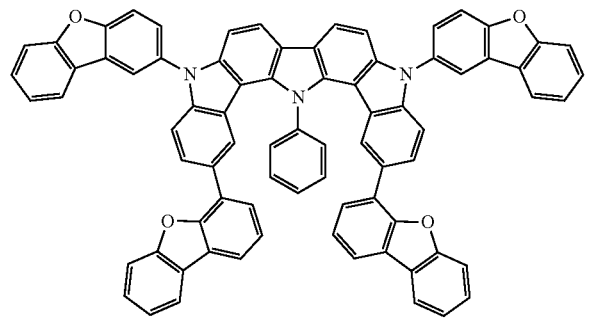
(354)
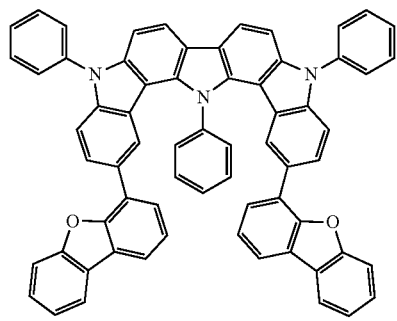
(355)
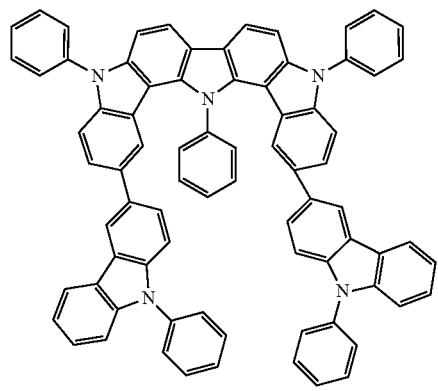
(356)
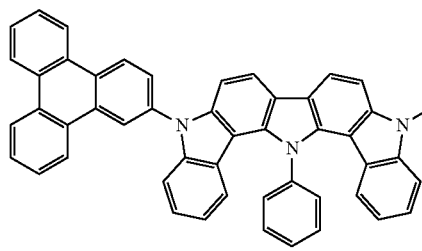
(357)
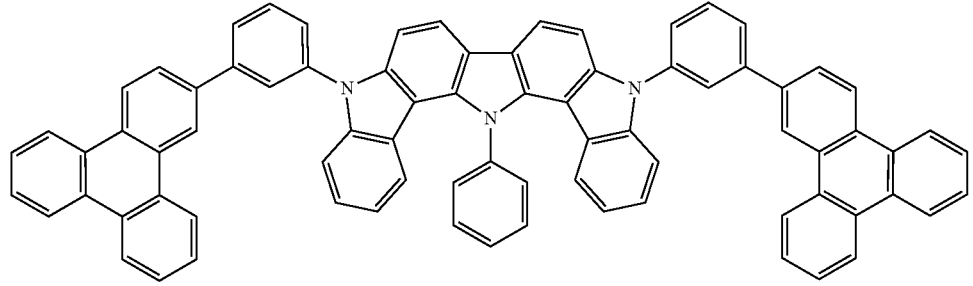
(358)
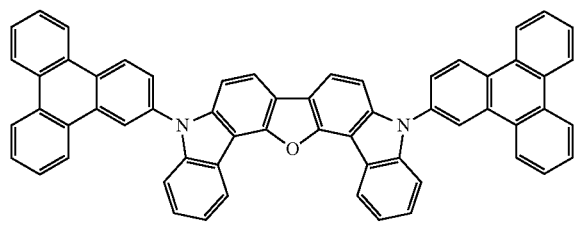
(359)
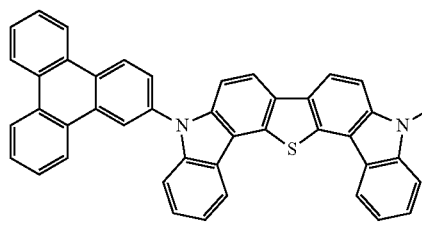
(360)
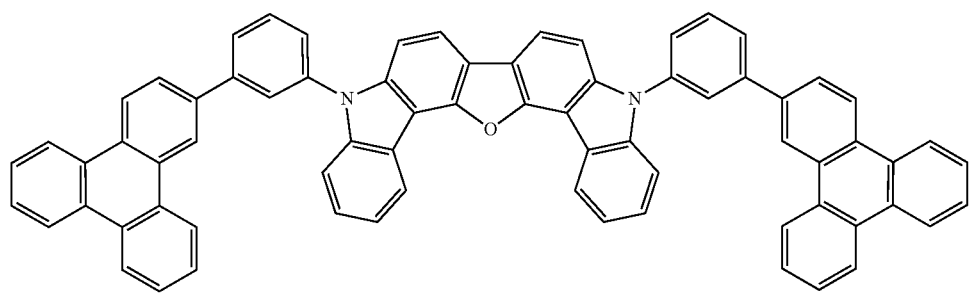

-continued
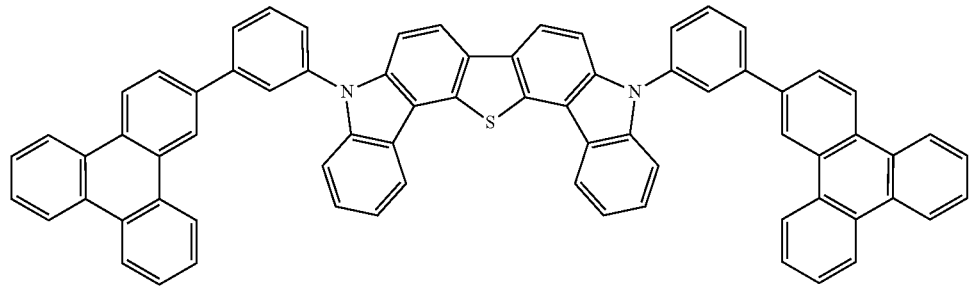
(361)
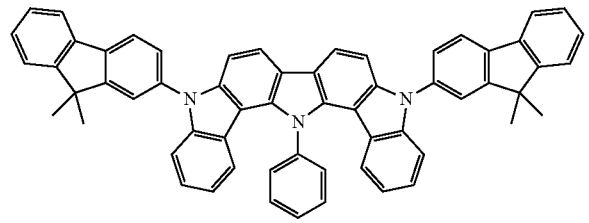
(362)
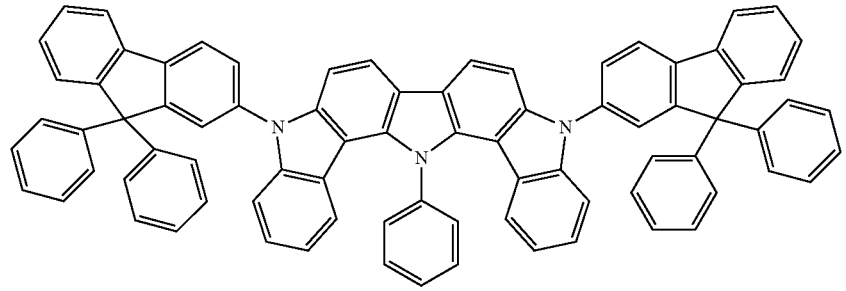
(363)
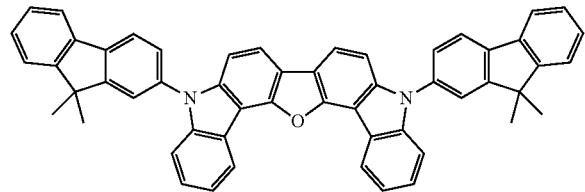
(364)
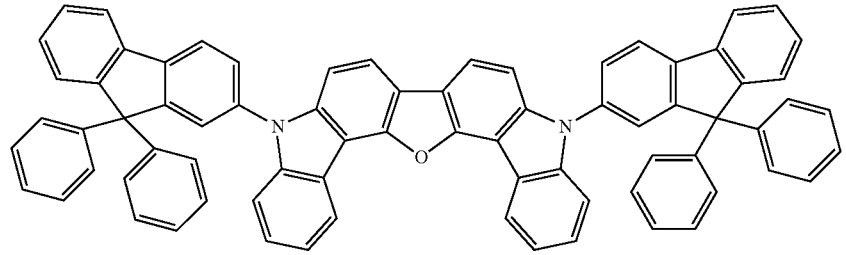
(365)
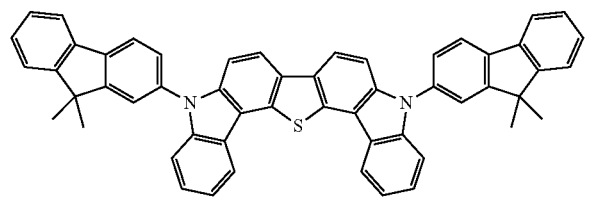
(366)

-continued

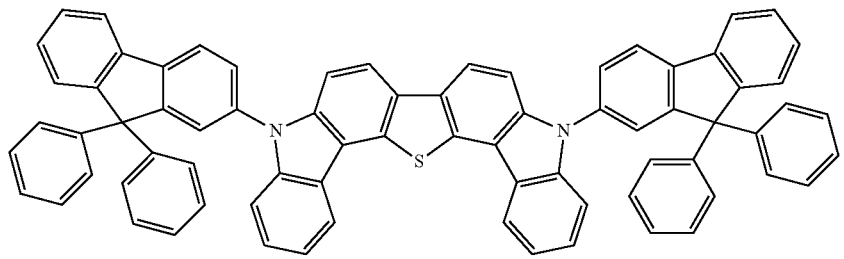
(367)

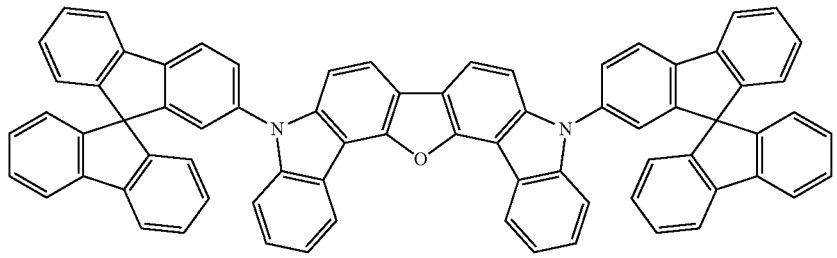
(368)

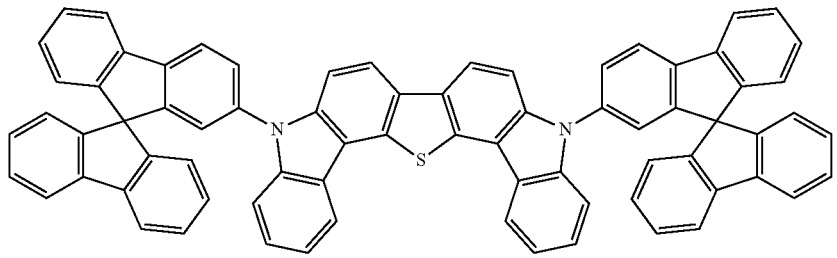
(369)

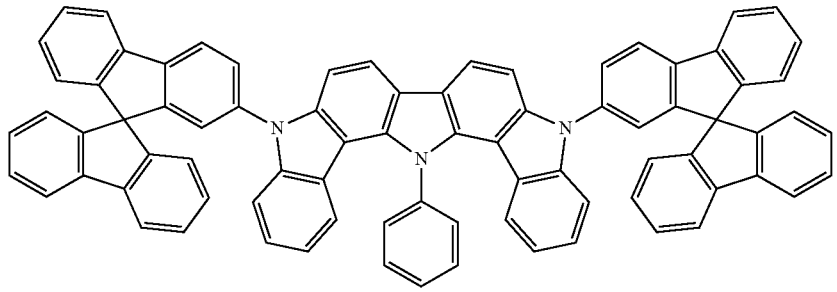
(370)

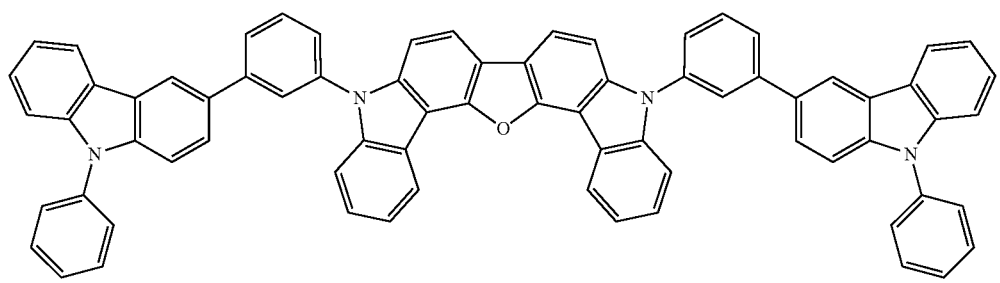
(371)

An explanation will be made on the organic EL device of the invention.

A first organic EL device of the invention has one or more organic thin film layers including an emitting layer between an anode and a cathode. At least one layer of the organic thin film layers comprises the material for an organic EL device of the invention.

In one aspect of the first organic EL device according to the invention, the organic EL device has one or more organic thin film layers including an emitting layer between an anode and a cathode, and the emitting layer comprises the material for an organic EL device of the invention. It is further preferred that the material for an organic EL device that comprises the compound represented by the formula (1) be contained as the host material of the emitting layer.

In another aspect of the first organic EL device of the invention, it is preferred that, between an anode and a cathode, one or more organic thin film layers including an emitting layer and an electron-barrier (blocking) layer that is present between the anode and the emitting layer and is adjacent to the emitting layer be provided, and that the electron-barrier (blocking) layer comprise the material for an organic EL device of the invention.

In one aspect of the second organic EL device of the invention, one or more organic thin film layers including an emitting layer be provided between an anode and a cathode, and a hole-transporting zone be provided between the anode and the emitting layer, and the hole-transporting zone comprises the hole-transporting material for an organic EL device that is the compound represented by the formula (2).

In another aspect of the second organic EL device of the invention, one or more organic thin film layers including an emitting layer be provided between an anode and a cathode, and a hole-transporting zone be provided between the anode and the emitting layer, and the hole-transporting zone comprises the hole-transporting material for an organic EL device that is the compound represented by the formula (3).

FIG. 1 is a schematic view showing the layer configuration according to one embodiment of the organic EL device of the invention.

An organic EL device 1 has a configuration in which, on a substrate 10, an anode 20, a hole-transporting zone 30, a phosphorescent emitting layer 40, an electron-transporting zone 50 and a cathode 60 are stacked in this sequence. The hole-transporting zone 30 means a hole-transporting layer, a hole-injecting layer, an electron-blocking layer or the like. Similarly, the electron-transporting zone 50 means an electron-transporting layer, an electron-injecting layer, a hole-blocking layer or the like. These layers may not necessarily be formed. However, it is preferred that at least one or more of these layers be formed. In this device, the organic thin film layer means each organic layer provided in the hole-transporting zone 30 and each organic layer provided in the phosphorescent emitting layer 40 and the electron-transporting zone 50. Among these organic thin film layers, at least one layer comprises the material for an organic EL device of the invention, or one or more layers of the hole-transporting zone 30 comprises the material for an organic EL device of the invention. As a result, the organic EL device can emit light highly efficiently.

Meanwhile, the content of the compound represented by the formula (1) relative to the organic thin film layer that comprise the material for an organic EL device of the invention is preferably 1 to 100 wt %. Similarly, the content of the compound represented by the formula (2) or (3) relative to any layer of the hole-transporting zone that comprises the hole-transporting material for an organic EL device of the invention is preferably 1 to 100 wt %.

In the organic EL device of the invention, it is preferred that the phosphorescent emitting layer 40 comprise the material for an organic EL device of the invention. The material is preferably used as a host material of the emitting layer. The material for an organic EL device of the invention has a sufficiently large triplet energy. Therefore, even if a blue phosphorescent dopant material is used, the triplet energy of the phosphorescent dopant material can be confined efficiently within the emitting layer, Although the material for an organic EL device of the invention can be used not only in a blue-emitting layer but also in an emitting layer that emits light having a longer wavelength (green to red, or the like), the material is used preferably in a blue-emitting layer.

The phosphorescent emitting layer contains a phosphorescent emitting material (phosphorescent dopant). As the phosphorescent emitting material, metal complex compounds can be given. Preferable is a compound having a metal atom selected from Ir, Pt, Os, Au, Cu, Re and Ru and a ligand. The ligand preferably has an ortho-metalated bond.

In respect of a high phosphorescence quantum yield and capability of improving the external quantum efficiency of an emitting device, the phosphorescent emitting material is preferably a compound having a metal atom selected from Ir, Os and Pt. Further preferable are a metal complex such as an iridium complex, an osmium complex and a platinum complex. Among them, an iridium complex and a platinum complex are more preferable, and an ortho-metalated iridium complex is most preferable. The phosphorescent emitting material may be used singly or in combination of two or more. As the blue phosphorescent layer, BD1 mentioned later can be given, for example. Further, bis[2-(4',6'-difluorophenyl)pyridinato-N,C2']iridium (III) tetrakis(1-pyrazolyl)borate (abbreviation: Flr6), bis[2-(4',6'-difluorophenyl)pyridinato-N,C2']iridium (III) picolinate (abbreviation: Flrpic), bis[2-(3',5' bistrifluoromethylphenyl) pyridinato-N,C2']iridium (III) picolinate (abbreviation: Ir(CF3ppy)2(pic)), bis[2-(4',6'-difluorophenyl)pyridinato-N,C2']iridium (III) acetylacetonate (abbreviation: Flracac) or the like can be given.

The concentration of the phosphorescent emitting material in the phosphorescent emitting layer is not particularly restricted, but preferably 0.1 to 40 weight % (wt %), more preferably 0.1 to 30 weight % (wt %).

It is preferred that the material for an organic EL device of the invention be used in an organic thin film layer adjacent to the phosphorescent emitting layer 40. For example, when a layer that contains the material for an organic EL device of the invention is formed between the phosphorescent emitting layer 40 and the hole transporting zone 30 (adjacent layers nearer to the anode), said layer has a function as an electron-barrier layer or a function as an exciton-blocking layer.

Meanwhile, the barrier (blocking) layer is a layer which blocks transporting of carriers or diffusion of excitons. The organic layer which prevents electrons from leaking from an emitting layer into a hole-transporting zone is mainly defined as the electron-barrier layer. The organic layer which prevents holes from leaking from an emitting layer into an electron-transporting zone is often defined as the hole-barrier layer. In addition, the organic layer which prevents triplet excitons generated in an emitting layer from diffusing to the peripheral layers having lower triplet energy than that of the emitting layer is often defined as the exciton-blocking layer (triplet-barrier layer).

Further, the material for an organic EL device of the invention may be used in organic thin film layers adjacent to the phosphorescent emitting layer 40, and also in other organic thin film layers that are connected to the adjacent organic thin film layers.

In addition to the above-mentioned embodiments, the organic EL device of the invention can employ various known configurations. Further, the emission from an emitting layer can be outcoupled from the anode, the cathode or the both.

In the organic EL device of the invention, it is also preferred that at least one of an electron-donating dopant and an organic metal complex be added to an interfacial region of the cathode and the organic thin film layer. Due to such a configuration, the organic EL device can have improved luminance or a prolonged lifetime.

As the electron-donating dopant, at least one selected from an alkali metal, an alkali metal compound, an alkaline-earth metal, an alkaline-earth metal compound, a rare-earth metal, a rare-earth metal compound and the like can be given.

As the organic metal complex, at least one selected from an organic metal complex including an alkali metal, an organic metal complex including an alkaline-earth metal, an organic metal complex including a rare-earth metal and the like can be given.

As the alkali metal, lithium (Li) (work function: 2.93 eV), sodium (Na) (work function: 2.36 eV), potassium (K) (work function: 2.28 eV), rubidium (Rb) (work function: 2.16 eV), cesium (Cs) (work function: 1.95 eV) and the like can be given. One having a work function of 2.9 eV or less is particularly preferable. Among these, K, Rb and Cs are preferable, Rb or Cs is further preferable, and Cs is most preferable.

As the alkaline-earth metal, calcium (Ca) (work function: 2.9 eV), strontium (Sr) (work function: 2.0 eV or more and 2.5 eV or less), barium (Ba) (work function: 2.52 eV) and the like can be given. One having a work function of 2.9 eV or less is particularly preferable.

As the rare-earth metal, scandium (Sc), yttrium (Y), cerium (Ce), terbium (Tb), ytterbium (Yb) and the like can be given. One having a work function of 2.9 eV or less is particularly preferable.

Among the above-mentioned metals, the preferable metals have a particularly high reducing ability, and hence can provide the resulting organic EL device with an improved luminance or a prolonged lifetime by adding a relatively small amount thereof to an electron-injecting region.

Examples of the alkali metal compound include an alkali oxide such as lithium oxide ($Li_2O$), cesium oxide ($Cs_2O$) or potassium oxide ($K_2O$), and an alkali halide such as lithium fluoride (LiF), sodium fluoride (NaF), cesium fluoride (CsF) or potassium fluoride (KF). Among these, lithium fluoride (LiF), lithium oxide ($Li_2O$) and sodium fluoride (NaF) are preferable.

Examples of the alkaline-earth metal compound include barium oxide (BaO), strontium oxide (SrO), calcium oxide (CaO), and mixtures thereof such as barium strontium acid ($Ba_xSr_{1-x}O$) ($0<x<1$) and barium calcium acid ($Ba_xCa_{1-x}O$) ($0<x<1$). Among these, BaO, SrO and CaO are preferred.

Examples of the rare-earth metal compound include ytterbium fluoride ($YbF_3$), scandium fluoride ($ScF_3$), scandium oxide ($ScO_3$), yttrium oxide ($Y_2O_3$), cerium oxide ($Ce_2O_3$), gadolinium fluoride ($GdF_3$) and terbium fluoride ($TbF_3$). Among these, $YbF_3$, $ScF_3$ and $TbF_3$ are preferable.

The organic metal complexes are not particularly limited as long as they each contain, as a metal ion, at least one of alkali metal ions, alkaline-earth metal ions, and rare-earth metal ions, as mentioned above. Meanwhile, preferred examples of the ligand include, but are not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfluborane, bipyridyl, phenanthroline, phthalocyanine, porphyrin, cyclopentadiene, β-diketones, azomethines, and derivatives thereof.

Regarding the addition form of the electron-donating dopant and the organic metal complex, it is preferred that the electron-donating dopant and the organic metal complex be formed in a shape of a layer or an island in the interfacial region. A preferred method for the formation is a method in which an organic substance as a light emitting material or an electron-injecting material for forming the interfacial region is deposited at the same time at least one of the electron-donating dopant and the organic metal complex is deposited by a resistant heating deposition method, thereby dispersing at least one of the electron-donating dopant and the organic metal complex reducing dopant in the organic substance. The dispersion concentration by molar ratio of the organic substance to the electron-donating dopant and/or the organic metal complex is normally 100:1 to 1:100, preferably 5:1 to 1:5.

In a case where at least one of the electron-donating dopant and the organic metal complex is formed into the shape of a layer, the light-emitting material or the electron-injecting material which serves as an organic layer in the interface is formed into the shape of a layer. After that, at least one of the electron-donating dopant and the organic metal complex is solely deposited by the resistant heating deposition method to form a layer preferably having a thickness of 0.1 nm or more and 15 nm or less.

In a case where at least one of the electron-donating dopant and the organic metal complex is formed into the shape of an island, the light emitting material or the electron-injecting material which serves as an organic layer in the interface is formed into the shape of an island. After that, at least one of the electron-donating dopant and the organic metal complex is solely deposited by the resistant heating deposition method to form an island preferably having a thickness of 0.05 nm or more and 1 nm or less.

In addition, the ratio of the main component (emitting material or electron-injecting material) to at least one of the electron-donating dopant and the organic metal complex in the organic EL device of the invention is preferably 5:1 to 1:5, more preferably 2:1 to 1:2 in terms of molar ratio.

In the first organic EL device of the invention, configurations of other layers than those in which the above-mentioned material for an organic EL device of the invention is used are not particularly restricted, and known materials or the like can be used. Hereinbelow, a brief explanation will be made on the layer of the first device. However, materials to be applied to the first organic EL device of the invention are not limited to those mentioned below.

[Substrate]

As the substrate, a glass sheet, a polymer sheet or the like can be used.

Examples of the glass sheet include soda lime glass, barium-strontium-containing glass, lead glass, aluminosilicate glass, borosilicate glass, barium borosilicate glass, quartz, and the like. Examples of materials of the polymer sheet include polycarbonate, acryl, polyethylene terephthalate, polyethersulfone, polysulfone, and the like.

[Anode]

The anode is formed of a conductive material, for example. A conductive material having a work function larger than 4 eV is suitable.

As the conductive material, carbon, aluminum, vanadium, iron, cobalt, nickel, tungsten, silver, gold, platinum, palladium or the like, alloys thereof, an oxidized metal such as tin oxide and indium oxide used in an ITO substrate and a NESA substrate and further an organic conductive resin such as polythiophene and polypyrrole can be given.

If necessary, the anode may be formed of two or more layers. If emission from the emitting layer is outcoupled from the anode, the transmittance of the cathode for the emitted light is preferably larger than 10%.

[Cathode]

The cathode is formed of a conductive material, for example. A conductive material having a work function smaller than 4 eV is suitable.

As the conductive material, magnesium, calcium, tin, lead, titanium, yttrium, lithium, ruthenium, manganese, aluminum, lithium fluoride or the like, and alloys thereof can be given. The conductive material is not limited thereto.

As the alloy, a magnesium/silver alloy, a magnesium/indium alloy, a lithium/aluminum alloy or the like can be given as representative examples. The alloys are not limited thereto. The amount ratio of metals forming an alloy is controlled by the temperature of a deposition source, the atmosphere, the degree of vacuum or the like, and an appropriate ratio is selected.

If necessary, the cathode may be formed of two or more layers. The cathode can be formed by forming a thin layer from the above-mentioned conductive material by a method such as deposition, sputtering or the like.

When outcoupling light from the emitting layer through the cathode, it is preferable that the cathode have a light transmittance of more than 10%.

The sheet resistance of the cathode is preferably several hundred 0/square or less. The thickness of the cathode is normally 10 nm to 1 µm, and preferably 50 to 200 nm.

[Emitting Layer]

When a phosphorescent emitting layer is formed by using materials other than the material for an organic EL device of the invention, materials which are known as a material for a phosphorescent emitting layer can be used. Specifically, reference can be made to Japan Patent Application No. 2005-517938 or the like.

The first organic EL device of the invention may comprise a fluorescent emitting layer 70 as the device shown in FIG. 2. As the fluorescent emitting layer, known materials can be used in addition to the material for an organic EL device of the invention.

The emitting layer can be of a double-host (often referred to as host/co-host) type in which two kinds of host materials are used. Specifically, in the emitting layer, an electron-transporting host and a hole-transporting host may be combined to control the carrier balance. The material for an organic EL device of the invention can be used as a host or a co-host.

The emitting layer also can be of a double-dopant type in which two kinds of emitting materials (dopant materials) are used. By incorporating two or more kinds of dopant materials having a high quantum yield to the emitting layer, each dopant emits light. For example, there may be a case that a yellow emitting layer is realized by co-depositing a host, and a red dopant and a green dopant.

The emitting layer may be a single layer or may have a stacked layer structure. When the emitting layers are stacked, due to accumulation of electrons and holes in the interface of the emitting layer, the recombination region may be concentrated in the emitting layer interface. In such a case, quantum efficiency is improved.

[Hole-Injecting Layer and Hole-Transporting Layer]

The hole-injecting/transporting layer is a layer that helps holes to be injected to an emitting layer and transports the injected holes to an emitting region. It has a large hole mobility and normally a small ionization energy. The hole-injecting/transporting layer may be of a single layer structure or may be of a multilayer structure in which the hole-injecting layer and the hole-transporting layer are stacked. Further, the hole-injecting layer may be of a multilayer structure or the hole-transporting layer may be of a multilayer structure. In this case, a layer that is adjacent to the emitting layer may be an electron-barrier (blocking) layer. As the material for the electron-barrier (blocking) layer, a material that comprises the material for an organic EL device of the invention can be used.

As the material for a hole-injecting/transporting layer, materials which can transport holes to an emitting layer at lower electric field intensity are preferable. In addition, it is preferred that the hole mobility be at least $10^{-4}$ cm$^2$/V·second when an electric field having an intensity of $10^4$ to $10^6$ V/cm is applied, for example.

Specific examples of materials for a hole-injecting/transporting layer include triazole derivatives (see U.S. Pat. No. 3,112,197 and others), oxadiazole derivatives (see U.S. Pat. No. 3,189,447 and others), imidazole derivatives (see JP-B-37-16096 and others), polyarylalkane derivatives (see U.S. Pat. Nos. 3,615,402, 3,820,989 and 3,542,544, JP-B-45-555 and 51-10983, JP-A-51-93224, 55-17105, 56-4148, 55-108667, 55-156953 and 56-36656, and others), pyrazoline derivatives and pyrazolone derivatives (see U.S. Pat. Nos. 3,180,729 and 4,278,746, JP-A-55-88064, 55-88065, 49-105537, 55-51086, 56-80051, 56-88141, 57-45545, 54-112637 and 55-74546, and others), phenylenediamine derivatives (see U.S. Pat. No. 3,615,404, JP-B-51-10105, 46-3712, 47-25336 and 54-119925, and others), arylamine derivatives (see U.S. Pat. Nos. 3,567,450, 3,240,597, 3,658, 520, 4,232,103, 4,175,961 and 4,012,376, JP-B-49-35702 and 39-27577, JP-A-55-144250, 56-119132 and 56-22437, DE1,110,518, and others), amino-substituted chalcone derivatives (see U.S. Pat. No. 3,526,501, and others), oxazole derivatives (ones disclosed in U.S. Pat. No. 3,257, 203, and others), styrylanthracene derivatives (see JP-A-56-46234, and others), fluorenone derivatives (JP-A-54-110837, and others), hydrazone derivatives (see U.S. Pat. No. 3,717,462, JP-A-54-59143, 55-52063, 55-52064, 55-46760, 57-11350, 57-148749 and 2-311591, and others), stilbene derivatives (see JP-A-61-210363, 61-228451, 61-14642, 61-72255, 62-47646, 62-36674, 62-10652, 62-30255, 60-93455, 60-94462, 60-174749 and 60-175052, and others), silazane derivatives (U.S. Pat. No. 4,950,950), polysilanes (JP-A-2-204996), and aniline copolymers (JP-A-2-282263).

Further, an inorganic compound such as P-type Si and P-type SiC can be used as the hole-injecting material.

As the material for a hole-injecting/transporting layer, a cross-linking material can be used. As the cross-linking hole-injecting/transporting layer, a layer formed of the cross-linking material disclosed in Chem. Mater. 2008, 20, 413-422, Chem. Mater. 2011, 23(3), 658-681, WO2008108430, WO2009102027, WO2009/123269, WO2010016555, WO2010018813 or the like insolubilized by heat, light or the like can be given, for example.

[Electron-Injecting Layer and Electron-Transporting Layer]

The electron-injecting/transporting layer helps electrons to be injected to an emitting layer and transports the injected electrons to an emitting region. It has a large electron mobility. The electron-injecting/transporting layer may be of a single layer structure or may be of a multilayer structure in which the electron-injecting layer and the electron-transporting layer are stacked. Further, the electron-injection layer may be of a multilayer structure or the electron-transporting layer may be of a multilayer structure. In this case, a layer that is adjacent to the emitting layer may be a hole-barrier (blocking) layer. As the material for the hole-barrier (blocking) layer, a known material can be used. For example, the compound (H1) used in Example 2 mentioned later can be used.

In the organic EL device, it is known that since emitted light is reflected by an electrode (a cathode, for example), emission outcoupled directly from an anode interferes with emission outcoupled after being reflected by the electrode. In order to utilize the interference effect efficiently, the film thickness of the electron injecting/transporting layer is appropriately selected to be several nm to several μm. When the film thickness is particularly large, it is preferred that the electron mobility be at least $10^{-6}$ cm$^2$/Vs or more at an applied electric field intensity of $10^4$ to $10^6$ V/cm in order to avoid an increase in voltage.

As the electron-transporting material used in the electron-injecting/transporting layer, an aromatic heterocyclic compound containing one or more hetero atoms in the molecule is preferably used, with a nitrogen-containing ring derivative being particularly preferable. Further, as the nitrogen-containing ring derivative, an aromatic ring compound having a nitrogen-containing 6-membered ring or 5-membered ring skeleton, or a fused aromatic ring compound having a nitrogen-containing 6-membered ring or 5-membered ring skeleton is preferable. Examples thereof include compounds containing a pyridine ring, a pyrimidine ring, a triazine ring, a benzimidazole ring, a phenanthroline ring, a quinazoline ring or the like in the skeleton.

In addition, an organic layer with a semiconductor property may be formed by doping a donor material (n) or doping an acceptor material (p). Representative examples of N-doping include one in which an electron-transporting material is doped with a metal such as Li or Cs. Representative examples of P-doping include one in which a hole-transporting material is doped with an acceptor material such as F4TCNQ (see Japan Patent No. 3695714, for example).

Each layer of the organic EL device of the invention can be formed by using known methods including the dry-type film formation such as vacuum deposition, sputtering, plasma, ion-plating or the like and the wet-type film formation such as spin coating, dipping, flow coating or the like.

The film thickness of each layer is not particularly limited, but should be set to be a proper thickness. If the film thickness is too large, a large voltage is required to be applied in order to obtain a certain light output, thereby leading to lowering in efficiency. If the film thickness is too small, due to generation of pinholes or the like, a sufficient luminance cannot be obtained when an electric field is applied.

Normally, the film thickness is preferably 5 nm to 10 μm, and the range of 10 nm to 0.2 μm is further preferable.

In the second organic EL device of the invention, no specific restrictions are imposed on the configuration other than the above-mentioned layer in which the hole-transporting material for an organic EL device of the invention is used, and a known material or the like can be used. Hereinbelow, a brief explanation will be made of each layer of the second organic EL device. The materials used in the second organic EL device of the invention are not limited thereto.

The substrate, the anode, the cathode, the electron-injecting layer and the electron-transporting layer that constitute the organic EL device are the same as those in the first organic EL device mentioned above.

The emitting layer is also the same as that in the above-mentioned first organic EL device.

However, the material for an organic EL device of the invention may not necessarily be used in the emitting layer. Preferably, the material for an organic EL device of the invention is used in the emitting layer.

The hole-injecting layer and the hole-transporting layer are also the same as those in the first organic EL device mentioned above. However, the hole-transporting material for an organic EL device of the invention is required to be used in any one or more layers of the hole-transporting layer, the hole-injecting layer and the electron-blocking layer.

EXAMPLES

The invention will be explained in more detail in accordance with the Synthesis examples and the Examples which should not be construed as limiting the scope of the invention.

Preparation of a Ladder Compound

Example 1

Synthesis of Compound (7)

(1) Synthesis of Compound (7-a)

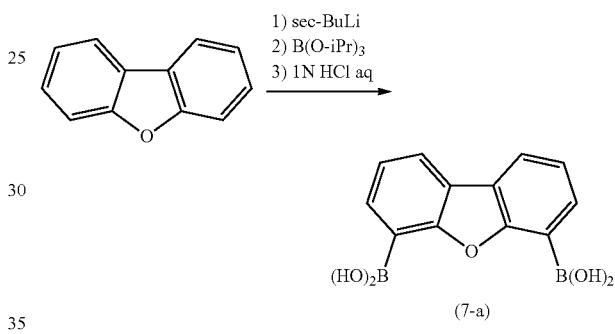

(7-a)

In a three-neck flask, 20.0 g (80.9 mmol) of dibenzofuran and 200 ml of dehydrated tetrahydrofuran were placed. In a nitrogen atmosphere, the reactor was cooled to −70° C. 53 ml (88.9 mmol) of a 1.68M s-butyllithium hexane solution was added to the reactor dropwise, followed by stirring at −70° C. for 1 hour. Further, 37.3 ml (162 mmol) of triisopropyl borate was added thereto, and the resultant was stirred at room temperature for 6 hours. After completion of the reaction, 100 ml of a 1N aqueous solution of HCl was added, and stirred for 30 minutes. The sample solution was transferred to a separating funnel, and extracted several times with dichloromethane. The extracted product was dried with anhydrous magnesium sulfate, filtered and concentrated. The concentrated product was washed by dispersing in hexane, whereby compound (7-a) as white solids were obtained.

The yield was 15.9 g and the percentage yield was 93%.

(2) Synthesis of Compound (7-b)

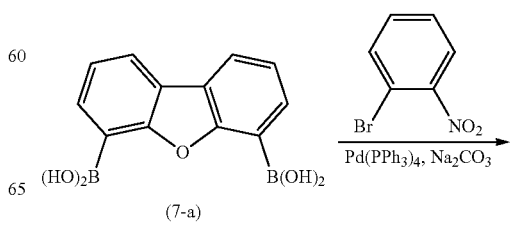

-continued

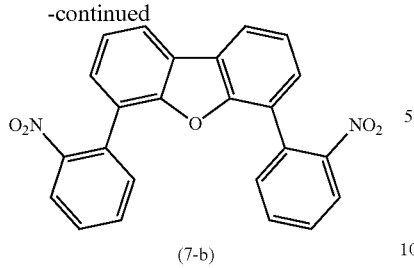

(7-b)

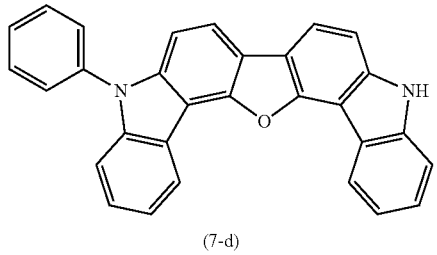

(7-d)

In a three-neck flask, 25.0 g (97.7 mmol) of compound (7-a), 59.2 g (293.1 mmol) of 2-nitrophenylboronic acid, 250 mL of a 2M aqueous sodium carbonate solution, 500 mL of 1,2-dimethoxyethane and 2.30 g (1.95 mmol) of Pd(PPh$_3$)$_4$ were placed, and the mixture was refluxed for 12 hours in a nitrogen atmosphere.

After completion of the reaction, the sample solution was filtrated, and the resulting solids were washed with methanol and hexane, whereby compound (7-b) was obtained.

The yield was 26.5 g and the percentage yield was 66%.

(3) Synthesis of Compound (7-c)

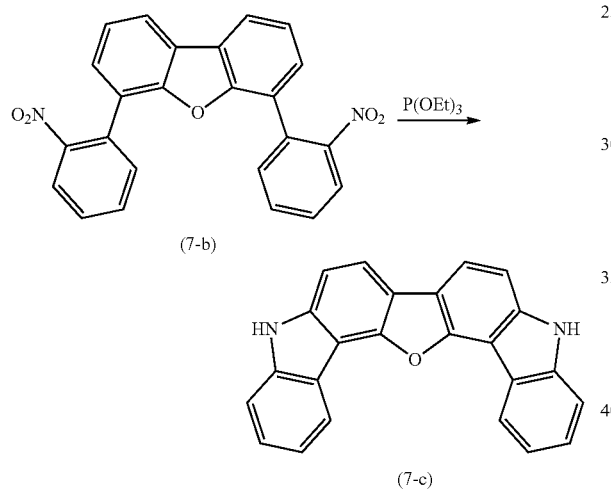

In a three-neck flask, 26.5 g (64.6 mmol) of compound (7-b) and 430 ml of triethyl phosphite were added, and the mixture was heated with stirring at 170° C. for 16 hours.

After completion of the reaction, distillation was conducted. The remaining triethyl phosphite and triethyl phosphite residues were removed, and the resulting organic layer was purified by silica gel chromatography (hexane:dichloromethane=10:1 to 5:1 to 1:1), whereby a compound (7-c) as yellow solids was obtained.

The yield was 2.22 g and the percentage yield was 54%.

(4) Synthesis of Compound (7-d)

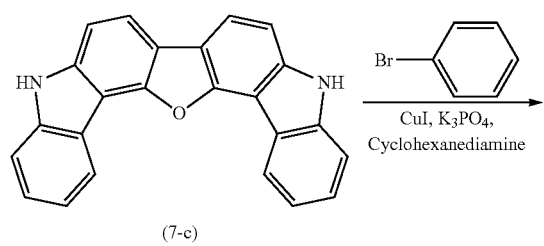

In a three-neck flask, 1.00 g (2.88 mmol) of compound (7-c), 0.430 g (2.74 mmol) of bromobenzene, 0.548 g (2.88 mmol) of copper iodide, 0.611 g (2.88 mmol) of tripotassium phosphate, 0.69 ml (5.76 mmol) of cyclohexanediamine and 20 mL of 1,4-dioxane were placed. The mixture was refluxed in a nitrogen atmosphere for 12 hours.

After completion of the reaction, a reaction product was filtrated through a celite, and the filtrated matter was transferred to a separating funnel and then extracted several times with dichloromethane. The resulting organic layer was dried with anhydrous magnesium sulfate, filtrated and concentrated. The resultant was purified by silica gel chromatography (hexane:dichloromethane=10:1 to 5:1), whereby compound (7-d) as white solids was obtained.

The yield was 0.644 g and the percentage yield was 53%.

(5) Synthesis of Compound (7)

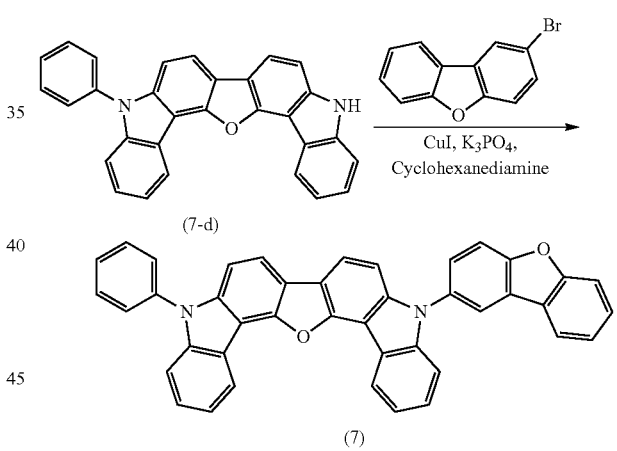

In a three-neck flask, 1.09 g (2.37 mmol) of compound (7-d), 0.877 g (3.55 mmol) of 2-bromodibenzofuran, 0.451 g (2.37 mmol) of copper iodide, 1.01 g (4.74 mmol) of tripotassium phosphate, 0.56 ml (4.74 mmol) of cyclohexanediamine and 20 mL of 1,4-dioxane were placed, and the mixture was refluxed for 12 hours in a nitrogen atmosphere. After completion of the reaction, a reaction product was filtrated through a celite, and the filtrated matter was transferred to a separating funnel and then extracted several times with dichloromethane. The resulting organic layer was dried with anhydrous magnesium sulfate, filtrated and concentrated. The resultant was purified by silica gel chromatography (hexane:dichloromethane=10:1 to 5:1), whereby compound (7) as white solids was obtained.

The yield was 0.644 g and the percentage yield was 78%.

The compound was identified by the molecular weight measurement by FD/MS. It was found that m/e was 588 relative to 588 of the molecular weight.

Production and Evaluation of Organic EL Device

Example 2

A 130 nm-thick glass substrate with ITO electrode lines (manufactured by GEOMATEC Co., Ltd.) was subjected to ultrasonic cleaning in isopropyl alcohol for 5 minutes and then UV ozone cleaning for 30 minutes.

The cleaned glass substrate with ITO electrode lines was mounted on a substrate holder in a vacuum deposition apparatus. First, on the surface of the side on which the ITO electrode lines had been formed, compound (HI1) was deposited by resistance heating so as to cover the ITO electrode lines to form a 20 nm-thick film, and subsequently compound (HT1) was deposited by resistance heating to form a 60 nm-thick film sequentially. The film-forming rate was 1 Å/s. These thin films function as a hole-injecting layer and a hole-transporting layer, respectively.

Next, on the hole-injecting/transporting layer, compound (7) and compound (BD1) were simultaneously deposited by resistance heating to form a 50 nm-thick thin film. At this time, compound (BD1) was deposited such that the mass ratio of compound (BD1) became 20% relative to the total mass of compound (7) and compound (BD1). The film forming rate was 1.2 Å/s and 0.3 Å/s, respectively. This thin film functions as a phosphorescent emitting layer.

Subsequently, on the phosphorescent emitting layer, compound (H1) was deposited by resistance heating to form a 10 nm-thick thin film. The film forming rate was 1.2 Å/s. This thin film functions as a barrier layer.

Next, on the barrier layer, compound (ET1) was deposited by resistance heating to form a 10 nm-thick thin film. The film forming rate was 1 Å/s. This film functions as an electron-injecting layer.

Subsequently, on this electron-injecting layer, a LiF film having a thickness of 1.0 nm was deposited at a film-forming rate of 0.1 Å/s.

Next, on the LiF film, metal aluminum was deposited at a film forming rate of 8.0 Å/s to form a metal electrode having a film thickness of 80 nm, whereby an organic EL device was produced.

The materials used in the production of the organic EL device was shown below:

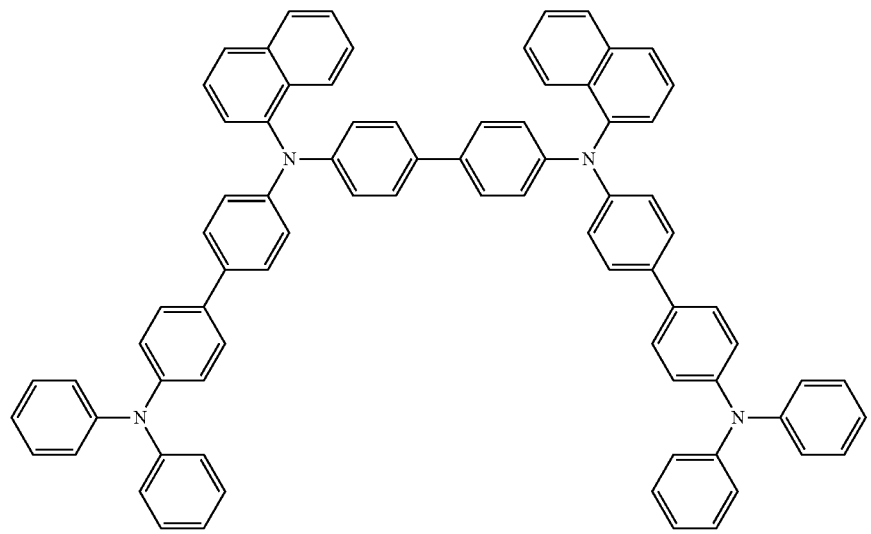

Compound (HI1)

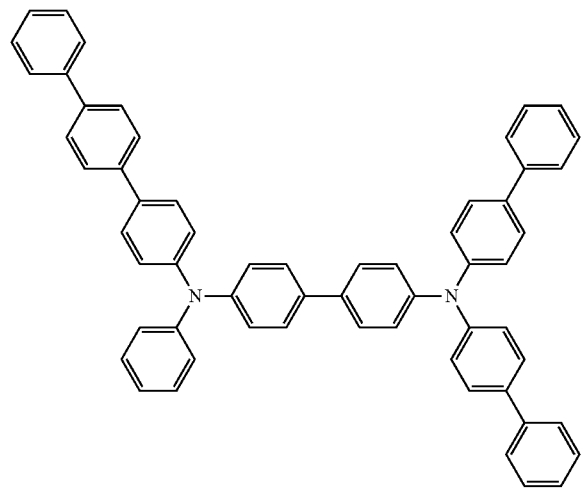

Compound (HT1)

Compound (H1)

Compound (BD1)

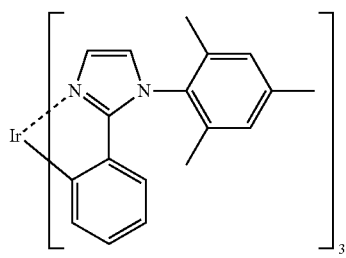

Compound (ET1)

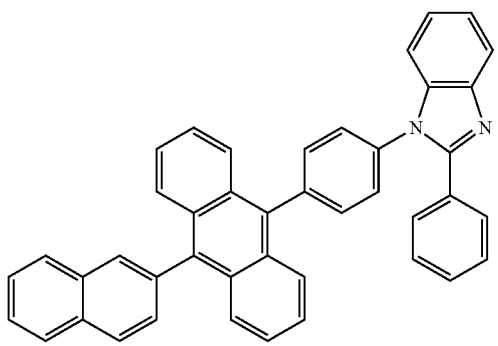

For the resulting organic EL device, the external quantum efficiency was evaluated by the following method. The results are shown in Table 1.

(1) External Quantum Efficiency (%)

The external quantum efficiency at a luminance of 1000 cd/m$^2$ was measured by a spectroradiometer (CS-1000 manufactured by Minolta) at 23° C. in a dry nitrogen gas atmosphere.

Comparative Example 1

An organic EL device was fabricated and evaluated in the same manner as in Example 1, except that compound (H2) was used instead of compound (7) as the phosphorescent host material. The results are shown in Table 1.

Compound (H2)

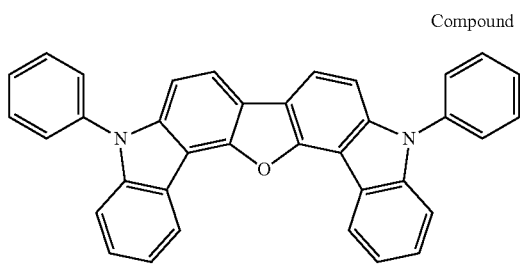

TABLE 1

|  | Emitting layer | Efficiency (%) |
| --- | --- | --- |
| Example 2 | Compound (7) | 18.5 |
| Comp. Ex. 1 | Compound (H2) | 12.0 |

As shown in Table 1, it can be understood that the organic EL device of Example 2 in which the compound of the invention prepared in Example 1 was used in the emitting layer had improved luminous efficiency as compared with the device of Comparative Example 1. The emission wavelength of the organic EL device of Example 2 was 475 nm.

Preparation of Ladder Compound

Example 3

Synthesis of Compound (40)

(1) Synthesis of Compound (40-a)

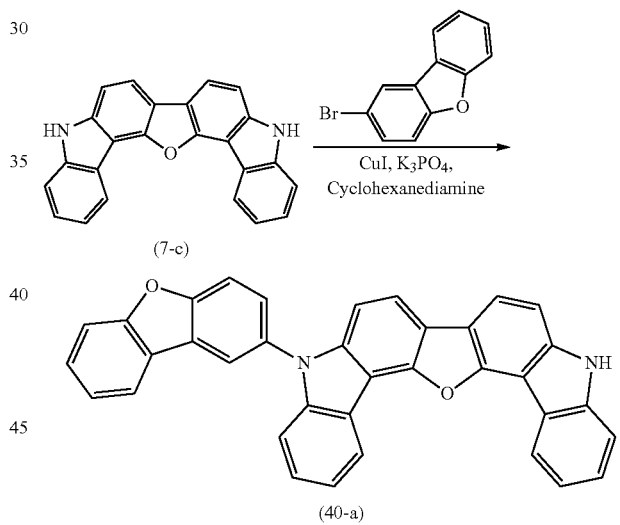

In a reaction container, 34.6 g (100 mmol) of compound (7-c), 24.7 g (100 mmol) of 2-bromodibenzofuran, 19.0 g (100 mmol) of copper iodide, 21.2 g (100 mmol) of tripotassium phosphate, 5.9 g (50 mmol) of cyclohexanediamine and 500 mL of dehydrated 1,4-dioxane were placed, and the mixture was refluxed in an argon atmosphere for 48 hours.

After completion of the reaction, a reaction product was filtrated through a celite, and the filtrated matter was transferred to a separating funnel and then extracted several times with toluene. The resulting organic layer was dried with anhydrous magnesium sulfate, filtrated and concentrated. The resultant was purified by silica gel chromatography (hexane:toluene=10:1 to 5:1 to 2:1), whereby compound (40-a) as white solids was obtained.

The yield was 11.8 g and the percentage yield was 23%.

(2) Synthesis of Compound (40)

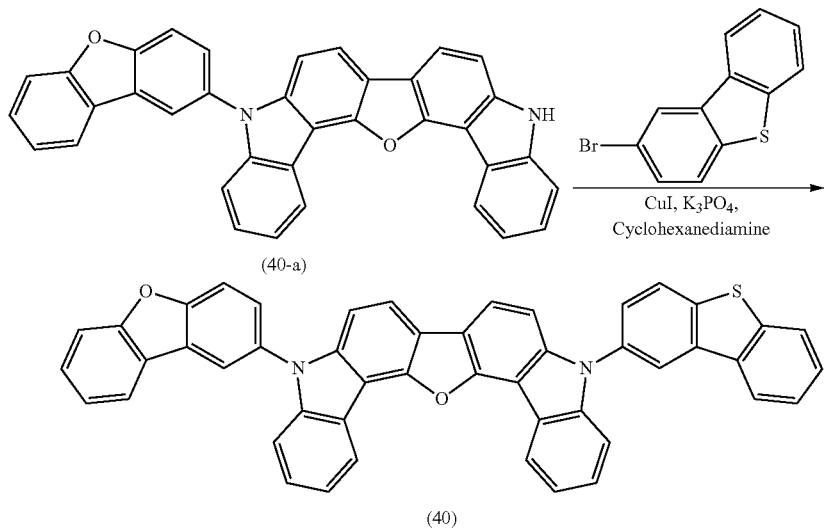

In a reaction container, 3.5 g (10 mmol) of compound (40-a), 2.9 g (11 mmol) of 2-bromodibenzothiophene, 1.9 g (10 mmol) of copper iodide, 2.1 g (10 mmol) of tripotassium phosphate, 0.6 g (5 mmol) of cyclohexanediamine and 60 mL of dehydrated 1,4-dioxane were placed, and the mixture was refluxed in an argon atmosphere for 24 hours.

After completion of the reaction, the solvent was removed by distillation under reduced pressure. 2000 mL of toluene was added to the residues, and the resultant was heated to 100° C. Matters remained undissolved were removed by filtration by silica gel, and the filtrate was concentrated. The resulting solids were purified by washing by suspending in acetone, whereby compound (40) as white solids was obtained.

The yield was 3.1 g and the percentage yield was 45%.

The compound was identified by the molecular weight measurement by FD/MS. It was found that m/e was 694 relative to 694 of the molecular weight.

Example 4

Synthesis of Compound (41)

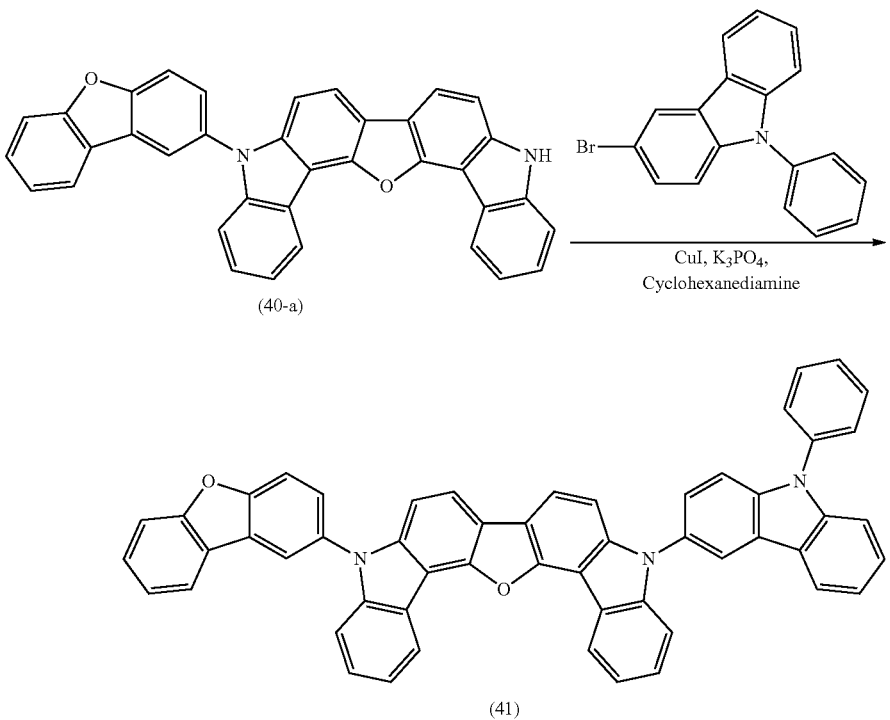

In a reaction container, 3.5 g (10 mmol) of compound (40-a), 3.6 g (11 mmol) of 3-bromo-9-phenylcarbazole, 1.9 g (10 mmol) of copper iodide, 2.1 g (10 mmol) of tripotassium phosphate, 0.6 g (5 mmol) of cyclohexadiamine and 50 mL of dehydrated 1,4-dioxane were placed, and the mixture was refluxed in an argon atmosphere for 40 hours.

After completion of the reaction, a reaction product was filtrated through a celite, and the filtrated matter was transferred to a separating funnel and then extracted several times with dichloromethane. The resulting organic layer was dried with anhydrous magnesium sulfate, filtrated and concentrated. The resultant was purified by silica gel chromatography (hexane:dichloromethane=4:1 to 2:1), whereby compound (41) as white solids was obtained.

The yield was 2.9 g and the percentage yield was 38%.

The compound was identified by the molecular weight measurement by FD/MS. It was found that m/e was 753 relative to 753 of the molecular weight.

Example 5

Synthesis of Compound (42)

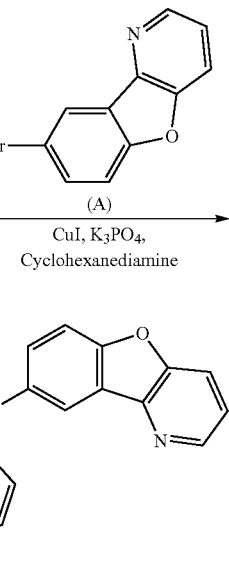

(40-a)

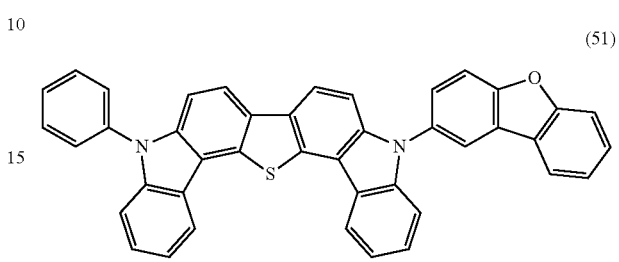

(A)
CuI, K₃PO₄,
Cyclohexanediamine

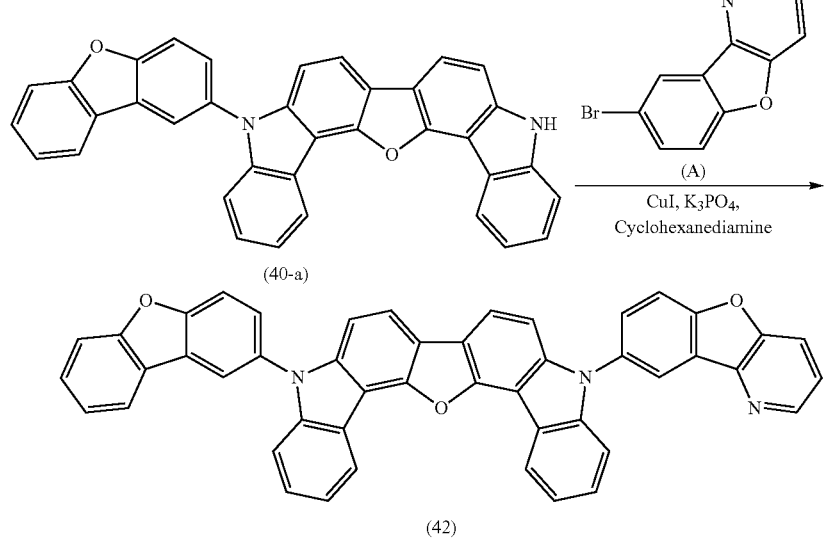

(42)

In a reaction container, 3.5 g (10 mmol) of compound (40-a), 3.0 g (12 mmol) of intermediate (A) synthesized by a method in WO2013-038650, 1.9 g (10 mmol) of copper iodide, 2.1 g (10 mmol) of tripotassium phosphate, 1.2 g (10 mmol) of cyclohexanediamine and 40 mL of dehydrated 1,4-dioxane were placed, and the mixture was refluxed in an argon atmosphere for 72 hours.

After completion of the reaction, a reaction product was filtrated through a celite, and the filtrated matter was transferred to a separating funnel and then extracted several times with toluene and dichloromethane. The resulting organic layer was together dried with anhydrous magnesium sulfate, filtrated and concentrated. The resultant was purified by silica gel chromatography (hexane:dichloromethane=2:1 to 1:2 to 1:10), whereby a compound (42) as white solids was obtained.

The yield was 1.4 g and the percentage yield was 21%.

The compound was identified by the molecular weight measurement by FD/MS. It was found that m/e was 679 relative to 679 of the molecular weight.

Example 6

Synthesis of Compound (51)

(51)

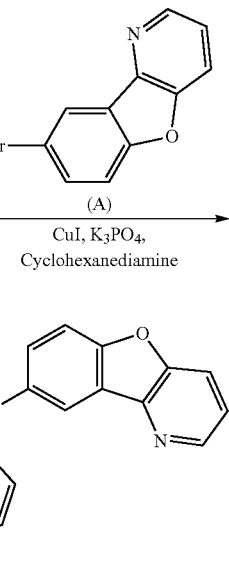

Compound (51) was synthesized by the method stated in Example 1, by using dibenzothiophene instead of dibenzofuran as the starting material.

Example 7

Synthesis of Compound (128)

(1) Synthesis of compound (128-a)

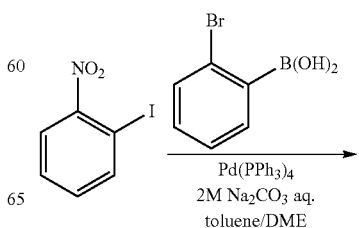

Pd(PPh₃)₄
2M Na₂CO₃ aq.
toluene/DME

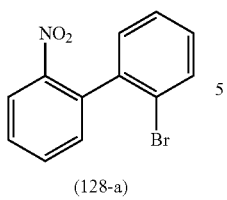

(128-a)

In a reaction container, 24.9 g (100 mmol) of 2-iodonitrobenzene, 20.0 g (100 mmol) of 2-bromophenylboronic acid, 2.3 g (2 mmol) of Pd(PPh$_3$)$_4$, 100 mL of a 2M aqueous solution of sodium carbonate, 150 mL of toluene and 150 mL of 1,2-dimethoxyethane (DME) were placed, and the mixture was refluxed in an argon atmosphere for 24 hours.

After completion of the reaction, an organic phase was taken out, dried with anhydrous magnesium sulfate, and then the solvent was removed by distillation under reduced pressure. The residues were purified by silica gel column chromatography (hexane:toluene=2:1 to 1:2), whereby compound (128-a) as white solids was obtained.

The yield was 15.3 g and the percentage yield was 55%.

(2) Synthesis of Compound (128-b)

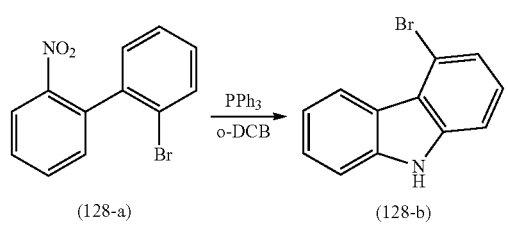 [SMILES: O=[N+]([O-])c1ccccc1-c1ccccc1Br ; Brc1cccc2[nH]c3ccccc3c12 ; "PPh3"]

In a reaction container, 15.3 g (55 mmol) of compound (128-a), 36.1 g (137.5 mmol) of triphenylphosphine and 500 mL of o-dichlorobenzene (o-DCB) were placed, and the mixture was reacted at 185° C. for 15 hours in an argon atmosphere.

After completion of the reaction, the residues obtained by removing the solvent by distillation under reduced pressure were diluted with toluene. Deposited matters were filtrated, and purified by silica gel column chromatography (hexane:toluene=1:1 to 1:3), whereby compound (128-b) as white solids was obtained.

The yield was 6.1 g and the percentage yield was 45%.

(3) Synthesis of Compound (128-c)

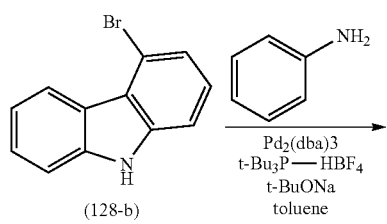

(128-c)

In a reaction container, 5.4 g (22 mmol) of compound (128-b), 0.9 g (10 mmol) of aniline, 0.37 g (0.4 mmol) of Pd$_2$(dba)$_3$, 0.46 g (1.6 mmol) of tri-t-butylphosphonium tetrafluoroborate, 2.7 g (28 mmol) of sodium t-butoxide and 30 mL of dehydrated toluene were placed. The mixture was refluxed in an argon atmosphere for 72 hours.

After completion of the reaction, the residues obtained by removing the solvent by distillation under reduced pressure were purified by silica gel column chromatography (hexane:toluene=1:1 to 1:3), whereby compound (128-c) as white solids was obtained.

The yield was 1.4 g and the percentage yield was 33%.

(4) Synthesis of Compound (128-d)

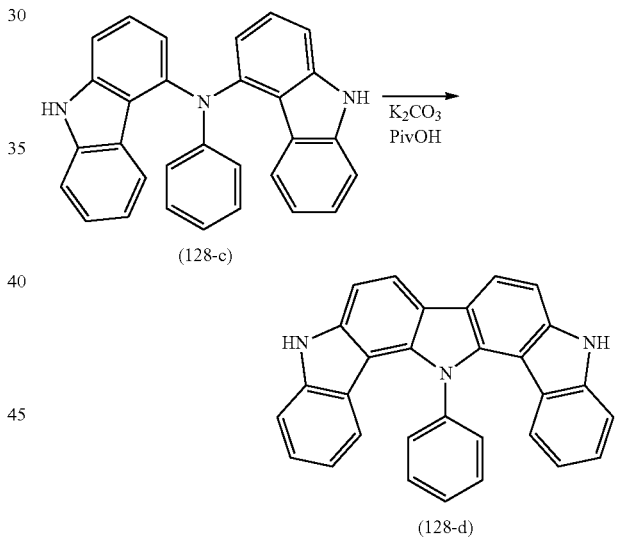

In a reaction container, 1.4 g (3.3 mmol) of compound (128-c), potassium carbonate and 30 mL of dehydrated toluene were placed. The mixture was refluxed in an argon atmosphere for 72 hours.

After completion of the reaction, the residues obtained by removing the solvent by distillation under reduced pressure were purified by silica gel column chromatography (hexane:toluene=1:1 to 1:3), whereby compound (128-c) as white solids was obtained.

The yield was 0.9 g and the percentage yield was 64%.

(5) Synthesis of Compound (128)

Compound (128) was synthesized by the method stated in Example 3, by using compound (128-d) instead of compound (7-c) as the starting material.

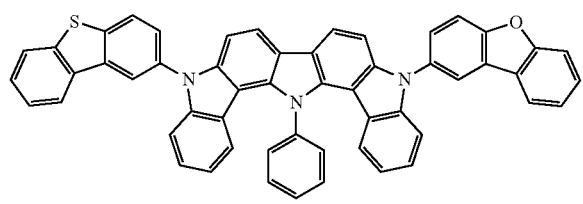

(128)

[Production and Evaluation of Organic EL Device]

Example 8

An organic EL device was fabricated in the same manner as in Example 2, except that compound (H3) was used instead of compound (H1).

The fabricated organic EL device was caused to emit light by direct current driving to measure a luminance and a current density, whereby a voltage and a luminous efficiency (external quantum efficiency) at a current density of 1 mA/cm$^2$ were obtained. Further, a LT70 luminance life (time that elapsed until the initial luminance was reduced to 70%) was measured at an initial luminance of 3000 cd/m$^2$. This life was expressed as a relative value taking the value of the devices in Comparative Examples as 100. The results of evaluating the luminous performance are shown in Table 2.

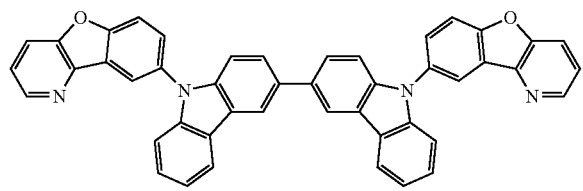

(H3)

Examples 9 to 21

Organic EL devices were fabricated and evaluated in the same manner as in Example 8, except that compounds shown in Table 2 were used instead of compound (7) as the phosphorescent host material. The results are shown in Table 2.

Comparative Example 2

An organic EL device was fabricated and evaluated in the same manner as in Example 8, except that compound (H2) was used instead of compound (7) as the phosphorescent host material. The results are shown in Table 2.

Comparative Example 3

An organic EL device was fabricated and evaluated in the same manner as in Example 8, except that compound (H4) was used instead of compound (7) as the phosphorescent host material. The results are shown in Table 2.

Comparative Example 4

An organic EL device was fabricated and evaluated in the same manner as in Example 8, except that compound (H5) was used instead of compound (7) as the phosphorescent host material. The results are shown in Table 2.

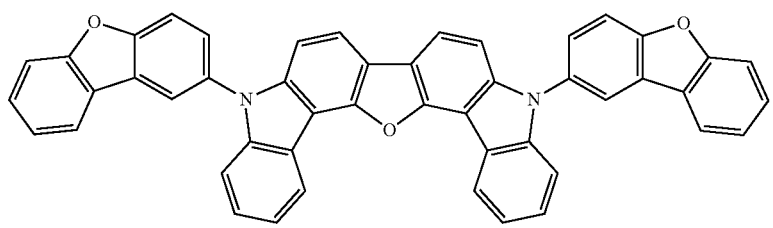

(H4)

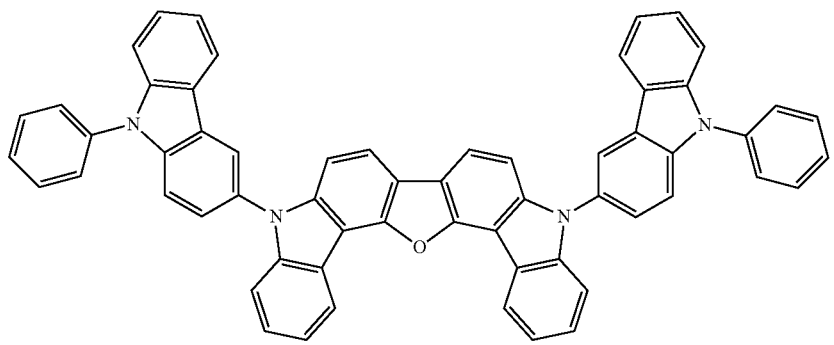

(H5)

TABLE 2

| Host material for emitting layer | | Voltage (V) | External quantum efficiency (%) | LT70 luminance life (relative value) |
|---|---|---|---|---|
| Example 8 | Compound (7) | 4.9 | 17.6 | 660 |
| Example 9 | Compound (40) | 4.5 | 17.0 | 580 |
| Example 10 | Compound (41) | 4.8 | 17.1 | 870 |
| Example 11 | Compound (42) | 4.1 | 15.5 | 430 |
| Example 12 | Compound (151) | 5.3 | 15.9 | 210 |
| Example 13 | Compound (155) | 5.5 | 14.8 | 380 |
| Example 14 | Compound (157) | 4.9 | 16.9 | 730 |
| Example 15 | Compound (161) | 5.3 | 16.7 | 330 |
| Example 16 | Compound (162) | 4.6 | 15.2 | 750 |
| Example 17 | Compound (164) | 4.3 | 14.7 | 220 |
| Example 18 | Compound (173) | 4.8 | 16.7 | 290 |
| Example 19 | Compound (179) | 4.7 | 16.0 | 450 |
| Example 20 | Compound (182) | 4.5 | 17.0 | 640 |
| Example 21 | Compound (213) | 5.0 | 15.4 | 440 |
| Comp. Ex. 2 | Compound (H2) | 6.0 | 13.5 | 10 |
| Comp. Ex. 3 | Compound (H4) | 5.5 | 14.1 | 100 |
| Comp. Ex. 4 | Compound (H5) | 5.8 | 14.0 | 40 |

As shown in Table 2, the organic EL devices in Examples 8 to 21 that used the compounds of the invention as the phosphorescent host material in the emitting layer could be driven at a lower voltage, had a longer life and exhibited an excellent luminous efficiency as compared with the devices of Comparative Examples. It can be understood that the compound of the invention that does not have a symmetrical axis has excellent properties as a material for an organic EL device as compared with the compounds in Comparative Examples that have a symmetrical axis.

INDUSTRIAL APPLICABILITY

The compound of the invention can be used as a material for an organic EL device.

The organic EL device of the invention can be utilized for a planar emitting body such as a flat panel display of a wall-hanging television, a copier, a printer, a back light of a liquid crystal display, or a light source in instruments or the like, a sign board, a signal light or the like.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The Japanese application specification claiming priority under the Paris Convention are incorporated herein by reference in its entirety.

The invention claimed is:

1. A compound represented by the following formula (1):

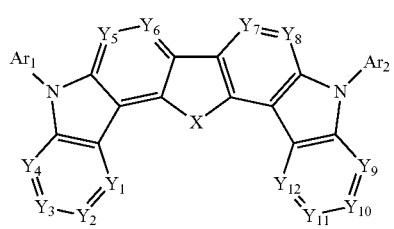

(1)

wherein in the formula (1),

X is O, S or a group represented by N—Ra;

$Y_1$ to $Y_{12}$ are independently N or a group represented by C—Ra;

$Ar_1$ and $Ar_2$ are independently a substituted or unsubstituted aryl group including 6 to 30 ring carbon atoms or a substituted or unsubstituted heteroaryl group including 5 to 30 ring atoms;

Ra is a hydrogen atom, a deuterium atom, a substituted or unsubstituted aryl group including 6 to 30 ring carbon atoms, a substituted or unsubstituted heteroaryl group including 5 to 30 ring atoms, a substituted or unsubstituted alkyl group including 1 to 30 carbon atoms, a substituted or unsubstituted fluoroalkyl group including 1 to 30 carbon atoms, a substituted or unsubstituted cycloalkyl group including 3 to 30 ring carbon atoms, a substituted or unsubstituted aralkyl group including 7 to 30 carbon atoms, a substituted phosphoryl group, a substituted silyl group, a substituted germanium group, a cyano group, a nitro group or a carboxy group;

if two or more Ras are present in the formula (1), the plural Ras may be the same or different; and provided that, when $Ar_1$ and $Ar_2$ are the same substituents, then $Y_1$ and $Y_{12}$ are not the same as each other, $Y_2$ and $Y_{11}$ are not the same as each other, $Y_3$ and $Y_{10}$ are not the same as each other, $Y_4$ and $Y_9$ are not the same as each other, $Y_5$ and $Y_8$ are not the same as each other, and $Y_6$ and $Y_7$ are not the same as each other.

2. The compound according to claim 1, wherein $Ar_1$ and $Ar_2$ in the formula (1) are independently a substituted or unsubstituted aryl group including 6 to 30 ring carbon atoms.

3. The compound according to claim 1, wherein $Ar_1$ and $Ar_2$ in the formula (1) are independently a substituted or unsubstituted heteroaryl group including 5 to 30 ring atoms.

4. The compound according to claim 1, wherein X in the formula (1) is a group represented by N—Ra.

5. The compound according to claim 1, wherein X in the formula (1) is O or S.

6. The compound according to claim 1, wherein $Y_1$ to $Y_{12}$ in the formula (1) are independently a group represented by C—Ra.

7. The compound according to claim 1, wherein $Ar_1$ is not the same as $Ar_2$ in the formula (1).

8. The compound according to claim 1, wherein $Ar_1$ in the formula (1) is represented by wherein $L_1$ is a substituted or unsubstituted arylene group including 6 to 30 ring carbon atoms or a substituted or unsubstituted heteroarylene group including 5 to 30 ring atoms; and $R_1$ is a substituted or unsubstituted aryl group including 6 to 30 ring carbon atoms or a substituted or unsubstituted heteroaryl group including 5 to 30 ring atoms.

9. The compound according to claim 8, wherein $L_1$ is a substituted or unsubstituted arylene group including 6 to 30 ring carbon atoms.

10. The compound according to claim 8, wherein $L_1$ is a substituted or unsubstituted heteroarylene group including 5 to 30 ring atoms.

11. A material for an organic electroluminescence device that comprises the compound according to claim 1.

12. An organic electroluminescence device comprising:
an anode and a cathode; and
one or more organic thin film layers including an emitting layer between the anode and the cathode, wherein at least one layer of the organic thin film layers comprises the material for an organic electroluminescence device according to claim 11.

13. The organic electroluminescence device according to claim 12, wherein the emitting layer comprises a phosphorescent emitting material and the phosphorescent emitting material is an ortho-metalated complex of a metal atom selected from iridium (Ir), osmium (Os) and platinum (Pt).

14. The organic electroluminescence device according to claim 12, wherein the emitting layer comprises the material for an organic electroluminescence device.

15. The organic electroluminescence device according to claim 14, further comprising an electron-transporting zone between the cathode and the emitting layer, wherein the electron-transporting zone comprises the material for an organic electroluminescence device.

\* \* \* \* \*